US009476058B2

(12) United States Patent
Lim

(10) Patent No.: US 9,476,058 B2
(45) Date of Patent: Oct. 25, 2016

(54) METHOD FOR SPEEDING UP PLANT GROWTH AND IMPROVING YIELD BY INTRODUCING PHOSPHATASES IN TRANSGENIC PLANT

(71) Applicant: Versitech Limited, Hong Kong (HK)

(72) Inventor: Boon Leong Lim, Hong Kong (HK)

(73) Assignee: Versitech Limited, Hong Kong (HK)

( * ) Notice: Subject to any disclaimer, the term of this patent is extended or adjusted under 35 U.S.C. 154(b) by 615 days.

(21) Appl. No.: 13/863,049

(22) Filed: Apr. 15, 2013

(65) Prior Publication Data

US 2013/0291224 A1 Oct. 31, 2013

Related U.S. Application Data

(62) Division of application No. 12/640,674, filed on Dec. 17, 2009, now abandoned.

(60) Provisional application No. 61/138,918, filed on Dec. 18, 2008.

(51) Int. Cl.
*C12N 15/82* (2006.01)
*C12N 9/16* (2006.01)

(52) U.S. Cl.
CPC ............ *C12N 15/8245* (2013.01); *C12N 9/16* (2013.01); *C12N 15/8261* (2013.01)

(58) Field of Classification Search
None
See application file for complete search history.

(56) References Cited

U.S. PATENT DOCUMENTS 7,417,181 B2 8/2008 Wang et al.
7,569,389 B2 8/2009 Feldmann et al.
7,655,833 B2 2/2010 Heilmann et al.
9,238,819 B2 1/2016 Lim
2007/0039067 A1* 2/2007 Feldmann ............ C07K 14/415 800/278

OTHER PUBLICATIONS

Hill et al (Functional analysis of conserved histidines in ADP-glucose pyrophosphorylase from *Escherichia coli*. Biochem. Biophys. Res. Comm. 244:573-577, 1998).*

Guo et al (Protein tolerance to random amino acid change, Proc. Natl. Acad. Sci. USA 101:9205-9210, 2004).*

Zhu et al (Expression patterns of purple acid phosphatase genes in Arabidopsis organs and functional analysis of AtPAP23 predominantly transcribed in flower. Plant Mol. Biol. 59:581-594, 2005).*

Jones et al (Circadian Regulation of Sucrose Phosphate Synthase Activity in Tomato by Protein Phosphatase Activity. Plant Physiol. 113: 1167-1175, 1997).*

Alonso, et al., Genome-Wide Insertional Mutagenesis of *Arabidopsis thaliana*, www.sciencemag.orq., *Science* vol. 301, pp. 653-657; Aug. 1, 2003.

Antonio, et al., "Quantification of sugars and sugar phosphates in *Arabidopsis thaliana* tissues using porous graphitic carbon liquid chromatography-electrospray ionization mass spectrometry," *J. of Chromatography*A, 1172; pp. 170-178; 2007.

Axelos, et al., The gene family encoding the *Arabidopsis thaliana* translation elongation factor EF-1x: Molecular cloning, characterization and expression, *Mol Gen Genet*, 219; pp. 106-112; 1989.

Bozzo, et al., "Purification and characterization of two secreted purple acid phosphatase isozymes from phosphate-starved tomato (Lycopersicon esculentum) cell cultures," *Eur. J. Biochem* 269; pp. 6278-6286; 2002.

Bozzo, et al., "Structural and kinetic properties of a novel purple acid phosphatase from phosphate-starved tomato (Lycopersicon esculentum) cell cultures", *Biochem*. J. 377, pp. 419-428; 2004.

Bradford; "A Rapid and Sensitive Method for the Quantitation of Microgram Quantities of Protein Utilizing the Principle of Protein-Dye Binding"; *Analytical Biochemistry* 72; pp. 248-254;1976.

Cashikar, et al., "Biochemical Characterization and Subcellular Localization of the Red Kidney Bean Purple Acid Phosphatase"; *Plant Physiol*. 114, pp. 907-915; 1997.

Clough et al., "Floral dip: a simplified method for Agrobacterium-mediated transformation of *Arabidopsis thaliana"; The Plant Journal* 16(6), pp. 735-743; 1998.

Coello; "Purification and characterization of secreted acid phosphatase in phosphorus-deficient *Arabidopsis thaliana"; Physiologia Plantarum* 116, pp. 293-298; 2002.

Del Pozo, et al.; "A type 5 acid phosphatase gene from *Arabidopsis thaliana* is induced by phosphate starvation and by some other types of phosphate mobilising/oxidative stress conditions"; *The Plant Journal* 19(5), pp. 579-589; 1999.

Doehlert; "Ketose Reductase Activity in Developing Maize Endosperm"; *Plant Physiol*. 84, pp. 830-834; 1987.

Guo et al., "Protein tolerance to random amino acid change," *PNAS* 101; pp. 9205-9210; 2004.

He et al., "A Cell Wall-associated, Receptor-like Protein Kinase"; *The Journal of Biological Chemistry*, vol. 271, No. 33, pp. 19789-19793; Aug. 16, 1996.

Hegeman, etal., "A Novel Phytase with Sequence Similarity to Purple Acid Phosphatases Is Expressed in Cotyledons of Germinating Soybean Seedlings"; *Plant Physiology*, vol. 126, pp. 1598-1608; Aug. 2001.

Hofgen, et al., "Storage of competent cells for Agrobacterium transformation"; *Nucleic Acids Research*, vol. 16, No. 20, pp. 9877;1988.

Kaida, et al., "Isolation and characterization of four cell wall purple acid phosphatase genes from tobacco cells"; *Biochimica et Biophysica Acta* 1625, pp. 134-140 2003.

Kim etal., "Isolation and Characterization of a Pollen-specific cDNA Clone from Easter Lily," *J. Plant Biol*., vol. 19, No. 3, pp. 197-202; Sep. 1996.

Klabunde, et al., "Mechanism of Fe (III)—Zn(II) Purple Acid Phosphatase Based on Crystal Structures"; *J. Moi. Biol*. 259, pp. 737-748; 1996.

Klabunde, et al., "The Dimetal Center in Purple Acid Phosphatases, Structure and Bonding"; vol. 89, pp. 177-198; 1997.

(Continued)

*Primary Examiner* — Medina A Ibrahim
*Assistant Examiner* — Wayne Zhong
(74) *Attorney, Agent, or Firm* — Dentons US LLP

(57) ABSTRACT

Transgenic plants having increased growth rate, increased sugar content, and increase yield are disclosed, and methods for making the same. The transgenic plants have a gene coding for a phosphatase having a C-terminal motif under control of a heterologous promoter incorporated into the genomic DNA of the plant.

10 Claims, 14 Drawing Sheets

(56) References Cited

OTHER PUBLICATIONS

Kumar, et al., "MEGA3: Integrated software for Molecular Evolutionary Genetics Analysis and sequence alignment"; *Briefings in Bioinformatics*, vol. 5, No. 2, pp. 150-163; Jun. 2004.
Liao, et al., "GmPAP3, a novel purple acid phosphatase-like gene in soybean induced by NaCl stress but not phosphorus deficiency"; *Gene* 318, pp. 103-111; 2003.
Li, et al., "Purple Acid Phosphatases of Arabidopsis thaliana"; *The Journal of Biological Chemistry*, vol. 277, No. 31, pp. 27772-27781; Aug. 2, 2002.
Li, et at., "eDNA Cloning and in vitro Expressions of Three Putative Purple Acid Phosphotese Cones from *Arabidopsis"; J Nat Sci*; Hunan Norm Univ. vol. 26, No. 3, pp. 78-82; Sep. 2003.
Liu, et al., "COP1-Mediated Ubiquitination of Constans Is Implicated in Cryptochrome Regulation of Flowering in *Arabidopsis"; The Plant Cell*, vol. 20, pp. 292-306; Feb. 2008.
Lung, et al., "Phytase activity in tobacco (Nicotiana tabacum) root exudates is exhibited by a purple acid phosphatase"; Phytochemistry 69, pp. 365-373; 2008.
Lunn, et al., "Sugar-induced increases in trehalose 6-phosphate are correlated with redox activation of ADPglucose pyrophosphorylase and higher rates of starch synthesis in Arabidopsis thaliana"; Biochem. J. 397, pp. 139-148; 2006.
Luo, et al., "Simultaneous determination of multiple intracellular metabolites in glycolysis, pentose phosphate pathway and tricarboxylic acid cycle by liquid chromatography-mass spectrometry"; Journal of Chromatography A, 1147, pp. 153-164; 2007.
Park et al., "Over-expression of an arabidopsis family a sucrose phosphate synthase (SPS) gene alters plant growth and fibre development"; Transgenic Res 17, pp. 181-192; 2008.
Patel, et al., "Secreted Purple Acid Phosphatase from *Arabidopsis thaliana*, Phosphorus in Plant Biology: Regulatory Roles in Molecular, Cellular, Organismic, and Ecosystem Processes"; 1998.
Schenk, et al., "Binuclear Metal Centers in Plant Purple Acid Phosphatases: Fe-Mn in Sweet Potato and Fe—Zn in Soybean"; *Archives of Biochemistry and Biophysics*, vol. 370, No. 2, pp. 183-189; Oct. 15, 1999.
Schenk, et al., "Purple acid phosphatases from bacteria: similarities to mammalian and plant enzymes"; *Gene* 255 pp. 419-424; 2000.
Shimaoka, et al., "Isolation of Intact Vacuoles and Proteomic Analysis of Tonoplast from Suspension-Cultured Cells of *Arabidopsis thaliana"; Plant Cell Physiol*. 45(6), pp. 672-683; 2004.
Thompson, et al., "Autophagic Nutrient Recycling in Arabidopsis Directed by the ATG8 and ATG12 Conjugation Pathways"; *Plant Physiology*, vol. 138, pp. 2097-2110; Aug. 2005.
Veljanovski, et al., "Biochemical and Molecular Characterization of AtPAP26, a Vacuolar Purple Acid Phosphatase Up-Regulated in Phosphate-Deprived *Arabidopsis* Suspension Cells and Seedlings"; *Plant Physiology*, vol. 142, pp. 1282-1293; Nov. 2006.
Wu, et al., "Phosphate Starvation Triggers Distinct Alterations of Genome Expression in Arabidopsis Roots and Leaves"; *Plant Physiology*, vol. 132, pp. 1260-1271; Jul. 2003.
Wu, et al., "Two New Clock Proteins, LWD1 and LWD2, Regulate *Arabidopsis* Photoperiodic Flowering"; *Plant Physiology*, vol. 148, pp. 948-959; Oct. 2008.
Xiao, etal., "Transgenic expression of a novel *M. truncatula* phytase gene results in improved acquisition of organic phosphorus by *Arabidopsis"; Planta*, 222, pp. 27-36; 2005.
Xiao, et al., "Improved phosphorus acquisition and biomass production in *Arabidopsis* by transgenic expression of a purple acid phosphatase gene from *M. truncatula"; Plant Science* 170, pp. 191-202; 2006.
Zhang, et al., "An Arabidopsis Purple Acid Phosphatase with Phytase Activity Increases Foliar Ascorbate"; *Plant Physiology*, vol. 146, pp. 431-440; Feb. 2008.
Zhu, et al., "Expression patterns of purple acid phosphatase genes in Arabidopsis organs and functional analysis of AtPAP23 predominantly transcribed in flower"; *Plant Molecular Biology* 59, pp. 581-594; 2005.
U.S. Appl. No. 14/945,406, filed Nov. 18, 2015, Lim.

* cited by examiner

FIG. 2A

(A) Transmembrane motif (Aligned)

| Protein Sequences | |
|---|---|
| AtPAP2_gi\|15222978\|ref\|NP_172843 | A A LMVV VLL FII FF |
| AtPAP9_gi\|20257481\|gb\|AAM15910 | L I A VMVV VIF FV FL |
| Brassica_rapa_subsp._pekinensis_clone... | L V A LLVI VLL FII FF |
| Hordeum_vulgare_PUT-161a-Hordeum_vulg... | I L I VMFALML FAL FL |
| Medicago_AC202582_HTG_Medicago_trunca... | V VLVL AFM IL FV |
| OsPAP2__NM_001065273 | LF L IV VMFALVL F L FL |
| Poplar_trichocarpa_ref\|NC_008476.1\| | V A VLVL AFV L A |
| Saccharum_officinarum_28138_PlantGDB-... | L L I VLFALLL F F FL |
| Solanum_tuberosum_PUT-157a-Solanum_tu... | V V VLML AFM IV FL |
| Vitis_vinifera__AM458569_modified | V A ILVL AFM VI FV |
| Zea_mays_EU975503 | L L I VMFALLL F F IL |
| Physcomitrella_patens_subsp._patens_g... | IVAFLFVLAL AAA LF |

(B) 614th-636 a.a. (Unaligned)

| Protein Sequences | |
|---|---|
| AtPAP2_gi\|15222978\|ref\|NP_172843 | L A A LMVV VLL FII FF |
| AtPAP9_gi\|20257481\|gb\|AAM15910 | MVV VIF FV FL V |
| Brassica_rapa_subsp._pekinensis_clone... | A LLVI VLL FII FF |
| Hordeum_vulgare_PUT-161a-Hordeum_vulg... | I L I VMFALML FAL FL |
| Medicago_AC202582_HTG_Medicago_trunca... | L V VLVL AFM IL F |
| OsPAP2__NM_001065273 | F L IV VMFALVL F L FLI |
| Poplar_trichocarpa_ref\|NC_008476.1\| | VL AFV L A |
| Saccharum_officinarum_28138_PlantGDB-... | L L I VLFALLL F F FLI |
| Solanum_tuberosum_PUT-157a-Solanum_tu... | VLML AFM IV FL A |
| Vitis_vinifera__AM458569_modified | A ILVL AFM VI FV A |
| Zea_mays_EU975503 | L L I VMFALLL F F IL |
| Physcomitrella_patens_subsp._patens_g... | V I IVAFLFVLAL |

FIG. 2B

```
AtPAP2    MIMNFS-E-F LLLEVSVFVS SADSKATLSI SPNALNRSGD SVVIQWSGVD SPSDLDWLGL 58
BnPAP2    MIVDFS-T-F ILSEISVFIS SANAKATLSI SPKTLSRSGD SILIKWSNVD SPSDLDWLGI 57
GmPAP2    MIEDLE-LEF LESLEDIFEH LAESKESLTA IPTTLEASGA TVNLRWSGIP SPSDLDFLAI 59
ZmPAP2    MYPENPHLRF LLELAVAAVA AGGAAANTTL ER-TASESGN QIKIIWSGLP APDGLDVVAI 57
AtPAP15   MT[illegible]-E-F LLLLLFCFLS PAISSA[illegible] [illegible] [illegible] [illegible] 19
Consensus MXXXXX-XXF LLXXXXXFXX XAXXXAXXXX XPXXXXXSGX XXXXXWSXXX XPXXLDXXXX

AtPAP2    YSPPESPNDH FIGYKFLNES ETWKDGEGSI SLPLT-NLRS NYTFRIFRWS ESEIDPKHKD 117
BnPAP2    YSPPDSPHDH FIGYKFLNVS ETWQSGSGAI SLPLT-NLRS NYTFRIFRWT QSEINPKHKD 116
GmPAP2    YSPPTSPHDN FIGYLFLSQS ATWRTGSGNL SLPLV-DLRS NYSFRIFSWT RAEINPKRQD 118
ZmPAP2    YSPPSSLDRD FLGYLFLNGS ASWRGGSGEL SLPLLPTLRA PYQFRLFRWP AKEYSYHHVD 117
AtPAP15   HSIPSTLDGP FV[illegible] [illegible]V TVPLDTSLRG [illegible] EQAIDLPDTD 62
Consensus YSPPXSXXXX FXGYXFLXXS XXWXXGXGXX SLPLXXXLRX XYXFRXFXWX XXEIXXXXXD

AtPAP2    HDQNPLPGTK HLLAESEQLT FGS-GVGMPE QIHLSFTN-- -MVNTMRVMF VAGDGE---- 169
BnPAP2    HDQNPLPGTK HLLAESEQVS FGSAGVGRPE QIHLAFED-- -KVNRMRVTF VAGDGE---- 169
GmPAP2    HDHNPLPVTR HLLAHSEEVS FAPHR--GPQ QIHLAFVGAH GKEEDMRVMY IARDPR---- 172
ZmPAP2    HDQNPLPHGK HRVAVSADVS VGDPA--RPE QLHLAFAD-- -EVDEMRVLF VGGDRG---- 168
AtPAP15   [illegible]PRVR RRV[illegible]IG F[illegible]-E--EPE QISLSLSSDH -[illegible]DSIWVSW ITGEEQIGKK 92
Consensus HDXNPLPXXX HXXAXSXXXX FXXXXVGXPE QIHLXFXXXH -XXXXMRVXX XXGDXX----

AtPAP2    ---------E RHVRYGESK- -DLLGNSAAA RGMRYEREHM CDSPANSTIG WRDPGWIFDT 218
BnPAP2    ---------E REVRYGEQK- -DALANSAAA RGIRYEREHM CNAPANSTVC WRDPGWIFHT 218
GmPAP2    ---------E RYVRYGERE- -DKLDGIAVA RVERYEREHM CDAPANTSVG WRDPGEINDA 221
ZmPAP2    ---------E RVVRYGLQKE DDKEWKEVGT DVSTYEQRHM CDWPANSSVA WRDPGEVFDG 219
AtPAP15   VKEEDEISIN SVVQEGTLRH -ESLSHEAKG HSLVYSQLYP EDGLLNMT[illegible] [illegible]SGIIHHV 145
Consensus ---------E XXVRYGXXXX -DXLXXXAXX XXXXYEXXHM CDXPANXXXX WRDPGXIXXX

AtPAP2    VMKNLNDGVR YYYRVGSDSK -GWSEIHSMI ARDVTAEETV A---FMFGDM GCATPYITFI 274
BnPAP2    VMKNLNGGVR YYYQVGSDSK -GWSEIHSFI ARDIYSEETI A---FMFGDM GCATPYNTFI 274
GmPAP2    VLEGLKKGQR YYYKVGNDNG -GWSATGSFV SRNSDSDETI A---FLFGDM GTAVPYNTFL 277
ZmPAP2    LMKGLEPGRR YEYKVGSDTG -GWSEIYSFI SRDSEASETN A---FLFGDM GTYVPYNTYI 276
AtPAP15   RITGLKPSTI YYYRCGDESR RAMSKIHHFR TMEVSSPESY EGRIAVVGDL GSRLTYNTEE 201
Consensus XXXXLXXGXR YYYXVGXDXX -GWSXIXSFX XRXXXXXETX A---FXFGDM GXXXPYNTXX

AtPAP2    RTQDESISTV KWILRDIEAL GDKPAMISHI GDISYAR--- ---------- ---------- 311
BnPAP2    RTQDESISTV KWILRDIEAL GDKPALVSHI GDISYAR--- ---------- ---------- 311
GmPAP2    RTQDESISTM KWILRDVEAL GDKPAFVSHI GDISYAR--- ---------- ---------- 314
ZmPAP2    RTQSESESTV KWILRDIEAL GDKPAFISHI GDISYAR--- ---------- ---------- 313
AtPAP15   [illegible]ISHL [illegible] HNSPDLILLI GDVSYANLYL TNGTSSDCYS CSFPETPIHE 249
Consensus RTQXESISTX KWILRDXEAL GDKPAXXSHI GDISYAR--- ---------- ----------

AtPAP2    GYSWVWDEFF AQVEPIASTV PYHVCIGNHE YDESTQPWKP DWAASIYGND GGGECGVPYS 371
BnPAP2    GYSWVWDEFF AQIEPIASRV PYHVCIGNHE YDFPTQPWKP DWGT--YGND GGGECGVPYS 369
GmPAP2    GYSWLWDHFF AQIEPVASQV AYHVCIGNHE YDWPLQPWKP DWAS--YGKD GGGECGVPYS 372
ZmPAP2    GYSWVWYHFF SQIEPIAANT PYHVCIGNHE YDWPSQPWKP WWAT--YGTD GGGECGIPYS 370
AtPAP15   TYQPRWDYWG RFMENLTSKV PLMVIEGNHE IELQAE[illegible] [illegible]--[illegible] [illegible]NKIEEAYS 293
Consensus GYSWXWDXFF XQXEPXASXV PYHVCIGNHE YDXXXQPWKP XWXX--YGXD GGGECGXPYS

AtPAP2    LKFNMPGNSS ESTG-MKAPP TRNLYYSYDM GTVHFVYIST ETNFLKGGSQ YEFIKRDLES 430
BnPAP2    LKFNMPGNSS EPTG-TKAPP TRNLYYSYDM GSVHFLYIST ETNFLKGGRQ YEFIKRDLES 428
GmPAP2    LRFNMPGNSS ELTGNAAAPP TRNLYYSFDM GAVHFVYIST ETNFVPGSKQ YDFLKHDLES 432
ZmPAP2    VRFRMPGNSI LPTGN-GGPD TRNLYYSFDS GVVHFVYMST ETNFVQGSEQ HNFLKADLEK 429
AtPAP15   SRFAEPENES GSSS--[illegible] [illegible]LYYSFNA GGIHFVMLGA YIAYDKSAEQ YEWLKKDLAK 345
Consensus XXFXMPGNSS XXTGNXXXPX TRNLYYSXDX GXVHFVYXST ETNFXXGXXQ YXFXKXDLEX

AtPAP2    VDRKKTPFVV VQGHRPMYTT -SNEVRDTMI RQKMVEHLEP LEVKNNVTLA LWGHVHRYER 489
BnPAP2    VNREKTPFVV VQGHRPMYTT -SNEVRDAMI RQKMVEHLEP LEVENNVTLA LWGHVHRYER 487
GmPAP2    VNRSKTPFVV VQGHRPMYTT -SHENRDAAL RGKMLEHLEP LLVNNNVTLA LWGHVHRYER 491
ZmPAP2    VNRSRTPFVV EQGHRPMYTS -SDETRDAAL KQQMLQNLEP LLVTYNVTLA LWGHVHRYER 488
AtPAP15   VDRSVTPWLV ASWHRPWYSS YEAHYREA[illegible] EECMKEAMEE LLYSYGTDIV FNGHVHAYER 402
Consensus VXRXXTPFVV XQGHRPMYTX -SXEXRDAXX XXXMXEXLEP LXVXXNVTLA LWGHVHRYER

AtPAP2    FCPISNNT-- -CGTQW---- ---QGNPVHL VIGMAGQDWQ PIWQ------ --PRPNHPDE 531
BnPAP2    FCPISNNT-- -CGKQW---- ---RGSPVHL VIGMGGQDWQ PIWQ------ --PRPNHPGE 529
GmPAP2    FCPENNHT-- -CGVNAGHNA GDKNGYTVHI VIGMAGQDWQ PVWE------ --PRPDHPDD 540
ZmPAP2    FCPMQNSQ-- -CVNTE-SSS EQYSGAPVHL VIGMGGQDWQ PVWQ------ --PRPDHPDV 535
AtPAP15   SNRVYNYELD PCG[illegible]---- ---[illegible]PVYI VIGDGGNREK MAIEHADDEG KCPEPLTTPD 449
Consensus FCPXXNXX-- -CGXXX-XXX XXXXGXPVHX VIGMXGQDWQ PXWX------ --PRPXHPXX

AtPAP2    PIF------- ---------- PQPEQSMYRT GEFGYTRLVA NKEKLTV-SF VGNHDG--EV 571
BnPAP2    PIF------- ---------- PQPEQSMYRT GEFGYTRLVA NKEKLTV-SF VGNHDG--EV 569
GmPAP2    PIF------- ---------- PQPKWSLYRG GEFGYTRLVA TKQKLVL-SY VGNHDG--EV 580
ZmPAP2    PIF------- ---------- PQPERSMYRG GEFGYARLVA TREKLTL-TY VGNHDG--QV 575
AtPAP15   PVMGGECAWN ETESDKECWD KQPDYSAIRE SSFGHGILEM KNETWALWTW MKNQDSSSEV 609
Consensus PIF------- ---------- PQPXXSXYRX GEFGYXRLVA XXEKLXX-XX VGNHDG--EV

AtPAP2    HDTVEMLASG VVISGEKEST KIENLKTVPA SATLMGKS-- ESNALWYAKG AGLMVVGVLL 629
BnPAP2    HDSVEILASG EVISGRKEET ----IKTVPV SATLVGKP-- ESDVLWYVKG AGLLVMGVLL 623
GmPAP2    HDQLEILASG EVVSGDGGCS -----GEIAD ANEKAGNVIV ESTLSWYVKG GSVLLLGAEM 633
ZmPAP2    HDMVEIEASG EVSESNESVA -----EAVDQ TKLQTGVSTV RKIESELYLE GGSVMEALLL 629
AtPAP15   GDQIYIVRQP DRCPLHHREV -----[illegible] [illegible]-- [illegible] [illegible] 529
Consensus HDXXEIXXSG XVXXXXXXXX ----XXXXXX XXXXXGXXXV XXXXXXYXXX XXXXXXXXXX

AtPAP2    GFIIGFFTRG KK-ESSEGNR WIPVKNEETE 657
BnPAP2    GFLIGFFTRG KKGSSEEDNR WIPVKNEETE 653
GmPAP2    GYVEGMVTEA RKKREVPESN WIPVKIEETE 653
ZmPAP2    GFSEGILVRR KKEAAEE-EQ WTQVKNEESE 655
AtPAP15   [illegible] [illegible]-[illegible]-[illegible] [illegible]NHC[illegible] 533
Consensus GXXXGXXXXX XKXXXXXXXX WXXVKXEEXX
```

FIG. 4
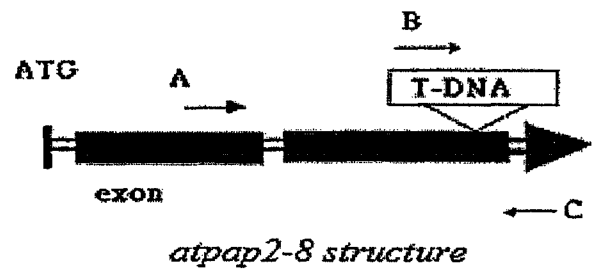
(a) Genomic PCR
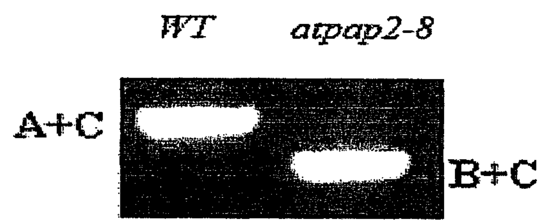
(b) RT-PCR
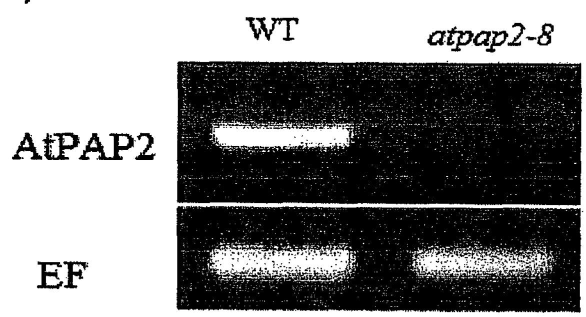
(c) Western blotting
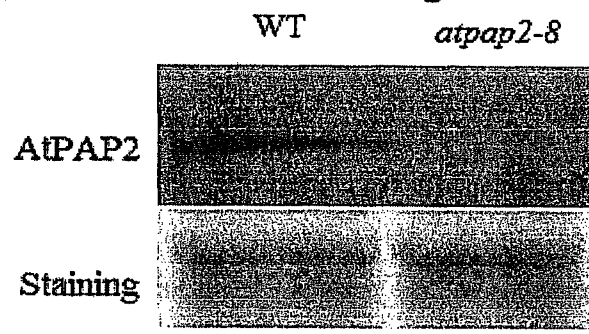

FIG. 6
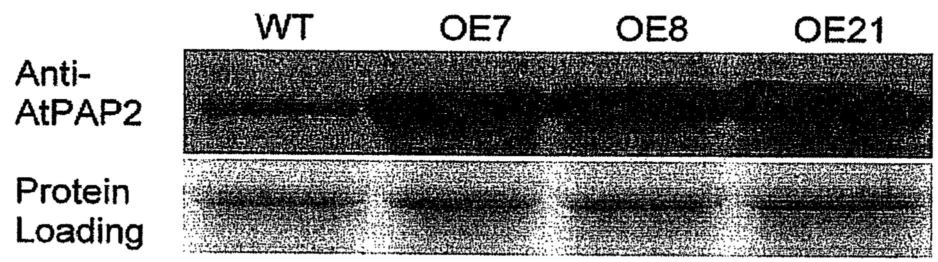
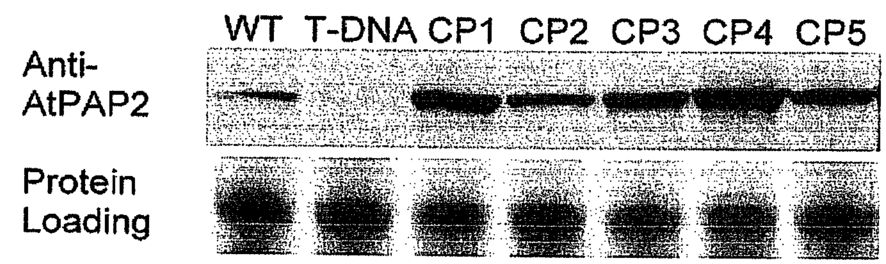
B
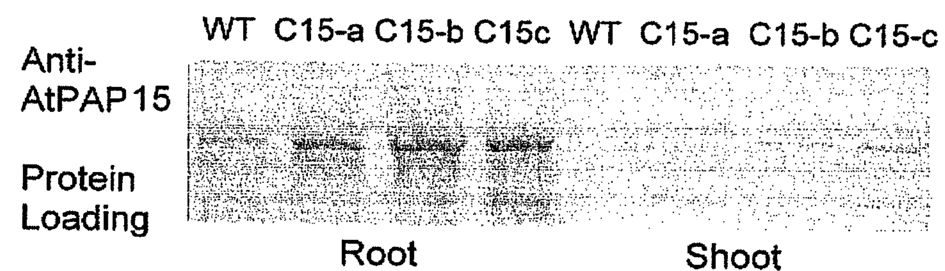

FIG. 7
(a)
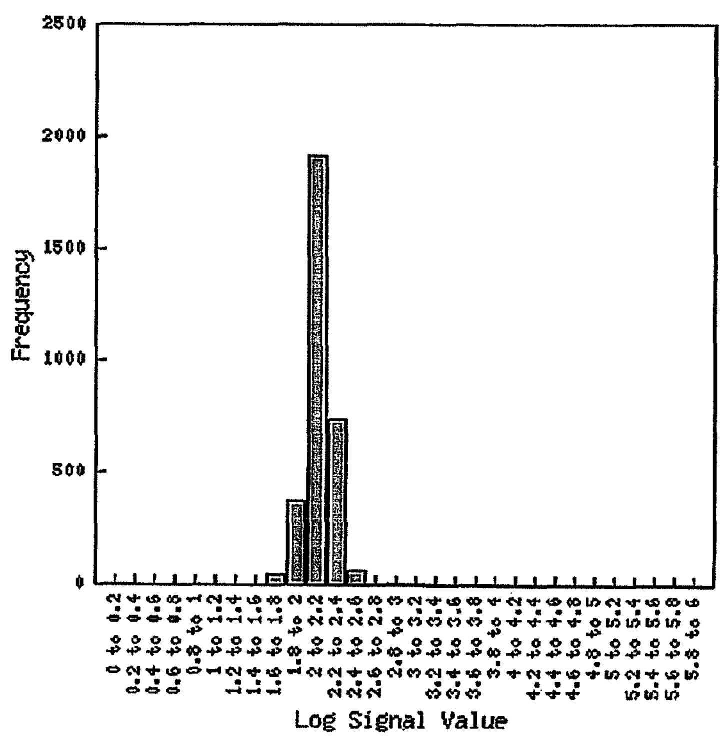
(b)
Leaf flower Stem Root Silique
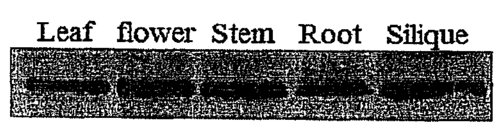
(c) Day after germination
Day 2 4 6 8 10
(d) Pi Suffcient Pi deficient Pi sufficient Pideficient
Leaf Stem Root Leaf Stem Root Root Stem Root Stem
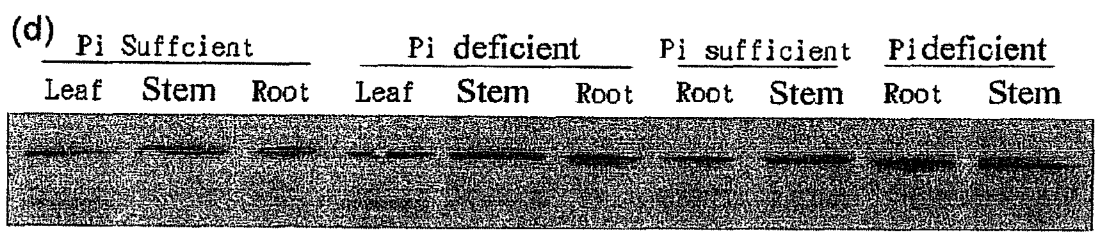

*Statistically ($p<0.001$) different from the WT ($n = 10$).

SEQUENCE LISTING

```
<160> NUMBER OF SEQ ID NOS: 67

<210> SEQ ID NO 1
<211> LENGTH: 1971
<212> TYPE: DNA
<213> ORGANISM: Arabidopsis thaliana

<400> SEQUENCE: 1

atgatcgtta atttctcttt cttcctcctt ctcttcgtct ccgtcttcgt ttcctctgct      60

gattctaaag cgaccatttc aatttcccct aatgctctca atcgatctgg cgattccgtt     120

gtgatacaat ggtccggtgt cgattctccg tcagatctcg attggttagg actctactcg     180

ccgccggagt ctcctaatga tcactttatt ggttacaaat tcctcaatga atcgtccact     240

tggaaagatg gtttcggttc gatttctctt cctttaacca atctccgatc aaattacaca     300

ttccggatct tccgttggag cgaatccgag attgatccga aacataagga tcatgatcag     360

aatcctttac caggaactaa acatcttcta gctgaatcgg agcagctgac tttcggatcc     420

ggtgttggta tgccggagca gatccatttg tcgttcacaa atatggttaa cacgatgcgt     480

gttatgtttg tagctggaga tggtgaagaa cgttttgtta gatacggtga atcgaaggat     540

ttgttaggta attccgcggc ggcgcgtggg atgaggtacg agagagagca catgtgtgat     600
```

```
tcgccggcga attccactat tggttggaga gatcctggtt ggatttttga taccgtcatg    660

aagaatttga atgatggcgt tagatactat tatcaggttg ggagtgattc taagggatgg    720

agtgagatcc atagctacat tgctcgagat gtgactgcag aagaaaccgt agctttcatg    780

tttggagata tgggttgtgc tacaccatac acgacattta tccgcacaca agatgagagc    840

atatctacag tgaagtggat cctccgtgac attgaagctc ttggtgataa gccagctatg    900

atttcacaca ttggagatat aagttatgct cgtggttact cgtgggtatg ggatgagttc    960

tttgctcagg ttgagcctat tgcctcgaca gttccttacc atgtttgcat tggtaaccat   1020

gagtatgatt tctctactca gccgtggaaa cctgattggg cagcttctat ttatggaaac   1080

gatggtggtg gcgaatgtgg tgtgccgtat agcttgaagt ttaacatgcc tgggaattct   1140

tcagagtcta caggaatgaa agctcctccg acaaggaatt tatattattc ttatgatatg   1200

ggaacggtcc atttcgttta tatctccaca gagacgaatt ttcttaaagg aggtagtcaa   1260

tatgaattca taaagcgaga tctagagtct gtagacagga agaaaacacc gtttgttgtt   1320

gtgcaaggac atagaccaat gtacactacg agcaacgagg ttagagacac tatgattcga   1380

caaaagatgg ttgagcatct agaacctttg tttgtgaaaa acaatgtcac acttgctcta   1440

tggggacatg ttcatagata cgaaaggttt tgtcccataa gcaacaacac ttgcggcaca   1500

cagtggcaag gaaatccggt tcatcttgtg atcggtatgg ctggtcaaga ttggcaaccg   1560

atttggcagc ctagaccaaa ccatccagat cttcctatat tccctcagcc tgaacaatca   1620

atgtatcgta caggtgagtt tggttacact cgtttagttg caaacaaaga aaagctcact   1680

gtttcttttg tgggtaatca cgatggcgaa gttcatgata ctgttgagat gttagcatct   1740

ggggtagtaa tcagtgggag caaagagagt actaaaatcc caaatctgaa aaccgttcct   1800

gcttctgcta cacttatggg aaaatcagaa tctaatgctt tgtggtatgc caaaggagca   1860

ggcttgatgg ttgtgggtgt gcttttaggg ttcattatcg ggtttttac ccggggaaag   1920

aaatcttcgt ctggaaaccg ttggatccca gtcaagaacg aggagacata a             1971
```

```
<210> SEQ ID NO 2
<211> LENGTH: 656
<212> TYPE: PRT
<213> ORGANISM: Arabidopsis thaliana

<400> SEQUENCE: 2

Met Ile Val Asn Phe Ser Phe Phe Leu Leu Leu Phe Val Ser Val Phe
1               5                   10                  15

Val Ser Ser Ala Asp Ser Lys Ala Thr Ile Ser Ile Ser Pro Asn Ala
            20                  25                  30

Leu Asn Arg Ser Gly Asp Ser Val Val Ile Gln Trp Ser Gly Val Asp
        35                  40                  45

Ser Pro Ser Asp Leu Asp Trp Leu Gly Leu Tyr Ser Pro Pro Glu Ser
    50                  55                  60

Pro Asn Asp His Phe Ile Gly Tyr Lys Phe Leu Asn Glu Ser Ser Thr
65                  70                  75                  80

Trp Lys Asp Gly Phe Gly Ser Ile Ser Leu Pro Leu Thr Asn Leu Arg
                85                  90                  95

Ser Asn Tyr Thr Phe Arg Ile Phe Arg Trp Ser Glu Ser Glu Ile Asp
            100                 105                 110

Pro Lys His Lys Asp His Asp Gln Asn Pro Leu Pro Gly Thr Lys His
        115                 120                 125
```

```
Leu Leu Ala Glu Ser Glu Gln Leu Thr Phe Gly Ser Gly Val Gly Met
    130                 135                 140

Pro Glu Gln Ile His Leu Ser Phe Thr Asn Met Val Asn Thr Met Arg
145                 150                 155                 160

Val Met Phe Val Ala Gly Asp Gly Glu Glu Arg Phe Val Arg Tyr Gly
                165                 170                 175

Glu Ser Lys Asp Leu Leu Gly Asn Ser Ala Ala Ala Arg Gly Met Arg
            180                 185                 190

Tyr Glu Arg Glu His Met Cys Asp Ser Pro Ala Asn Ser Thr Ile Gly
        195                 200                 205

Trp Arg Asp Pro Gly Trp Ile Phe Asp Thr Val Met Lys Asn Leu Asn
    210                 215                 220

Asp Gly Val Arg Tyr Tyr Tyr Gln Val Gly Ser Asp Ser Lys Gly Trp
225                 230                 235                 240

Ser Glu Ile His Ser Tyr Ile Ala Arg Asp Val Thr Ala Glu Glu Thr
                245                 250                 255

Val Ala Phe Met Phe Gly Asp Met Gly Cys Ala Thr Pro Tyr Thr Thr
            260                 265                 270

Phe Ile Arg Thr Gln Asp Glu Ser Ile Ser Thr Val Lys Trp Ile Leu
        275                 280                 285

Arg Asp Ile Glu Ala Leu Gly Asp Lys Pro Ala Met Ile Ser His Ile
    290                 295                 300

Gly Asp Ile Ser Tyr Ala Arg Gly Tyr Ser Trp Val Trp Asp Glu Phe
305                 310                 315                 320

Phe Ala Gln Val Glu Pro Ile Ala Ser Thr Val Pro Tyr His Val Cys
                325                 330                 335

Ile Gly Asn His Glu Tyr Asp Phe Ser Thr Gln Pro Trp Lys Pro Asp
            340                 345                 350

Trp Ala Ala Ser Ile Tyr Gly Asn Asp Gly Gly Gly Glu Cys Gly Val
        355                 360                 365

Pro Tyr Ser Leu Lys Phe Asn Met Pro Gly Asn Ser Ser Glu Ser Thr
    370                 375                 380

Gly Met Lys Ala Pro Pro Thr Arg Asn Leu Tyr Tyr Ser Tyr Asp Met
385                 390                 395                 400

Gly Thr Val His Phe Val Tyr Ile Ser Thr Glu Thr Asn Phe Leu Lys
                405                 410                 415

Gly Gly Ser Gln Tyr Glu Phe Ile Lys Arg Asp Leu Glu Ser Val Asp
            420                 425                 430

Arg Lys Lys Thr Pro Phe Val Val Val Gln Gly His Arg Pro Met Tyr
        435                 440                 445

Thr Thr Ser Asn Glu Val Arg Asp Thr Met Ile Arg Gln Lys Met Val
    450                 455                 460

Glu His Leu Glu Pro Leu Phe Val Lys Asn Asn Val Thr Leu Ala Leu
465                 470                 475                 480

Trp Gly His Val His Arg Tyr Glu Arg Phe Cys Pro Ile Ser Asn Asn
                485                 490                 495

Thr Cys Gly Thr Gln Trp Gln Gly Asn Pro Val His Leu Val Ile Gly
            500                 505                 510

Met Ala Gly Gln Asp Trp Gln Pro Ile Trp Gln Pro Arg Pro Asn His
        515                 520                 525

Pro Asp Leu Pro Ile Phe Pro Gln Pro Glu Gln Ser Met Tyr Arg Thr
    530                 535                 540

Gly Glu Phe Gly Tyr Thr Arg Leu Val Ala Asn Lys Glu Lys Leu Thr
```

-continued

```
545                 550                 555                 560

Val Ser Phe Val Gly Asn His Asp Gly Glu Val His Asp Thr Val Glu
                565                 570                 575

Met Leu Ala Ser Gly Val Val Ile Ser Gly Ser Lys Glu Ser Thr Lys
            580                 585                 590

Ile Pro Asn Leu Lys Thr Val Pro Ala Ser Ala Thr Leu Met Gly Lys
        595                 600                 605

Ser Glu Ser Asn Ala Leu Trp Tyr Ala Lys Gly Ala Gly Leu Met Val
    610                 615                 620

Val Gly Val Leu Leu Gly Phe Ile Ile Gly Phe Phe Thr Arg Gly Lys
625                 630                 635                 640

Lys Ser Ser Ser Gly Asn Arg Trp Ile Pro Val Lys Asn Glu Glu Thr
                645                 650                 655


<210> SEQ ID NO 3
<211> LENGTH: 1956
<212> TYPE: DNA
<213> ORGANISM: Arabidopsis thaliana

<400> SEQUENCE: 3

atgatcgccg ccgtttacac tctcttcttc ttcttcctct taatctcctc tgtttattcc      60

aaagccacga tttcaatctc tccccaaacc ttaaaccgat ccggcgacat agtcgtgatc     120

aaatggtccg gcgtcgaatc accgtccgat ctcgactggt taggaatcta ctcgccaccg     180

gactctcctc acgatcactt catcggctac aaattcctct ccgattcacc cacgtggcaa     240

tccgggtcgg gttcgatttc acttccctta accaatctcc gatcaaatta cactttccgg     300

atctttcatt ggacccaatc cgaaataaac ccgaaacacc aagaccatga tcacaatcct     360

ttacccggaa ctcgtcatct cttaaccgaa tcaaaccagt taaatttccg gttcgctgtt     420

aaccgaccgg agcagattca tttaagttac acagataaca tcaacgagat gagagtagtg     480

tttgtaaccg gagatggaga agaacgagaa gctcgctacg gtgaggttaa ggacaagctc     540

gataacatag cggtggcgcg tggagttagg tacgagatag aacatatgtg tcacgcgccg     600

gcgaattcta cagtcggatg gagagatcca ggttggacat tcgatgccgt gatgaagaat     660

ctaaaacaag ggattaggta ttattatcag gttgggagtg atttaaaagg atggagtgag     720

attcatagct ttgtttctcg aaatgagggt tcagaagaaa cattagcttt catgtttggt     780

gatatgggat gttatacacc ttatacaaca tttatccgtg gagaagaaga aagtttatca     840

actgtgaaat ggattttaag agacattgaa gctttaggtg atgataagcc tgtgattgta     900

tcacatatcg gagatataag ttatgcacga ggttactcgt ggatttggga tgagttcttt     960

actcagattg agcctattgc ttctaaagtg ccttaccatg tatgtattgg taaccatgag    1020

tatgattggc ctaaccagcc ttggaaacca gattgggctg cttatgttta tggtaaagat    1080

agtggtggtg aatgtggtgt accgtatagt gttaagttca acatgcctgg taattcaacg    1140

gaagctactg gtatggttaa gggacctcaa agtcggaacc tttactattc ttatgatatg    1200

ggttctgttc atttcgttta tatttcgaca gagactgatt ttcttaaagg tgggaagcag    1260

tatagttttt tgaagagtga tttggagtct gttaatagga gtaagacacc gtttgttgtt    1320

gtccaagggc atagacctat gtacactacg agtaggaaga tcagagacgc tgctataaga    1380

gagaagatga tcgagcattt ggaaccgttg ttagtgaaga acaatgtgac ggttgcttta    1440

tggggacatg tacatagata tgaaaggttt tgtgcgatta gtaacaatac ttgtggtgaa    1500

cgttggcaag gaaatccagt tcatcttgtg attggtatgg ctggaaaaga ctcacaaccg    1560
```

```
atgtgggaac cgagagctaa tcacgaggat gtcccgatct ttcctcagcc tgctaactca   1620

atgtaccgtg gaggcgagtt tgggtacatt cgtttggttg ctaataagga aagacttact   1680

ctttcttatg tgggaaacca tgacggagaa gttcatgatg ttgttgagat tttggcttct   1740

ggggaagtta ttagcggtag tgatgatggt actaaagact caaactttgg atcagaatct   1800

gactttgcag tcttgtggta cattgaagga gcaagtgtga tggttgtggg agtgattttt   1860

gggtactttg tcggttttct tagtcgtaaa aagaaagaat ctggagttgg atcatctaat   1920

cgtagttgga tccaagtgaa aaacgaggag acatga                              1956
```

<210> SEQ ID NO 4
<211> LENGTH: 651
<212> TYPE: PRT
<213> ORGANISM: Arabidopsis thaliana

<400> SEQUENCE: 4

```
Met Ile Ala Ala Val Tyr Thr Leu Phe Phe Phe Phe Leu Leu Ile Ser
1               5                   10                  15

Ser Val Tyr Ser Lys Ala Thr Ile Ser Ile Ser Pro Gln Thr Leu Asn
            20                  25                  30

Arg Ser Gly Asp Ile Val Val Ile Lys Trp Ser Gly Val Glu Ser Pro
        35                  40                  45

Ser Asp Leu Asp Trp Leu Gly Ile Tyr Ser Pro Pro Asp Ser Pro His
    50                  55                  60

Asp His Phe Ile Gly Tyr Lys Phe Leu Ser Asp Ser Pro Thr Trp Gln
65                  70                  75                  80

Ser Gly Ser Gly Ser Ile Ser Leu Pro Leu Thr Asn Leu Arg Ser Asn
                85                  90                  95

Tyr Thr Phe Arg Ile Phe His Trp Thr Gln Ser Glu Ile Asn Pro Lys
            100                 105                 110

His Gln Asp His Asp His Asn Pro Leu Pro Gly Thr Arg His Leu Leu
        115                 120                 125

Thr Glu Ser Asn Gln Leu Asn Phe Arg Phe Ala Val Asn Arg Pro Glu
    130                 135                 140

Gln Ile His Leu Ser Tyr Thr Asp Asn Ile Asn Glu Met Arg Val Val
145                 150                 155                 160

Phe Val Thr Gly Asp Gly Glu Glu Arg Glu Ala Arg Tyr Gly Glu Val
                165                 170                 175

Lys Asp Lys Leu Asp Asn Ile Ala Val Ala Arg Gly Val Arg Tyr Glu
            180                 185                 190

Ile Glu His Met Cys His Ala Pro Ala Asn Ser Thr Val Gly Trp Arg
        195                 200                 205

Asp Pro Gly Trp Thr Phe Asp Ala Val Met Lys Asn Leu Lys Gln Gly
    210                 215                 220

Ile Arg Tyr Tyr Tyr Gln Val Gly Ser Asp Leu Lys Gly Trp Ser Glu
225                 230                 235                 240

Ile His Ser Phe Val Ser Arg Asn Glu Gly Ser Glu Glu Thr Leu Ala
                245                 250                 255

Phe Met Phe Gly Asp Met Gly Cys Tyr Thr Pro Tyr Thr Thr Phe Ile
            260                 265                 270

Arg Gly Glu Glu Glu Ser Leu Ser Thr Val Lys Trp Ile Leu Arg Asp
        275                 280                 285

Ile Glu Ala Leu Gly Asp Asp Lys Pro Val Ile Val Ser His Ile Gly
    290                 295                 300
```

```
Asp Ile Ser Tyr Ala Arg Gly Tyr Ser Trp Ile Trp Asp Glu Phe Phe
305                 310                 315                 320

Thr Gln Ile Glu Pro Ile Ala Ser Lys Val Pro Tyr His Val Cys Ile
                325                 330                 335

Gly Asn His Glu Tyr Asp Trp Pro Asn Gln Pro Trp Lys Pro Asp Trp
            340                 345                 350

Ala Ala Tyr Val Tyr Gly Lys Asp Ser Gly Gly Glu Cys Gly Val Pro
        355                 360                 365

Tyr Ser Val Lys Phe Asn Met Pro Gly Asn Ser Thr Glu Ala Thr Gly
    370                 375                 380

Met Val Lys Gly Pro Gln Ser Arg Asn Leu Tyr Tyr Ser Tyr Asp Met
385                 390                 395                 400

Gly Ser Val His Phe Val Tyr Ile Ser Thr Glu Thr Asp Phe Leu Lys
                405                 410                 415

Gly Gly Lys Gln Tyr Ser Phe Leu Lys Ser Asp Leu Glu Ser Val Asn
            420                 425                 430

Arg Ser Lys Thr Pro Phe Val Val Val Gln Gly His Arg Pro Met Tyr
        435                 440                 445

Thr Thr Ser Arg Lys Ile Arg Asp Ala Ala Ile Arg Glu Lys Met Ile
    450                 455                 460

Glu His Leu Glu Pro Leu Leu Val Lys Asn Asn Val Thr Val Ala Leu
465                 470                 475                 480

Trp Gly His Val His Arg Tyr Glu Arg Phe Cys Ala Ile Ser Asn Asn
                485                 490                 495

Thr Cys Gly Glu Arg Trp Gln Gly Asn Pro Val His Leu Val Ile Gly
            500                 505                 510

Met Ala Gly Lys Asp Ser Gln Pro Met Trp Glu Pro Arg Ala Asn His
        515                 520                 525

Glu Asp Val Pro Ile Phe Pro Gln Pro Ala Asn Ser Met Tyr Arg Gly
    530                 535                 540

Gly Glu Phe Gly Tyr Ile Arg Leu Val Ala Asn Lys Glu Arg Leu Thr
545                 550                 555                 560

Leu Ser Tyr Val Gly Asn His Asp Gly Glu Val His Asp Val Val Glu
                565                 570                 575

Ile Leu Ala Ser Gly Glu Val Ile Ser Gly Ser Asp Asp Gly Thr Lys
            580                 585                 590

Asp Ser Asn Phe Gly Ser Glu Ser Asp Phe Ala Val Leu Trp Tyr Ile
        595                 600                 605

Glu Gly Ala Ser Val Met Val Val Gly Val Ile Phe Gly Tyr Phe Val
    610                 615                 620

Gly Phe Leu Ser Arg Lys Lys Lys Glu Ser Gly Val Gly Ser Ser Asn
625                 630                 635                 640

Arg Ser Trp Ile Gln Val Lys Asn Glu Glu Thr
                645                 650
```

<210> SEQ ID NO 5
<211> LENGTH: 1989
<212> TYPE: DNA
<213> ORGANISM: Glycine max

<400> SEQUENCE: 5

```
atgattcccg atctacccct cccccttcctc ttctccttat tcatcatctt cttccacctc      60

gctgaatcca aaccctccct caccgccacg ccaaccaccc tcccagcctc cggcgccacc     120
```

```
gtcaatctcc gctggtccgg catcccttcc ccctccgacc tcgacttcct cgccatctat    180

tcccctccga cctccccgca cgacaacttc atcggatacc tcttcctctc gcagtccgcc    240

acgtggcgca ccggctccgg caacctctcc ctccccctcg tcgacctccg ctccaactac    300

tccttccgca tcttcagctg gacccgcgcc gagatcaacc ccaagcgcca ggaccacgat    360

cacaaccctc tcccggtcac acgccacctc ctcgcgtttt cggaggaggt ctccttcgcc    420

cctcaccgtg ggccccaaca gatccacctg gcgttcgttg gggcccacgg caaggaggag    480

gatatgcgcg tgatgtacat cgcgcgcgat ccgagagaaa cctacgtaag gtacggggag    540

agggaggata agcttgatgg gattgcggtc gcacgtgtgg agaggtacga gagggagcac    600

atgtgcgacg cgcctgccaa cacgagtgtt gggtggaggg accctgggtt tatcaacgac    660

gccgttctca taggtttgaa gaagggacag aggtattatt acaaggttgg aaatgataac    720

ggaggttgga gtgcaactca aagttttgtg tcgaggaata gtgattcaga cgaaacaata    780

gctttcctgt ttggtgacat gggaacagct gtaccataca atacgtttct gcgaacgcag    840

gatgaaagca tatcaaccat gaagtggatc ctccgtgatg ttgaagctct aggcgacaag    900

ccagcctttg tgtcgcacat tggagacatt agttatgcaa gaggttattc ctggttgtgg    960

gaccattttt ttgcccagat tgaacctgtt gcctcccaag tggcatacca tgtttgcatt   1020

ggcaatcatg agtatgactg gcctttgcag ccatggaaac ctgattgggc cagttatgga   1080

aaagatgggg gtggtgagtg tggtgtgcct tacagtttaa ggtttaacat gcccggaaac   1140

tcttcagaac tcactggaaa tgctgcagcc ccaccaacta ggaatcttta ttactcattt   1200

gatatgggag cagtacactt tgtgtatatt tccacggaga ccaattttgt tcctgggagc   1260

aaacagtacg acttcttgaa gcatgatttg gaatcggtta acaggagcaa gactcctttt   1320

gtggtggtgc aagggcacag gcccatgtac actaccagcc atgaaaatag ggatgctgct   1380

ttaagaggaa agatgcttga gcacttggaa cctctgttgg tgaataacaa tgtgacactt   1440

gccctttggg gtcatgttca tagatacgag agattttgtc cactgaataa cttcacttgt   1500

ggtgttaatg cgggtcacaa tgcaggggac aaaaaaggat atactgttca cattgtgatc   1560

ggcatggcag ggcaagactg gcaacctgtc tgggaaccaa ggccagacca tcccgatgat   1620

ccaatctttc cacagccaaa atggtctctg taccgcggag gcgagtttgg gtacacaaga   1680

ctcgtcgcta caaagcagaa gctcgtgctt tcttatgtgg gaaaccatga cggtgaggtg   1740

catgatcagt tggaaattct ggcatctggg gaagttgtca gtggtgacgg aggctgtagt   1800

attgctgatg ctaattctaa agctggaaat gtgattgtgg aatccacatt gtcttggtat   1860

gtcaagggag gaagtgtgct gctgcttggt gcattcatgg gttacgtttt tggttacgtt   1920

acaagtgcaa ggaagaagtc tgaggtgcca gagagcaatt ggactccggt gaagactgag   1980

gaaacttga                                                           1989
```

```
<210> SEQ ID NO 6
<211> LENGTH: 662
<212> TYPE: PRT
<213> ORGANISM: Glycine max

<400> SEQUENCE: 6

Met Ile Pro Asp Leu Pro Leu Pro Phe Leu Phe Ser Leu Phe Ile Ile
1               5                   10                  15

Phe Phe His Leu Ala Glu Ser Lys Pro Ser Leu Thr Ala Thr Pro Thr
            20                  25                  30

Thr Leu Pro Ala Ser Gly Ala Thr Val Asn Leu Arg Trp Ser Gly Ile
```

-continued

```
        35                  40                  45

Pro Ser Pro Ser Asp Leu Asp Phe Leu Ala Ile Tyr Ser Pro Pro Thr
    50                  55                  60

Ser Pro His Asp Asn Phe Ile Gly Tyr Leu Phe Leu Ser Gln Ser Ala
65                  70                  75                  80

Thr Trp Arg Thr Gly Ser Gly Asn Leu Ser Leu Pro Leu Val Asp Leu
                85                  90                  95

Arg Ser Asn Tyr Ser Phe Arg Ile Phe Ser Trp Thr Arg Ala Glu Ile
            100                 105                 110

Asn Pro Lys Arg Gln Asp His Asp His Asn Pro Leu Pro Val Thr Arg
        115                 120                 125

His Leu Leu Ala Phe Ser Glu Glu Val Ser Phe Ala Pro His Arg Gly
    130                 135                 140

Pro Gln Gln Ile His Leu Ala Phe Val Gly Ala His Gly Lys Glu Glu
145                 150                 155                 160

Asp Met Arg Val Met Tyr Ile Ala Arg Asp Pro Arg Glu Thr Tyr Val
                165                 170                 175

Arg Tyr Gly Glu Arg Glu Asp Lys Leu Asp Gly Ile Ala Val Ala Arg
            180                 185                 190

Val Glu Arg Tyr Glu Arg Glu His Met Cys Asp Ala Pro Ala Asn Thr
        195                 200                 205

Ser Val Gly Trp Arg Asp Pro Gly Phe Ile Asn Asp Ala Val Leu Ile
    210                 215                 220

Gly Leu Lys Lys Gly Gln Arg Tyr Tyr Tyr Lys Val Gly Asn Asp Asn
225                 230                 235                 240

Gly Gly Trp Ser Ala Thr Gln Ser Phe Val Ser Arg Asn Ser Asp Ser
                245                 250                 255

Asp Glu Thr Ile Ala Phe Leu Phe Gly Asp Met Gly Thr Ala Val Pro
            260                 265                 270

Tyr Asn Thr Phe Leu Arg Thr Gln Asp Glu Ser Ile Ser Thr Met Lys
        275                 280                 285

Trp Ile Leu Arg Asp Val Glu Ala Leu Gly Asp Lys Pro Ala Phe Val
    290                 295                 300

Ser His Ile Gly Asp Ile Ser Tyr Ala Arg Gly Tyr Ser Trp Leu Trp
305                 310                 315                 320

Asp His Phe Phe Ala Gln Ile Glu Pro Val Ala Ser Gln Val Ala Tyr
                325                 330                 335

His Val Cys Ile Gly Asn His Glu Tyr Asp Trp Pro Leu Gln Pro Trp
            340                 345                 350

Lys Pro Asp Trp Ala Ser Tyr Gly Lys Asp Gly Gly Gly Glu Cys Gly
        355                 360                 365

Val Pro Tyr Ser Leu Arg Phe Asn Met Pro Gly Asn Ser Ser Glu Leu
    370                 375                 380

Thr Gly Asn Ala Ala Ala Pro Pro Thr Arg Asn Leu Tyr Tyr Ser Phe
385                 390                 395                 400

Asp Met Gly Ala Val His Phe Val Tyr Ile Ser Thr Glu Thr Asn Phe
                405                 410                 415

Val Pro Gly Ser Lys Gln Tyr Asp Phe Leu Lys His Asp Leu Glu Ser
            420                 425                 430

Val Asn Arg Ser Lys Thr Pro Phe Val Val Val Gln Gly His Arg Pro
        435                 440                 445

Met Tyr Thr Thr Ser His Glu Asn Arg Asp Ala Ala Leu Arg Gly Lys
    450                 455                 460
```

```
Met Leu Glu His Leu Glu Pro Leu Leu Val Asn Asn Asn Val Thr Leu
465                 470                 475                 480

Ala Leu Trp Gly His Val His Arg Tyr Glu Arg Phe Cys Pro Leu Asn
                485                 490                 495

Asn Phe Thr Cys Gly Val Asn Ala Gly His Asn Ala Gly Asp Lys Lys
            500                 505                 510

Gly Tyr Thr Val His Ile Val Ile Gly Met Ala Gly Gln Asp Trp Gln
        515                 520                 525

Pro Val Trp Glu Pro Arg Pro Asp His Pro Asp Asp Pro Ile Phe Pro
    530                 535                 540

Gln Pro Lys Trp Ser Leu Tyr Arg Gly Gly Glu Phe Gly Tyr Thr Arg
545                 550                 555                 560

Leu Val Ala Thr Lys Gln Lys Leu Val Leu Ser Tyr Val Gly Asn His
                565                 570                 575

Asp Gly Glu Val His Asp Gln Leu Glu Ile Leu Ala Ser Gly Glu Val
            580                 585                 590

Val Ser Gly Asp Gly Gly Cys Ser Ile Ala Asp Ala Asn Ser Lys Ala
        595                 600                 605

Gly Asn Val Ile Val Glu Ser Thr Leu Ser Trp Tyr Val Lys Gly Gly
    610                 615                 620

Ser Val Leu Leu Leu Gly Ala Phe Met Gly Tyr Val Phe Gly Tyr Val
625                 630                 635                 640

Thr Ser Ala Arg Lys Lys Ser Glu Val Pro Glu Ser Asn Trp Thr Pro
                645                 650                 655

Val Lys Thr Glu Glu Thr
            660
```

<210> SEQ ID NO 7
<211> LENGTH: 1965
<212> TYPE: DNA
<213> ORGANISM: Zea mays

<400> SEQUENCE: 7

```
atgtaccccg aaaaccccca cctccgcttc ctcctcttcc tcgccgtcgc ggcagttgcc      60

gccggcgggg ctgcggcgaa caccaccctc accgcgtccc tctccggcaa ccagatcaag     120

atcatctggt ccggactccc ggccccggac ggcctcgact acgttgccat ctactcgccg     180

ccgtcctccc tcgaccgcga cttcctcggc tatctcttcc tcaacggctc cgcctcctgg     240

cgcggcggct ccggggagct ctccctcccg ctcctcccga cgctccgcgc gccctaccag     300

ttccgtctct ttcgctggcc cgccaaggag tactcctacc accacgtcga ccacgaccag     360

aacccgctcc cccacggcaa gcaccgcgtc gccgtctccg ccgacgtctc cgtcggcgac     420

cccgcccgcc ccgagcagct gcacctcgcg tttgcggatg aggtcgacga gatgcgggtc     480

ctgttcgtgt gcggcgaccg cggggagagg gtcgtcaggt acgggctgca gaaggaggac     540

gacaaggagt ggaaggaggt gggcacggat gtgagcacgt acgagcagag gcacatgtgc     600

gattggccgg ccaacagcag cgtcgcctgg agggatccgg gattcgtctt cgacggcctc     660

atgaagggat tggagcccgg aaggaggtac ttttacaagg ttggtagtga cacaggagga     720

tggagtgaga tatacagctt catttcacgt gacagtgaag ccagtgagac caatgctttt     780

ctatttggtg acatgggaac ttatgtgcct tataacacct acattcgcac acaatctgag     840

agcttgtcca ctgtaaagtg gatccttcgt gatattgaag cccttggaga taaacccgcc     900

tttatttcac acattgggga catcagctat gctagaggtt attcttgggt ctggtatcat     960
```

```
ttcttcagcc agatcgagcc tattgctgcc aatactccat accatgtctg tataggaaat   1020

catgagtatg attggccatc acaaccctgg aaaccatggt gggctacata tggaacggac   1080

ggtggaggcg aatgtggaat accttatagt gtcaggttca gaatgccagg caattctatt   1140

ctacctacag gtaatggtgg cccagacacc aggaatcttt attactcctt cgactcaggc   1200

gtggtgcatt tcgtctacat gtcgaccgaa acaaattttg ttcagggaag tgagcagcac   1260

aacttcttga aagcggacct tgagaaggtg aaccgaagta gaacaccctt tgttgttttt   1320

cagggccacc gccccatgta cacctcgagc gatgaaacca gggacgcggc tttgaaacag   1380

cagatgctcc agaatctgga accgctgctg gtgacataca atgtgaccct cgcgctatgg   1440

ggacatgtcc acaggtacga gaggttctgc ccgatgcaga attcccaatg tgtcaacact   1500

tcatcaagct tccagtactc tggcgctcct gtgcatcttg tgatcgggat gggcggccaa   1560

gactggcaac ctgtatggca accgaggcct gatcacccag acgtccctat ctttcctcag   1620

cctgagcgtt ccatgtaccg cggtggcgag tttggatacg ccagacttgt ggcaacaagg   1680

gagaagctaa cattgactta tgtggggaac catgatgggc aggtccatga tatggtggag   1740

atattttctg gcctggtatc cccagtaac agtagtgttg ctgaggcggt ggatggaacc   1800

aaacttggca caggagtcag caccgtgcgg aaaatttctc cgctgtactt ggaaattgga   1860

ggcagtgtga tgtttgcgct gctcctggga ttttcctttg ggatacttgt caggagaaag   1920

aaagaagctg cacagtggac tcaagtaaag aatgaggaat cgtag                   1965
```

```
<210> SEQ ID NO 8
<211> LENGTH: 654
<212> TYPE: PRT
<213> ORGANISM: Zea mays

<400> SEQUENCE: 8

Met Tyr Pro Glu Asn Pro His Leu Arg Phe Leu Leu Phe Leu Ala Val
1               5                   10                  15

Ala Ala Val Ala Ala Gly Gly Ala Ala Ala Asn Thr Thr Leu Thr Ala
            20                  25                  30

Ser Leu Ser Gly Asn Gln Ile Lys Ile Ile Trp Ser Gly Leu Pro Ala
        35                  40                  45

Pro Asp Gly Leu Asp Tyr Val Ala Ile Tyr Ser Pro Pro Ser Ser Leu
    50                  55                  60

Asp Arg Asp Phe Leu Gly Tyr Leu Phe Leu Asn Gly Ser Ala Ser Trp
65                  70                  75                  80

Arg Gly Gly Ser Gly Glu Leu Ser Leu Pro Leu Leu Pro Thr Leu Arg
                85                  90                  95

Ala Pro Tyr Gln Phe Arg Leu Phe Arg Trp Pro Ala Lys Glu Tyr Ser
            100                 105                 110

Tyr His His Val Asp His Asp Gln Asn Pro Leu Pro His Gly Lys His
        115                 120                 125

Arg Val Ala Val Ser Ala Asp Val Ser Val Gly Asp Pro Ala Arg Pro
    130                 135                 140

Glu Gln Leu His Leu Ala Phe Ala Asp Glu Val Asp Glu Met Arg Val
145                 150                 155                 160

Leu Phe Val Cys Gly Asp Arg Gly Glu Arg Val Val Arg Tyr Gly Leu
                165                 170                 175

Gln Lys Glu Asp Asp Lys Glu Trp Lys Glu Val Gly Thr Asp Val Ser
            180                 185                 190
```

-continued

```
Thr Tyr Glu Gln Arg His Met Cys Asp Trp Pro Ala Asn Ser Ser Val
        195                 200                 205

Ala Trp Arg Asp Pro Gly Phe Val Phe Asp Gly Leu Met Lys Gly Leu
    210                 215                 220

Glu Pro Gly Arg Arg Tyr Phe Tyr Lys Val Gly Ser Asp Thr Gly Gly
225                 230                 235                 240

Trp Ser Glu Ile Tyr Ser Phe Ile Ser Arg Asp Ser Glu Ala Ser Glu
                245                 250                 255

Thr Asn Ala Phe Leu Phe Gly Asp Met Gly Thr Tyr Val Pro Tyr Asn
            260                 265                 270

Thr Tyr Ile Arg Thr Gln Ser Glu Ser Leu Ser Thr Val Lys Trp Ile
        275                 280                 285

Leu Arg Asp Ile Glu Ala Leu Gly Asp Lys Pro Ala Phe Ile Ser His
    290                 295                 300

Ile Gly Asp Ile Ser Tyr Ala Arg Gly Tyr Ser Trp Val Trp Tyr His
305                 310                 315                 320

Phe Phe Ser Gln Ile Glu Pro Ile Ala Ala Asn Thr Pro Tyr His Val
                325                 330                 335

Cys Ile Gly Asn His Glu Tyr Asp Trp Pro Ser Gln Pro Trp Lys Pro
            340                 345                 350

Trp Trp Ala Thr Tyr Gly Thr Asp Gly Gly Gly Glu Cys Gly Ile Pro
        355                 360                 365

Tyr Ser Val Arg Phe Arg Met Pro Gly Asn Ser Ile Leu Pro Thr Gly
    370                 375                 380

Asn Gly Gly Pro Asp Thr Arg Asn Leu Tyr Tyr Ser Phe Asp Ser Gly
385                 390                 395                 400

Val Val His Phe Val Tyr Met Ser Thr Glu Thr Asn Phe Val Gln Gly
                405                 410                 415

Ser Glu Gln His Asn Phe Leu Lys Ala Asp Leu Glu Lys Val Asn Arg
            420                 425                 430

Ser Arg Thr Pro Phe Val Val Phe Gln Gly His Arg Pro Met Tyr Thr
        435                 440                 445

Ser Ser Asp Glu Thr Arg Asp Ala Ala Leu Lys Gln Gln Met Leu Gln
    450                 455                 460

Asn Leu Glu Pro Leu Leu Val Thr Tyr Asn Val Thr Leu Ala Leu Trp
465                 470                 475                 480

Gly His Val His Arg Tyr Glu Arg Phe Cys Pro Met Gln Asn Ser Gln
                485                 490                 495

Cys Val Asn Thr Ser Ser Ser Phe Gln Tyr Ser Gly Ala Pro Val His
            500                 505                 510

Leu Val Ile Gly Met Gly Gly Gln Asp Trp Gln Pro Val Trp Gln Pro
        515                 520                 525

Arg Pro Asp His Pro Asp Val Pro Ile Phe Pro Gln Pro Glu Arg Ser
    530                 535                 540

Met Tyr Arg Gly Gly Glu Phe Gly Tyr Ala Arg Leu Val Ala Thr Arg
545                 550                 555                 560

Glu Lys Leu Thr Leu Thr Tyr Val Gly Asn His Asp Gly Gln Val His
                565                 570                 575

Asp Met Val Glu Ile Phe Ser Gly Leu Val Ser Pro Ser Asn Ser Ser
            580                 585                 590

Val Ala Glu Ala Val Asp Gly Thr Lys Leu Gly Thr Gly Val Ser Thr
        595                 600                 605

Val Arg Lys Ile Ser Pro Leu Tyr Leu Glu Ile Gly Gly Ser Val Met
```

```
    610                 615                 620

Phe Ala Leu Leu Leu Gly Phe Ser Phe Gly Ile Leu Val Arg Arg Lys
625                 630                 635                 640

Lys Glu Ala Ala Gln Trp Thr Gln Val Lys Asn Glu Glu Ser
                645                 650


<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9

tggttcacgt agtgggccat cg                                              22


<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10

ttgaagttta acatgcctgg g                                               21


<210> SEQ ID NO 11
<211> LENGTH: 21
<212> TYPE: DNA
<213> ORGANISM: Artificial sequence
<220> FEATURE:
<223> OTHER INFORMATION: Synthetic primer

<400> SEQUENCE: 11

tccaatgctc gattgattag c                                               21


<210> SEQ ID NO 12
<211> LENGTH: 31
<212> TYPE: DNA
<213> ORGANISM: Artificial Sequence
<220> FEATURE:
<223> OTHER INFORMATION: Synthetic primer

<400> SEQUENCE: 12

ggccgtcgac atgatcgtta atttctcttt c                                    31


<210> SEQ ID NO 13
<211> LENGTH: 31
<212> TYPE: DNA
<213> ORGANISM: Artificial Sequence
<220> FEATURE:
<223> OTHER INFORMATION: Synthetic primer

<400> SEQUENCE: 13

ccggactagt tcatgtctcc tcgttcttga c                                    31


<210> SEQ ID NO 14
<211> LENGTH: 27
<212> TYPE: DNA
<213> ORGANISM: Artificial Sequence
<220> FEATURE:
<223> OTHER INFORMATION: Synthetic primer

<400> SEQUENCE: 14

gtttcacatc aacattgtgg tcattgg                                         27
```

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
gagtacttgg gggtagtggc atcc 24

<210> SEQ ID NO 16
<211> LENGTH: 30
<212> TYPE: DNA
<213> ORGANISM: Artificial Sequence
<220> FEATURE:
<223> OTHER INFORMATION: Synthetic primer

<400> SEQUENCE: 16
ggttgagctc gattctaaag cgaccatttc 30

<210> SEQ ID NO 17
<211> LENGTH: 29
<212> TYPE: DNA
<213> ORGANISM: Artificial Sequence
<220> FEATURE:
<223> OTHER INFORMATION: Synthetic primer

<400> SEQUENCE: 17
ttttggtacc tcaggatccg aaagtcagc 29

<210> SEQ ID NO 18
<211> LENGTH: 1959
<212> TYPE: DNA
<213> ORGANISM: Brassica rapa

<400> SEQUENCE: 18
atgatcgtcg agttctctac cttcatcctc ttcctctccg tcttcgtctc ctcagctaac 60
gccaaagcaa ccttatccat ctcccccaaa actctaagcc gatccggcga ttccatcctc 120
atcaaatggt ccaacctcga ctctccctcc gatctcgact ggctaggcat ctactccccc 180
ccagcctctc cccacgacca cttcatcggc tacaagttcc tcaacgcctc ccccacgtgg 240
caatccggct ccggcgcgat ctccctcccc ctcaccaacc tccgatcgaa ctacacgttc 300
cgtatcttcc gatggacgca gtccgagatc aatccgaagc acaaggacca cgaccagaat 360
cccttaccgg gaacgaagca ccttctggcg gaatcggagc aggtggggtt cggatccgcc 420
ggcgtgggga ggccggagca gatccatttg gcgttcgagg ataaggttaa caggatgcag 480
gtcacgttcg tagctgggga tggggaagaa aggttcgtga ggtacggaga ggcggaggat 540
gcgttggcga actccgcggc ggcgcgcggg attaggtacg agagggagca tatgtgtaat 600
gctccggcta attccaccgt gggatggaga gatcccgggt ggatttttca taccgttatg 660
aagaatttga acggtggcgt taggtattat tatcaggttg ggagtgattc aaagggatgg 720
agtgagatcc acagcttcat cgctcgagat atctactcag aagaaaccat agctttcatg 780
ttcggagaca tgggttgcgc tacaccttac aataccttta tccggacgca ggacgagagt 840
atgtccacag tgaagtggat actccgcgac atcgaagctc ttggtgacaa gccggctctc 900
gtttcgcaca ttggagatat aagctacgct cgtggttact cctgggtgtg ggatgagttc 960
tttgctcaga tcgagcctat tgcctcgaga gttccttacc acgtctgcat tggtaaccac 1020

```
gagtatgact tccctactca gccgtggaaa cctgattggg gaacttacgg taatgacggt   1080

gggggagagt gcggtgtgcc gtatagtctc aagttcaaca tgcctggaaa ctcgtcggaa   1140

ccaacgggaa cgaaagctcc tcctacaagg aatttgtatt actcttacga catggggtcg   1200

gttcatttcc tttacatctc caccgagacg aactttctca aaggagggag gcaatacgag   1260

tttataaagc gagatcttga gtctgtgaac agggagaaaa caccgtttgt tgtcgtgcaa   1320

ggacacagac cgatgtacac cacgagcaac gaggtgagag acgcgatgat taggcaaaag   1380

atggtggagc atttggagcc gctgtttgtg gagaacaacg tgacgcttgc tctgtgggga   1440

catgttcata gatacgagag gttttgtccg ataagcaaca acacgtgtgg gaaacagtgg   1500

agaggaagcc cggttcatct tgtgatcggt atgggtggtc aagactggca accgatttgg   1560

cagccgagac cgaaccatcc gggtcttcct atattccctc agcctgaaca gtcgatgtac   1620

aggacgggtg agtttgggta cactcgtttg gttgcgaaca aagagaagct cactgtttcg   1680

tttgtgggta accatgatgg agaagttcat gatagtgttg agatgtttgc gtctggggaa   1740

gtaatcagtg ggaggaaaga ggaaactatt aagaccgttc ctgtatctgc aacacttgtg   1800

gggaaacctg agtctgatgt cttatggtat gttaaaggag caggcttgtt ggttattggt   1860

gtgcttttag ggttcattat agggtttttt acaaggggga agaaaggatc ttcttcatct   1920

gataaccgtt ggatcccagt caagaacgag gagacatga                          1959
```

<210> SEQ ID NO 19
<211> LENGTH: 652
<212> TYPE: PRT
<213> ORGANISM: Brassica rapa

<400> SEQUENCE: 19

```
Met Ile Val Glu Phe Ser Thr Phe Ile Leu Phe Leu Ser Val Phe Val
1               5                   10                  15

Ser Ser Ala Asn Ala Lys Ala Thr Leu Ser Ile Ser Pro Lys Thr Leu
            20                  25                  30

Ser Arg Ser Gly Asp Ser Ile Leu Ile Lys Trp Ser Asn Leu Asp Ser
        35                  40                  45

Pro Ser Asp Leu Asp Trp Leu Gly Ile Tyr Ser Pro Pro Ala Ser Pro
    50                  55                  60

His Asp His Phe Ile Gly Tyr Lys Phe Leu Asn Ala Ser Pro Thr Trp
65                  70                  75                  80

Gln Ser Gly Ser Gly Ala Ile Ser Leu Pro Leu Thr Asn Leu Arg Ser
                85                  90                  95

Asn Tyr Thr Phe Arg Ile Phe Arg Trp Thr Gln Ser Glu Ile Asn Pro
            100                 105                 110

Lys His Lys Asp His Asp Gln Asn Pro Leu Pro Gly Thr Lys His Leu
        115                 120                 125

Leu Ala Glu Ser Glu Gln Val Gly Phe Gly Ser Ala Gly Val Gly Arg
    130                 135                 140

Pro Glu Gln Ile His Leu Ala Phe Glu Asp Lys Val Asn Arg Met Gln
145                 150                 155                 160

Val Thr Phe Val Ala Gly Asp Gly Glu Glu Arg Phe Val Arg Tyr Gly
                165                 170                 175

Glu Ala Glu Asp Ala Leu Ala Asn Ser Ala Ala Ala Arg Gly Ile Arg
            180                 185                 190

Tyr Glu Arg Glu His Met Cys Asn Ala Pro Ala Asn Ser Thr Val Gly
        195                 200                 205
```

-continued

```
Trp Arg Asp Pro Gly Trp Ile Phe His Thr Val Met Lys Asn Leu Asn
    210                 215                 220

Gly Gly Val Arg Tyr Tyr Tyr Gln Val Gly Ser Asp Ser Lys Gly Trp
225                 230                 235                 240

Ser Glu Ile His Ser Phe Ile Ala Arg Asp Ile Tyr Ser Glu Glu Thr
                245                 250                 255

Ile Ala Phe Met Phe Gly Asp Met Gly Cys Ala Thr Pro Tyr Asn Thr
            260                 265                 270

Phe Ile Arg Thr Gln Asp Glu Ser Met Ser Thr Val Lys Trp Ile Leu
        275                 280                 285

Arg Asp Ile Glu Ala Leu Gly Asp Lys Pro Ala Leu Val Ser His Ile
    290                 295                 300

Gly Asp Ile Ser Tyr Ala Arg Gly Tyr Ser Trp Val Trp Asp Glu Phe
305                 310                 315                 320

Phe Ala Gln Ile Glu Pro Ile Ala Ser Arg Val Pro Tyr His Val Cys
                325                 330                 335

Ile Gly Asn His Glu Tyr Asp Phe Pro Thr Gln Pro Trp Lys Pro Asp
            340                 345                 350

Trp Gly Thr Tyr Gly Asn Asp Gly Gly Gly Glu Cys Gly Val Pro Tyr
        355                 360                 365

Ser Leu Lys Phe Asn Met Pro Gly Asn Ser Ser Glu Pro Thr Gly Thr
    370                 375                 380

Lys Ala Pro Pro Thr Arg Asn Leu Tyr Tyr Ser Tyr Asp Met Gly Ser
385                 390                 395                 400

Val His Phe Leu Tyr Ile Ser Thr Glu Thr Asn Phe Leu Lys Gly Gly
                405                 410                 415

Arg Gln Tyr Glu Phe Ile Lys Arg Asp Leu Glu Ser Val Asn Arg Glu
            420                 425                 430

Lys Thr Pro Phe Val Val Val Gln Gly His Arg Pro Met Tyr Thr Thr
        435                 440                 445

Ser Asn Glu Val Arg Asp Ala Met Ile Arg Gln Lys Met Val Glu His
    450                 455                 460

Leu Glu Pro Leu Phe Val Glu Asn Asn Val Thr Leu Ala Leu Trp Gly
465                 470                 475                 480

His Val His Arg Tyr Glu Arg Phe Cys Pro Ile Ser Asn Asn Thr Cys
                485                 490                 495

Gly Lys Gln Trp Arg Gly Ser Pro Val His Leu Val Ile Gly Met Gly
            500                 505                 510

Gly Gln Asp Trp Gln Pro Ile Trp Gln Pro Arg Pro Asn His Pro Gly
        515                 520                 525

Leu Pro Ile Phe Pro Gln Pro Glu Gln Ser Met Tyr Arg Thr Gly Glu
    530                 535                 540

Phe Gly Tyr Thr Arg Leu Val Ala Asn Lys Glu Lys Leu Thr Val Ser
545                 550                 555                 560

Phe Val Gly Asn His Asp Gly Glu Val His Asp Ser Val Glu Met Phe
                565                 570                 575

Ala Ser Gly Glu Val Ile Ser Gly Arg Lys Glu Glu Thr Ile Lys Thr
            580                 585                 590

Val Pro Val Ser Ala Thr Leu Val Gly Lys Pro Glu Ser Asp Val Leu
        595                 600                 605

Trp Tyr Val Lys Gly Ala Gly Leu Leu Val Ile Gly Val Leu Leu Gly
    610                 615                 620

Phe Ile Ile Gly Phe Phe Thr Arg Gly Lys Lys Gly Ser Ser Ser Ser
```

625 630 635 640

Asp Asn Arg Trp Ile Pro Val Lys Asn Glu Glu Thr
645 650

<210> SEQ ID NO 20
<211> LENGTH: 1965
<212> TYPE: DNA
<213> ORGANISM: Hordeum vulgare

<400> SEQUENCE: 20
atgcacccca aaaccccgcc tctcctcctc gtcctcctct tcttcgccgc cggcgaggcc 60
gcggggacca ccctcacggc caccccggcg aagctcaccc aatccgacca agaaatcacg 120
atccggtggt ccgacctccc gtccccggat ggcctcgacc acgtggcgat ctactccccg 180
ccgtcctcca gcgaccgcga cttcctaggc tacatcttcc tcaatggctc cgcctcctgg 240
cgcagcggcc gcggagagct caccctccca cggctcccca acctgcgggc gccctaccag 300
ttccgcctct tccgctggcc cgccagagag tactcctacc accacgtcga ccacgacggc 360
aacccgctcc cccacggcca ccaccgcgtc gccctatccg gcgaggtcgc tttcgcgggc 420
tcggccgcgc ggcccgagca ggtgcacctc gcgttcgccg atagggccga cgagatgcgg 480
gtgatgttcg tgtgcgcgga cgccggcaag agggccgtga ggtacgggct tgagaaggag 540
gaggagaagg gctggacgga agtgggcacg gaggtgagga cgtacgagca gaagcacatg 600
tgcgacacgc cggcgaacga caccgtaggg tggagggatc cgggcttcgt cttcgatggc 660
ctcatgaatg ggttggagcc cggaaggagg tacttttaca aggtcggtag tgacctggga 720
ggatggagcg agacatacag ctttatttca cgtgacagtg aggccaatga gaccattgct 780
tttctcttcg gtgatatggg cacttatgta ccatacaaca cctacatccg cacacaagat 840
gagagcttgt caacggtgaa gtggatcctc cgtgatattg aagcccttgg agataagcct 900
gcatttattt cgcacattgg ggacatcagt tatgccagag gctatgcttg ggtgtgggat 960
catttcttca gccagattga gcctattgca gccaatactc cataccatgt ctgcatagga 1020
aatcatgagt atgattggcc ttcacaacct tggaaacctt catggtctac atatgggaag 1080
gatggtggag gtgaatgtgg aataccatac agtgtcaagt tcagaatgcc tggggattct 1140
gttctaccta ctggcaatgg agctccggac acacggaatc tctactactc ttttgattca 1200
ggcgtcgtgc attttgtgta catgtcgact gaaactaatt tcgttcaggg cagcgaccaa 1260
cacaatttcc taaaagctga tctggagaag gtgaaccgaa gcagaacccc atttgttgtg 1320
tttcagggcc accggcccat gtatacctcg agcaacgaag ccagggattc tgccatgaga 1380
cagcagatgg tccagcatct tgaaccgctc ttggtgatat acaatgtgac gcttgccctg 1440
tggggacatg tccataggta tgagaggttc tgccccatga agaattcaca gtgtctgaac 1500
acatcatcaa gcttcgtata ccctggtgcc cctgttcatg ttgtgatcgg gatggctgga 1560
caagattggc aaccgatctg gcaaccaagg cgtgatcatc caaatgttcc catctttcca 1620
cagcctggga tctccatgta ccgtggtggt gagttcgggt acacaaagct cgcagctaac 1680
agggagaagc taacgctgat gtacgttggg aaccacgatg gacaagtcca tgacatggtg 1740
gaaatattct ctggacaaac atctactgaa gctagcgcta ctgaggcggt caatcaaaca 1800
aagctcagct cgggagccag cgccaagctg aagatttccc caatatactt ggaaattgga 1860
ggtagtgtga tgtttgccct aatgcttggt tttgccttgg gatttctcct caggaagaag 1920
agagaagctg cacaatggac tccggtcaag aacgaggaat cctaa 1965

<210> SEQ ID NO 21
<211> LENGTH: 654
<212> TYPE: PRT
<213> ORGANISM: Hordeum vulgare

<400> SEQUENCE: 21

```
Met His Pro Lys Thr Pro Pro Leu Leu Leu Val Leu Leu Phe Phe Ala
1               5                   10                  15

Ala Gly Glu Ala Ala Gly Thr Thr Leu Thr Ala Thr Pro Ala Lys Leu
            20                  25                  30

Thr Gln Ser Asp Gln Glu Ile Thr Ile Arg Trp Ser Asp Leu Pro Ser
        35                  40                  45

Pro Asp Gly Leu Asp His Val Ala Ile Tyr Ser Pro Pro Ser Ser Ser
    50                  55                  60

Asp Arg Asp Phe Leu Gly Tyr Ile Phe Leu Asn Gly Ser Ala Ser Trp
65                  70                  75                  80

Arg Ser Gly Arg Gly Glu Leu Thr Leu Pro Arg Leu Pro Asn Leu Arg
                85                  90                  95

Ala Pro Tyr Gln Phe Arg Leu Phe Arg Trp Pro Ala Arg Glu Tyr Ser
            100                 105                 110

Tyr His His Val Asp His Asp Gly Asn Pro Leu Pro His Gly His His
        115                 120                 125

Arg Val Ala Leu Ser Gly Glu Val Ala Phe Ala Gly Ser Ala Ala Arg
    130                 135                 140

Pro Glu Gln Val His Leu Ala Phe Ala Asp Arg Ala Asp Glu Met Arg
145                 150                 155                 160

Val Met Phe Val Cys Ala Asp Ala Gly Lys Arg Ala Val Arg Tyr Gly
                165                 170                 175

Leu Glu Lys Glu Glu Glu Lys Gly Trp Thr Glu Val Gly Thr Glu Val
            180                 185                 190

Arg Thr Tyr Glu Gln Lys His Met Cys Asp Thr Pro Ala Asn Asp Thr
        195                 200                 205

Val Gly Trp Arg Asp Pro Gly Phe Val Phe Asp Gly Leu Met Asn Gly
    210                 215                 220

Leu Glu Pro Gly Arg Arg Tyr Phe Tyr Lys Val Gly Ser Asp Leu Gly
225                 230                 235                 240

Gly Trp Ser Glu Thr Tyr Ser Phe Ile Ser Arg Asp Ser Glu Ala Asn
                245                 250                 255

Glu Thr Ile Ala Phe Leu Phe Gly Asp Met Gly Thr Tyr Val Pro Tyr
            260                 265                 270

Asn Thr Tyr Ile Arg Thr Gln Asp Glu Ser Leu Ser Thr Val Lys Trp
        275                 280                 285

Ile Leu Arg Asp Ile Glu Ala Leu Gly Asp Lys Pro Ala Phe Ile Ser
    290                 295                 300

His Ile Gly Asp Ile Ser Tyr Ala Arg Gly Tyr Ala Trp Val Trp Asp
305                 310                 315                 320

His Phe Phe Ser Gln Ile Glu Pro Ile Ala Ala Asn Thr Pro Tyr His
                325                 330                 335

Val Cys Ile Gly Asn His Glu Tyr Asp Trp Pro Ser Gln Pro Trp Lys
            340                 345                 350

Pro Ser Trp Ser Thr Tyr Gly Lys Asp Gly Gly Gly Glu Cys Gly Ile
        355                 360                 365

Pro Tyr Ser Val Lys Phe Arg Met Pro Gly Asp Ser Val Leu Pro Thr
    370                 375                 380
```

```
Gly Asn Gly Ala Pro Asp Thr Arg Asn Leu Tyr Tyr Ser Phe Asp Ser
385                 390                 395                 400

Gly Val Val His Phe Val Tyr Met Ser Thr Glu Thr Asn Phe Val Gln
                405                 410                 415

Gly Ser Asp Gln His Asn Phe Leu Lys Ala Asp Leu Glu Lys Val Asn
            420                 425                 430

Arg Ser Arg Thr Pro Phe Val Val Phe Gln Gly His Arg Pro Met Tyr
        435                 440                 445

Thr Ser Ser Asn Glu Ala Arg Asp Ser Ala Met Arg Gln Gln Met Val
    450                 455                 460

Gln His Leu Glu Pro Leu Leu Val Ile Tyr Asn Val Thr Leu Ala Leu
465                 470                 475                 480

Trp Gly His Val His Arg Tyr Glu Arg Phe Cys Pro Met Lys Asn Ser
                485                 490                 495

Gln Cys Leu Asn Thr Ser Ser Ser Phe Val Tyr Pro Gly Ala Pro Val
            500                 505                 510

His Val Val Ile Gly Met Ala Gly Gln Asp Trp Gln Pro Ile Trp Gln
        515                 520                 525

Pro Arg Arg Asp His Pro Asn Val Pro Ile Phe Pro Gln Pro Gly Ile
    530                 535                 540

Ser Met Tyr Arg Gly Gly Glu Phe Gly Tyr Thr Lys Leu Ala Ala Asn
545                 550                 555                 560

Arg Glu Lys Leu Thr Leu Met Tyr Val Gly Asn His Asp Gly Gln Val
                565                 570                 575

His Asp Met Val Glu Ile Phe Ser Gly Gln Thr Ser Thr Glu Ala Ser
            580                 585                 590

Ala Thr Glu Ala Val Asn Gln Thr Lys Leu Ser Ser Gly Ala Ser Ala
        595                 600                 605

Lys Leu Lys Ile Ser Pro Ile Tyr Leu Glu Ile Gly Gly Ser Val Met
    610                 615                 620

Phe Ala Leu Met Leu Gly Phe Ala Leu Gly Phe Leu Leu Arg Lys Lys
625                 630                 635                 640

Arg Glu Ala Ala Gln Trp Thr Pro Val Lys Asn Glu Glu Ser
                645                 650
```

<210> SEQ ID NO 22
<211> LENGTH: 1980
<212> TYPE: DNA
<213> ORGANISM: Medicago truncatula

<400> SEQUENCE: 22

```
atgatccctc acacaatact cttcacctta ctcttatcct caaccttcac ctctaccctc      60

gcccaatcaa aacccaccct aacagtaacc ccaaccaccc tcacaaaatc tggcgacacc     120

gtcaccctcc ggtggtccgg tatccaatcc ccctccgatc tcgacttcct cgcaatctac     180

tccccaccta cctccgccca caaaaactac atcggctacc tcttcctctc caaatccccc     240

acctggcaat ccggctccgg caacctctct cttcctctca tcaacctccg ttccaactac     300

tccttccgta tcttccactg gtcccaatcc gaaatcaacc ctaaacgtca agatcacgat     360

cataatccct taccacaaac gcatcacctt cttgctttct ctgatgaagt ttcttttcca     420

tcccttcgac cggagcagat tcatcttgct tttgcagatg aagaagatgc tatgagggtg     480

atgtatgtga cgggggttcc gaagaagacg tatgtgagat atggagaaag agaggatatg     540

atggatagat tggttgttgc gaatgtgaag agatatgaga gagagcatat gtgtgatgct     600
```

```
cctgctaatc agagtgttgg ttggagggat cctggtttta ttcatgatgc tttgattact    660

ggtttggaca aaggaagaag atattactac caggttggaa atgataatgg aggttggagt    720

gcaacccata gctttgtgtc gaggaatagt gattcaaatg aaacaatagc tttccttttc    780

ggtgacatgg gaacatttac agcatacaat acgtatttgc gtacacaaga tgagagcata    840

tcaaccatga agtggatcct gcgtgatgtt gaagctctag gaaacaagcc cgcctttata    900

tcacacattg gagacacaag ttatgcaaga ggttatgcgt ggttgtggga tcatttttc    960

gcacagattg aacctgttgc aaccaaagtg gcataccatg tatgcattgg caatcacgag   1020

tataactggc ctttacagcc gtggaaacct gattgggcta attatagaac agatggaggt   1080

ggtgaatgtg gtgtacccta cagtttaagg ttcaacatgc caggaaactc ttcagaaccc   1140

actggaactg tagctccagc cactaggaat ctttattact catttgatat gggagcagta   1200

cattttgttt atatttccac agagaccaat ttccttcctg ggagcaatca gtataacttc   1260

ttaaagcgtg atttggaatc agttgacagg aacaagactc cttttgtagt agtccaaggg   1320

caccgaccca tgtacacaac aagcaatgaa tttagggatg ctgcgttaag aggaaagatg   1380

gttgagcacc tggaacctct attggtgaat aaccatgtaa cccttgccct ttggggtcat   1440

gttcataggt acgagagatt ttgtccacta aacaacttta cttgtggaaa tggtgtgggt   1500

cggagagcag gggaaaaagg tcataccatt catcttgtga tcggcatggc agggcaagac   1560

tggcaaccca tgtggcgacc aagaccggat catcccgatg tcccaatcta tccacaacca   1620

aaacgatctt tgtaccgcgg gggtgagttc ggatacatta gattgatggc tacaaagcag   1680

aatctcgtga tttcttatgt tggtaatcat gatggcgagg tgcatgacac attggagatt   1740

ctggaatctg gagaagttgt tagtggtggt ggtggtaacg ataatgttaa tggcggtatt   1800

ggtagtgcta aacctgaagg tcagattaaa gaatccacgt tgtcgtggta tgtccaggga   1860

ggaagtgtac tagtgcttgg ggcctttatg ggctacattc ttggtttcgt ttcacatgct   1920

aggaagaagc agcccgagtc caggagtggt tttagccccg tgaagactga ggaaacatga   1980
```

```
<210> SEQ ID NO 23
<211> LENGTH: 659
<212> TYPE: PRT
<213> ORGANISM: Medicago truncatula

<400> SEQUENCE: 23

Met Ile Pro His Thr Ile Leu Phe Thr Leu Leu Leu Ser Ser Thr Phe
1               5                   10                  15

Thr Ser Thr Leu Ala Gln Ser Lys Pro Thr Leu Thr Val Thr Pro Thr
            20                  25                  30

Thr Leu Thr Lys Ser Gly Asp Thr Val Thr Leu Arg Trp Ser Gly Ile
        35                  40                  45

Gln Ser Pro Ser Asp Leu Asp Phe Leu Ala Ile Tyr Ser Pro Pro Thr
    50                  55                  60

Ser Ala His Lys Asn Tyr Ile Gly Tyr Leu Phe Leu Ser Lys Ser Pro
65                  70                  75                  80

Thr Trp Gln Ser Gly Ser Gly Asn Leu Ser Leu Pro Leu Ile Asn Leu
                85                  90                  95

Arg Ser Asn Tyr Ser Phe Arg Ile Phe His Trp Ser Gln Ser Glu Ile
            100                 105                 110

Asn Pro Lys Arg Gln Asp His Asp His Asn Pro Leu Pro Gln Thr His
        115                 120                 125
```

```
His Leu Leu Ala Phe Ser Asp Glu Val Ser Phe Pro Ser Leu Arg Pro
    130                 135                 140

Glu Gln Ile His Leu Ala Phe Ala Asp Glu Glu Asp Ala Met Arg Val
145                 150                 155                 160

Met Tyr Val Thr Gly Val Pro Lys Lys Thr Tyr Val Arg Tyr Gly Glu
                165                 170                 175

Arg Glu Asp Met Met Asp Arg Leu Val Val Ala Asn Val Lys Arg Tyr
            180                 185                 190

Glu Arg Glu His Met Cys Asp Ala Pro Ala Asn Gln Ser Val Gly Trp
        195                 200                 205

Arg Asp Pro Gly Phe Ile His Asp Ala Leu Ile Thr Gly Leu Asp Lys
    210                 215                 220

Gly Arg Arg Tyr Tyr Tyr Gln Val Gly Asn Asp Asn Gly Gly Trp Ser
225                 230                 235                 240

Ala Thr His Ser Phe Val Ser Arg Asn Ser Asp Ser Asn Glu Thr Ile
                245                 250                 255

Ala Phe Leu Phe Gly Asp Met Gly Thr Phe Thr Ala Tyr Asn Thr Tyr
            260                 265                 270

Leu Arg Thr Gln Asp Glu Ser Ile Ser Thr Met Lys Trp Ile Leu Arg
        275                 280                 285

Asp Val Glu Ala Leu Gly Asn Lys Pro Ala Phe Ile Ser His Ile Gly
    290                 295                 300

Asp Thr Ser Tyr Ala Arg Gly Tyr Ala Trp Leu Trp Asp His Phe Phe
305                 310                 315                 320

Ala Gln Ile Glu Pro Val Ala Thr Lys Val Ala Tyr His Val Cys Ile
                325                 330                 335

Gly Asn His Glu Tyr Asn Trp Pro Leu Gln Pro Trp Lys Pro Asp Trp
            340                 345                 350

Ala Asn Tyr Arg Thr Asp Gly Gly Gly Glu Cys Gly Val Pro Tyr Ser
        355                 360                 365

Leu Arg Phe Asn Met Pro Gly Asn Ser Ser Glu Pro Thr Gly Thr Val
    370                 375                 380

Ala Pro Ala Thr Arg Asn Leu Tyr Tyr Ser Phe Asp Met Gly Ala Val
385                 390                 395                 400

His Phe Val Tyr Ile Ser Thr Glu Thr Asn Phe Leu Pro Gly Ser Asn
                405                 410                 415

Gln Tyr Asn Phe Leu Lys Arg Asp Leu Glu Ser Val Asp Arg Asn Lys
            420                 425                 430

Thr Pro Phe Val Val Val Gln Gly His Arg Pro Met Tyr Thr Thr Ser
        435                 440                 445

Asn Glu Phe Arg Asp Ala Ala Leu Arg Gly Lys Met Val Glu His Leu
    450                 455                 460

Glu Pro Leu Leu Val Asn Asn His Val Thr Leu Ala Leu Trp Gly His
465                 470                 475                 480

Val His Arg Tyr Glu Arg Phe Cys Pro Leu Asn Asn Phe Thr Cys Gly
                485                 490                 495

Asn Gly Val Gly Arg Arg Ala Gly Glu Lys Gly His Thr Ile His Leu
            500                 505                 510

Val Ile Gly Met Ala Gly Gln Asp Trp Gln Pro Met Trp Arg Pro Arg
        515                 520                 525

Pro Asp His Pro Asp Val Pro Ile Tyr Pro Gln Pro Lys Arg Ser Leu
    530                 535                 540

Tyr Arg Gly Gly Glu Phe Gly Tyr Ile Arg Leu Met Ala Thr Lys Gln
```

```
545                 550                 555                 560

Asn Leu Val Ile Ser Tyr Val Gly Asn His Asp Gly Glu Val His Asp
                565                 570                 575

Thr Leu Glu Ile Leu Glu Ser Gly Glu Val Val Ser Gly Gly Gly Gly
            580                 585                 590

Asn Asp Asn Val Asn Gly Gly Ile Gly Ser Ala Lys Pro Glu Gly Gln
        595                 600                 605

Ile Lys Glu Ser Thr Leu Ser Trp Tyr Val Gln Gly Gly Ser Val Leu
    610                 615                 620

Val Leu Gly Ala Phe Met Gly Tyr Ile Leu Gly Phe Val Ser His Ala
625                 630                 635                 640

Arg Lys Lys Gln Pro Glu Ser Arg Ser Gly Phe Ser Pro Val Lys Thr
                645                 650                 655

Glu Glu Thr
```

<210> SEQ ID NO 24
<211> LENGTH: 2007
<212> TYPE: DNA
<213> ORGANISM: Physcomitrella patens

<400> SEQUENCE: 24

```
atgggatcgc aagtattcca ttttcttctg gtgttctttg ggtactttct gcatggagct     60

tcatcagaat ctgtgatttt ggacgcgaga cctacaatat tacaacattc aggagaaaat    120

atcactcttg cttggaaggg tgtgaattta ccgacgaaat acgattggct gggtatatat    180

acgcctccta cttctcctga cgaccagcat atcgggtaca tacttctctc ttcctgttca    240

acatggacaa caggcgcctg ctccttgcag atccccttgg tcaacatgcg tgctccttac    300

agtttccgaa ttttcagagg cgtgttcgta aatgtatctg caagtacaaa tgtgactgga    360

tcaaacaatg ggctacaac gatatcattg gatcgggagg gtaatcctct accagatgtc    420

acgaaacggt tagctgcaag cccagttgtt caattctcca attacaacga gccaacacaa    480

attcatctag ctctttcctc ggacgagact gctgttaggg ttatgtttgt cactagggat    540

cctctgagaa gccaagtaag attcggggaa gatggagatg aactgggcaa cacagttgat    600

gctacatcag tcacatactc tcaaattgat atgtgcgatg aacctgcaag ttcttatggg    660

tggagatctc cgggatacat acataatgtt gtgatggggg ggctgaatcc tgggagtcgc    720

tatttctatc gggtaggaag caatgtagga ggatggagct cgacctatag cttcatcgct    780

ccacatcctc gtgctgatga aacaaatgct ctcatattcg gtgacatggg tacttcgatt    840

ccttattcaa cgtatcaata cacgcagagc gagagcaaga ataccgtgaa gtggctcaca    900

cgggacctag aacaaatagg tgacaaacct agcttcgtag cgcacattgg tgacataagc    960

tatgctcgtg gtttatcttg gctctgggac aacttcttca cccaaatcga gcccgtagct   1020

gcaagatcac catatcatgt ttgcatggga aaccacgaat atgattggcc tgggcaacct   1080

ttcaagccag actggtcacc ataccaaaca gatggaggcg gagaatgtgg cgtgccatat   1140

agcttacgct tcatcatgcc gggaaactcc tccttaccca ctggaactac ctccccagcc   1200

accaaaaacc tctattattc cattgatgtt ggggttgtgc atttcctctt ctattctacc   1260

gaaaccgatt tccaggtagg ctccccccag tacactttta tagccaacga cttgagaaca   1320

gttgacagga acaagacgcc ctttgtggta tttttgggcc atcggccgct ctatacaacc   1380

gattaccgag ccttgttaga cacgatgaca cagaaattag ttcaaacttt tgagcctttg   1440

ttgatagata ccaatgtcac tgtagccttt tgtggccatg tccataagta cgagcgaatg   1500
```

```
tgccccttga aaaattacac ctgtattgaa ccatctaagg caaacggtga gcttccaatt   1560

catatggtgg tgggaatggg aggtgctgat caccaaccca ttgatgaccc tctccccagt   1620

caaagtcagc ctatctttcc tcagcccagc tggtcagtat ttcgaacatt tgaatgggga   1680

tatatcaggc tacatgcaac gagacatctc atgacgattt catatgttgg taaccacgat   1740

gggaaggtgc atgatgttgt cgaaattcca gttctggatg atatcaagtc tggagcatat   1800

gttgagtcga gggagtcttt ttttgacact gccagcggag tgcaaatacc ttgtggcagg   1860

tctgagaata ttgtagcatt cctgtttgtt ttagcgttgg gttgtggatg cggggcggct   1920

gctactcttt ttttcatgcg gaggcagcag aggaagcaga tttggcagcc tgtcaaccgt   1980

gaggaagcta gttcttctca attataa                                      2007
```

```
<210> SEQ ID NO 25
<211> LENGTH: 668
<212> TYPE: PRT
<213> ORGANISM: Physcomitrella patens

<400> SEQUENCE: 25

Met Gly Ser Gln Val Phe His Phe Leu Leu Val Phe Phe Gly Tyr Phe
1               5                   10                  15

Leu His Gly Ala Ser Ser Glu Ser Val Ile Leu Asp Ala Arg Pro Thr
            20                  25                  30

Ile Leu Gln His Ser Gly Glu Asn Ile Thr Leu Ala Trp Lys Gly Val
        35                  40                  45

Asn Leu Pro Thr Lys Tyr Asp Trp Leu Gly Ile Tyr Thr Pro Pro Thr
    50                  55                  60

Ser Pro Asp Asp Gln His Ile Gly Tyr Ile Leu Leu Ser Ser Cys Ser
65                  70                  75                  80

Thr Trp Thr Thr Gly Ala Cys Ser Leu Gln Ile Pro Leu Val Asn Met
                85                  90                  95

Arg Ala Pro Tyr Ser Phe Arg Ile Phe Arg Gly Val Phe Val Asn Val
            100                 105                 110

Ser Ala Ser Thr Asn Val Thr Gly Ser Asn Asn Gly Ala Thr Thr Ile
        115                 120                 125

Ser Leu Asp Arg Glu Gly Asn Pro Leu Pro Asp Val Thr Lys Arg Leu
    130                 135                 140

Ala Ala Ser Pro Val Val Gln Phe Ser Asn Tyr Asn Glu Pro Thr Gln
145                 150                 155                 160

Ile His Leu Ala Leu Ser Ser Asp Glu Thr Ala Val Arg Val Met Phe
                165                 170                 175

Val Thr Arg Asp Pro Leu Arg Ser Gln Val Arg Phe Gly Glu Asp Gly
            180                 185                 190

Asp Glu Leu Gly Asn Thr Val Asp Ala Thr Ser Val Thr Tyr Ser Gln
        195                 200                 205

Ile Asp Met Cys Asp Glu Pro Ala Ser Ser Tyr Gly Trp Arg Ser Pro
    210                 215                 220

Gly Tyr Ile His Asn Val Val Met Gly Gly Leu Asn Pro Gly Ser Arg
225                 230                 235                 240

Tyr Phe Tyr Arg Val Gly Ser Asn Val Gly Gly Trp Ser Ser Thr Tyr
                245                 250                 255

Ser Phe Ile Ala Pro His Pro Arg Ala Asp Glu Thr Asn Ala Leu Ile
            260                 265                 270

Phe Gly Asp Met Gly Thr Ser Ile Pro Tyr Ser Thr Tyr Gln Tyr Thr
```

```
        275                 280                 285

Gln Ser Glu Ser Lys Asn Thr Val Lys Trp Leu Thr Arg Asp Leu Glu
    290                 295                 300

Gln Ile Gly Asp Lys Pro Ser Phe Val Ala His Ile Gly Asp Ile Ser
305                 310                 315                 320

Tyr Ala Arg Gly Leu Ser Trp Leu Trp Asp Asn Phe Phe Thr Gln Ile
                325                 330                 335

Glu Pro Val Ala Ala Arg Ser Pro Tyr His Val Cys Met Gly Asn His
            340                 345                 350

Glu Tyr Asp Trp Pro Gly Gln Pro Phe Lys Pro Asp Trp Ser Pro Tyr
        355                 360                 365

Gln Thr Asp Gly Gly Gly Glu Cys Gly Val Pro Tyr Ser Leu Arg Phe
    370                 375                 380

Ile Met Pro Gly Asn Ser Ser Leu Pro Thr Gly Thr Thr Ser Pro Ala
385                 390                 395                 400

Thr Lys Asn Leu Tyr Tyr Ser Ile Asp Val Gly Val Val His Phe Leu
                405                 410                 415

Phe Tyr Ser Thr Glu Thr Asp Phe Gln Val Gly Ser Pro Gln Tyr Thr
            420                 425                 430

Phe Ile Ala Asn Asp Leu Arg Thr Val Asp Arg Asn Lys Thr Pro Phe
        435                 440                 445

Val Val Phe Leu Gly His Arg Pro Leu Tyr Thr Thr Asp Tyr Arg Ala
    450                 455                 460

Leu Leu Asp Thr Met Thr Gln Lys Leu Val Gln Thr Phe Glu Pro Leu
465                 470                 475                 480

Leu Ile Asp Thr Asn Val Thr Val Ala Phe Cys Gly His Val His Lys
                485                 490                 495

Tyr Glu Arg Met Cys Pro Leu Lys Asn Tyr Thr Cys Ile Glu Pro Ser
            500                 505                 510

Lys Ala Asn Gly Glu Leu Pro Ile His Met Val Val Gly Met Gly Gly
        515                 520                 525

Ala Asp His Gln Pro Ile Asp Asp Pro Leu Pro Ser Gln Ser Gln Pro
    530                 535                 540

Ile Phe Pro Gln Pro Ser Trp Ser Val Phe Arg Thr Phe Glu Trp Gly
545                 550                 555                 560

Tyr Ile Arg Leu His Ala Thr Arg His Leu Met Thr Ile Ser Tyr Val
                565                 570                 575

Gly Asn His Asp Gly Lys Val His Asp Val Val Glu Ile Pro Val Leu
            580                 585                 590

Asp Asp Ile Lys Ser Gly Ala Tyr Val Glu Ser Arg Glu Ser Phe Phe
        595                 600                 605

Asp Thr Ala Ser Gly Val Gln Ile Pro Cys Gly Arg Ser Glu Asn Ile
    610                 615                 620

Val Ala Phe Leu Phe Val Leu Ala Leu Gly Cys Gly Cys Gly Ala Ala
625                 630                 635                 640

Ala Thr Leu Phe Phe Met Arg Arg Gln Gln Arg Lys Gln Ile Trp Gln
                645                 650                 655

Pro Val Asn Arg Glu Glu Ala Ser Ser Ser Gln Leu
            660                 665
```

```
<210> SEQ ID NO 26
<211> LENGTH: 1944
<212> TYPE: DNA
<213> ORGANISM: Populus trichocarpa
```

<400> SEQUENCE: 26

```
atgaagctcc ctatcttcct cctcctcctc ctcctctccc tcatcactca aacttccctc     60
tccaaagtca ccatctccgt gactccaaca accctccaga aatccggtga cacagtaacc    120
atttcctggt ccaacgttga ttcaccttcc aaactcgact ggctcgggct ctattcacct    180
cctgactcac ctcacgacca cttcattggc tacaagttcc tttcttcctc tccttcatgg    240
caatccgggt cgggttccat ttccttgccc atcaccaacc tccgctccaa ttactctttc    300
cggatcttcc actggaccga atccgaaatc aaccccaaac gccatgacca tgatcacaac    360
cccctccctg ggacggccca ttttctggcg gagtcggatg ttgtcgggtt cgagtcgggt    420
catgggccag agcagatcca tttggcatat acggatgatg aggacgagat gagggtgatg    480
tttgtggtgg gtgatggaga ggagaggggt gtgaagtggg gagagaggga cggggagtgg    540
agtcacgtga gtggggcacg tgtggtgagg tatgaaaggg aggatatgtg tgatgctccg    600
gcaaatggga gtattgggtg gagagatccg ggttggatcc atgatggggt aatgaaggat    660
ttgaagaaag gtgttaggta ttattatcag gttggaagcg actctaaggg ttggagcaca    720
actaggagct ttgtctctcg gaatggagac tcggatgaaa caatagcctt cctgtttggg    780
gacatgggaa cttcaacacc atatgctacc tttatccgta cacaagatga aagcatatca    840
accatgaagt ggatcctccg agacatagaa gctattggtg acaagcatgc ttttgtttct    900
catataggag atatcagcta tgcaagaggg tactcatggt tgtgggacca tttttttacc    960
caagtggaac ctgttgcttc caaagtgcca taccatgtgt gcattggtaa tcatgagtac   1020
gattggccct tacagccctg gaaaccagat tgggccaatg cagtttacgg aactgatggt   1080
ggtggtgaat gtggggttcc ttacagcctt aaatttaaca tgccagggaa ctcttcagac   1140
tcaactggga cccgtgctcc tgcaacccga aacctttact actcttttga cacaggggct   1200
gtacattttg tgtacatatc aactgagacc aattttgttg ctgggagcag ccaatataac   1260
tttataaagc aagatctgga atcagttgac cggagcaaga ctccttttgt ggtagtccaa   1320
gggcacagac caatgtatac tactagcaat gaaaacaggg atgccccaat gaggaacaaa   1380
atgcttgagc acttggaacc tttgtttacg aaatacaatg ttacccttgc actgtggggt   1440
catgtgcata gatacgaaag gttttgtcca gtgaataact tcatctgcgg aagcacttgg   1500
aagggatttc cagtccatgc tgtgattggc atggcaggac aagactggca gcccatctgg   1560
gagccaagat cagaccaccc aaatgatcca atttttccac agccagccag gtctatgttc   1620
cgtggggggg agttcgggta caccaaattg gttgccacaa aggagaagct aacacttact   1680
tatgtaggta accatgatgg aaagatgcac gatatggttg agtttttggc atctggagaa   1740
gttctcagtg gtgatgacag cattagtgtg gatgctggag ccaggattgg ggtggttgat   1800
tctacgttct catggtatgt caagggggca agtgttcttg tccttggggc ttttgtgggc   1860
tatactcttg gctacgcatc ccattccagg aagcaaaatg gtaacaaggc cagctggact   1920
cctgtgaaaa gtgaggatat atga                                          1944
```

<210> SEQ ID NO 27
<211> LENGTH: 647
<212> TYPE: PRT
<213> ORGANISM: Populus trichocarpa

<400> SEQUENCE: 27

```
Met Lys Leu Pro Ile Phe Leu Leu Leu Leu Leu Leu Ser Leu Ile Thr
1               5                   10                  15
```

```
Gln Thr Ser Leu Ser Lys Val Thr Ile Ser Val Thr Pro Thr Thr Leu
            20                  25                  30

Gln Lys Ser Gly Asp Thr Val Thr Ile Ser Trp Ser Asn Val Asp Ser
        35                  40                  45

Pro Ser Lys Leu Asp Trp Leu Gly Leu Tyr Ser Pro Pro Asp Ser Pro
    50                  55                  60

His Asp His Phe Ile Gly Tyr Lys Phe Leu Ser Ser Ser Pro Ser Trp
65                  70                  75                  80

Gln Ser Gly Ser Gly Ser Ile Ser Leu Pro Ile Thr Asn Leu Arg Ser
                85                  90                  95

Asn Tyr Ser Phe Arg Ile Phe His Trp Thr Glu Ser Glu Ile Asn Pro
            100                 105                 110

Lys Arg His Asp His Asp His Asn Pro Leu Pro Gly Thr Ala His Phe
        115                 120                 125

Leu Ala Glu Ser Asp Val Val Gly Phe Glu Ser Gly His Gly Pro Glu
    130                 135                 140

Gln Ile His Leu Ala Tyr Thr Asp Asp Glu Asp Glu Met Arg Val Met
145                 150                 155                 160

Phe Val Val Gly Asp Gly Glu Glu Arg Gly Val Lys Trp Gly Glu Arg
                165                 170                 175

Asp Gly Glu Trp Ser His Val Ser Gly Ala Arg Val Val Arg Tyr Glu
            180                 185                 190

Arg Glu Asp Met Cys Asp Ala Pro Ala Asn Gly Ser Ile Gly Trp Arg
        195                 200                 205

Asp Pro Gly Trp Ile His Asp Gly Val Met Lys Asp Leu Lys Lys Gly
    210                 215                 220

Val Arg Tyr Tyr Tyr Gln Val Gly Ser Asp Ser Lys Gly Trp Ser Thr
225                 230                 235                 240

Thr Arg Ser Phe Val Ser Arg Asn Gly Asp Ser Asp Glu Thr Ile Ala
                245                 250                 255

Phe Leu Phe Gly Asp Met Gly Thr Ser Thr Pro Tyr Ala Thr Phe Ile
            260                 265                 270

Arg Thr Gln Asp Glu Ser Ile Ser Thr Met Lys Trp Ile Leu Arg Asp
        275                 280                 285

Ile Glu Ala Ile Gly Asp Lys His Ala Phe Val Ser His Ile Gly Asp
    290                 295                 300

Ile Ser Tyr Ala Arg Gly Tyr Ser Trp Leu Trp Asp His Phe Phe Thr
305                 310                 315                 320

Gln Val Glu Pro Val Ala Ser Lys Val Pro Tyr His Val Cys Ile Gly
                325                 330                 335

Asn His Glu Tyr Asp Trp Pro Leu Gln Pro Trp Lys Pro Asp Trp Ala
            340                 345                 350

Asn Ala Val Tyr Gly Thr Asp Gly Gly Gly Glu Cys Gly Val Pro Tyr
        355                 360                 365

Ser Leu Lys Phe Asn Met Pro Gly Asn Ser Ser Asp Ser Thr Gly Thr
    370                 375                 380

Arg Ala Pro Ala Thr Arg Asn Leu Tyr Tyr Ser Phe Asp Thr Gly Ala
385                 390                 395                 400

Val His Phe Val Tyr Ile Ser Thr Glu Thr Asn Phe Val Ala Gly Ser
                405                 410                 415

Ser Gln Tyr Asn Phe Ile Lys Gln Asp Leu Glu Ser Val Asp Arg Ser
            420                 425                 430
```

```
Lys Thr Pro Phe Val Val Val Gln Gly His Arg Pro Met Tyr Thr Thr
        435                 440                 445

Ser Asn Glu Asn Arg Asp Ala Pro Met Arg Asn Lys Met Leu Glu His
    450                 455                 460

Leu Glu Pro Leu Phe Thr Lys Tyr Asn Val Thr Leu Ala Leu Trp Gly
465                 470                 475                 480

His Val His Arg Tyr Glu Arg Phe Cys Pro Val Asn Asn Phe Ile Cys
                485                 490                 495

Gly Ser Thr Trp Lys Gly Phe Pro Val His Ala Val Ile Gly Met Ala
            500                 505                 510

Gly Gln Asp Trp Gln Pro Ile Trp Glu Pro Arg Ser Asp His Pro Asn
        515                 520                 525

Asp Pro Ile Phe Pro Gln Pro Ala Arg Ser Met Phe Arg Gly Gly Glu
    530                 535                 540

Phe Gly Tyr Thr Lys Leu Val Ala Thr Lys Glu Lys Leu Thr Leu Thr
545                 550                 555                 560

Tyr Val Gly Asn His Asp Gly Lys Met His Asp Met Val Glu Phe Leu
                565                 570                 575

Ala Ser Gly Glu Val Leu Ser Gly Asp Asp Ser Ile Ser Val Asp Ala
            580                 585                 590

Gly Ala Arg Ile Gly Val Val Asp Ser Thr Phe Ser Trp Tyr Val Lys
        595                 600                 605

Gly Ala Ser Val Leu Val Leu Gly Ala Phe Val Gly Tyr Thr Leu Gly
    610                 615                 620

Tyr Ala Ser His Ser Arg Lys Gln Asn Gly Asn Lys Ala Ser Trp Thr
625                 630                 635                 640

Pro Val Lys Ser Glu Asp Ile
                645


<210> SEQ ID NO 28
<211> LENGTH: 1962
<212> TYPE: DNA
<213> ORGANISM: Saccharum officinarum

<400> SEQUENCE: 28

atgtccccccg aaaaccccca cctccgcttc ctcctcttcc tcgccgtcgc ggccgtcgcc      60

gccggcgggg ctgcggcggg caccaccctc accgcgaccc tctccagcga ccagatcaag     120

atccgctgga caggcctccc ggccccggac ggcctcgact acgtcggcat ctactcgccg     180

ccgtcctccc gcgaccgcga cttcctcggc tacctcttcc tcaacggctc cgcctcctgg     240

cgcggcggct caggggagct ctccctcccg cgcctcccga ccctgcgcgc gccctaccag     300

ttccgcctct tccgctggcc cgccaacgag tactcctacc accacatcga ccatgaccgg     360

aacccgctcc cccacggcaa gcaccgcgtc gccgtctccg ccgacgtctc cgtcggcgac     420

cccgcgcgcc ccgagcaggt gcacctcgcg ttcgcggatg ggatcgacga gatgcgggtc     480

ctgttcgtgt gcggcgaccg cgggaagagg gtcgtcaggt acgggctgca aaaggaagac     540

gagaaggagt ggaaggaggt gggcacggat gtgagcacgt acaagcaaaa gcacatgtgc     600

gattggccgc cgaacagcag cgtcgcctgg agggatcccg gattcgtctt cgacgggctc     660

atgaagggat tggagcctgg aaggaggtac ttttacaagg ttggtagtga cactggagga     720

tggagtgaga tatacagctt tatttcacgt gacagtgaag ccaatgagac caacacattt     780

ctgtttggtg acatgggaac ttatgtgcct tatcacacct acattcgcac acaagatgag     840

agcttgtcca ctgtaaagtg gatccttcgt gatattgaag cccttgggga taaacccgcc     900
```

```
tttatttcac acattgggga catcagctat gctagaggtt attcttgggt atgggatcat    960

ttcttcagtc agattgagcc aattgctgcc aataccccat accatgtctg tataggaaat   1020

catgagtatg attggccatc tcaaccttgg aaaccatggt gggctacata tggaaaggat   1080

ggtggaggcg aatgtggaat accgtatagc gtcaagttca gaatgcctgg caattctatt   1140

ctaccaactg gtaatggtgg cccagacacc aggaatcttt attactcctt tgactcaggt   1200

gtggtgcatt tcgtctacat gtcaaccgaa acaaattttg ttcagggcag tgatcagtac   1260

aacttcttga aagcggacct tgagaaggtg aaccgaagta gaacaccatt tgttgttttt   1320

cagggccacc gccccatgta cacctcaagt gatgaaacca gggacgcggc cttgagacag   1380

cagatgctcc agcatttgga accgctgctg gtgacataca gtgtgaccct tgcactatgg   1440

ggacatgtcc acaggtacga gaggttctgc ccgatgaaga acttccaatg tgtcaacact   1500

tcatcaagct tccaatactc tggtgctcct gtgcatcttg tgattgggat gggcggggca   1560

gactgggcaa ccatatggca accgaggcct gatcacccag acgtccccat ctttccacag   1620

cctgagaggt ccatgtaccg tggcggtgag tttggataca caaggcttgc agcaacaagg   1680

gagaagctaa cattaaccta tgtggggaac catgatgggc aagtccatga tataatggag   1740

atattttccg gcctggtatc tagtaacagt agtgttgctg aggtggtgga tgatactaaa   1800

catggcacag gagtcagcac cgtgcgaaaa atatctccgt tgtacttgga aatcggaggc   1860

agtgtattgt ttgcactgct tctgggattt tcctttggat ttcttatcag gagaaagaaa   1920

gaagctgcac agtggactcc agtaaagaac gaggaatcgt aa                      1962
```

```
<210> SEQ ID NO 29
<211> LENGTH: 653
<212> TYPE: PRT
<213> ORGANISM: Saccharum officinarum

<400> SEQUENCE: 29

Met Ser Pro Glu Asn Pro His Leu Arg Phe Leu Leu Phe Leu Ala Val
1               5                   10                  15

Ala Ala Val Ala Ala Gly Gly Ala Ala Ala Gly Thr Thr Leu Thr Ala
            20                  25                  30

Thr Leu Ser Ser Asp Gln Ile Lys Ile Arg Trp Thr Gly Leu Pro Ala
        35                  40                  45

Pro Asp Gly Leu Asp Tyr Val Gly Ile Tyr Ser Pro Pro Ser Ser Arg
    50                  55                  60

Asp Arg Asp Phe Leu Gly Tyr Leu Phe Leu Asn Gly Ser Ala Ser Trp
65                  70                  75                  80

Arg Gly Gly Ser Gly Glu Leu Ser Leu Pro Arg Leu Pro Thr Leu Arg
                85                  90                  95

Ala Pro Tyr Gln Phe Arg Leu Phe Arg Trp Pro Ala Asn Glu Tyr Ser
            100                 105                 110

Tyr His His Ile Asp His Asp Arg Asn Pro Leu Pro His Gly Lys His
        115                 120                 125

Arg Val Ala Val Ser Ala Asp Val Ser Val Gly Asp Pro Ala Arg Pro
    130                 135                 140

Glu Gln Val His Leu Ala Phe Ala Asp Gly Ile Asp Glu Met Arg Val
145                 150                 155                 160

Leu Phe Val Cys Gly Asp Arg Gly Lys Arg Val Val Arg Tyr Gly Leu
                165                 170                 175

Gln Lys Glu Asp Glu Lys Glu Trp Lys Glu Val Gly Thr Asp Val Ser
```

-continued

```
            180                 185                 190

Thr Tyr Lys Gln Lys His Met Cys Asp Trp Pro Pro Asn Ser Ser Val
        195                 200                 205

Ala Trp Arg Asp Pro Gly Phe Val Phe Asp Gly Leu Met Lys Gly Leu
    210                 215                 220

Glu Pro Gly Arg Arg Tyr Phe Tyr Lys Val Gly Ser Asp Thr Gly Gly
225                 230                 235                 240

Trp Ser Glu Ile Tyr Ser Phe Ile Ser Arg Asp Ser Glu Ala Asn Glu
                245                 250                 255

Thr Asn Thr Phe Leu Phe Gly Asp Met Gly Thr Tyr Val Pro Tyr His
            260                 265                 270

Thr Tyr Ile Arg Thr Gln Asp Glu Ser Leu Ser Thr Val Lys Trp Ile
        275                 280                 285

Leu Arg Asp Ile Glu Ala Leu Gly Asp Lys Pro Ala Phe Ile Ser His
    290                 295                 300

Ile Gly Asp Ile Ser Tyr Ala Arg Gly Tyr Ser Trp Val Trp Asp His
305                 310                 315                 320

Phe Phe Ser Gln Ile Glu Pro Ile Ala Ala Asn Thr Pro Tyr His Val
                325                 330                 335

Cys Ile Gly Asn His Glu Tyr Asp Trp Pro Ser Gln Pro Trp Lys Pro
            340                 345                 350

Trp Trp Ala Thr Tyr Gly Lys Asp Gly Gly Gly Glu Cys Gly Ile Pro
        355                 360                 365

Tyr Ser Val Lys Phe Arg Met Pro Gly Asn Ser Ile Leu Pro Thr Gly
    370                 375                 380

Asn Gly Gly Pro Asp Thr Arg Asn Leu Tyr Tyr Ser Phe Asp Ser Gly
385                 390                 395                 400

Val Val His Phe Val Tyr Met Ser Thr Glu Thr Asn Phe Val Gln Gly
                405                 410                 415

Ser Asp Gln Tyr Asn Phe Leu Lys Ala Asp Leu Glu Lys Val Asn Arg
            420                 425                 430

Ser Arg Thr Pro Phe Val Val Phe Gln Gly His Arg Pro Met Tyr Thr
        435                 440                 445

Ser Ser Asp Glu Thr Arg Asp Ala Ala Leu Arg Gln Gln Met Leu Gln
    450                 455                 460

His Leu Glu Pro Leu Leu Val Thr Tyr Ser Val Thr Leu Ala Leu Trp
465                 470                 475                 480

Gly His Val His Arg Tyr Glu Arg Phe Cys Pro Met Lys Asn Phe Gln
                485                 490                 495

Cys Val Asn Thr Ser Ser Ser Phe Gln Tyr Ser Gly Ala Pro Val His
            500                 505                 510

Leu Val Ile Gly Met Gly Gly Ala Asp Trp Ala Thr Ile Trp Gln Pro
        515                 520                 525

Arg Pro Asp His Pro Asp Val Pro Ile Phe Pro Gln Pro Glu Arg Ser
    530                 535                 540

Met Tyr Arg Gly Gly Glu Phe Gly Tyr Thr Arg Leu Ala Ala Thr Arg
545                 550                 555                 560

Glu Lys Leu Thr Leu Thr Tyr Val Gly Asn His Asp Gly Gln Val His
                565                 570                 575

Asp Ile Met Glu Ile Phe Ser Gly Leu Val Ser Ser Asn Ser Ser Val
            580                 585                 590

Ala Glu Val Val Asp Asp Thr Lys His Gly Thr Gly Val Ser Thr Val
        595                 600                 605
```

```
Arg Lys Ile Ser Pro Leu Tyr Leu Glu Ile Gly Gly Ser Val Leu Phe
    610                 615                 620

Ala Leu Leu Leu Gly Phe Ser Phe Gly Phe Leu Ile Arg Arg Lys Lys
625                 630                 635                 640

Glu Ala Ala Gln Trp Thr Pro Val Lys Asn Glu Glu Ser
                645                 650


<210> SEQ ID NO 30
<211> LENGTH: 1950
<212> TYPE: DNA
<213> ORGANISM: Solanum tuberosum

<400> SEQUENCE: 30

atgatgatcc cttttgtcac cttcacctta ctcatcttct tcaacttgat ttcatcatct     60

tcttcttcac aaatctccat ttctgtaacc ccaaaaacct tatcaaaatc tggtgatttt    120

gttacaatca aatggactgg tatcccctca ccttctaaac tcgatttctt aggaatttac    180

tctccaccca gttcactcca cgacaatttc attggctata ttttcctatc ttcaacaccc    240

gaatgggaat ctgggtcggg ttcaatttcc atccctttag tcaatcttcg atctgggtat    300

cagtttcgga tattcagatg gacggaatcg gagattgtac cggatctagt ggatcatgac    360

cacaatccat tgccgcagac gaagcatatt cttgcggtgt cggaggaggt tgggtttgtt    420

tcgggtcggg gacccgaaca ggttcatttg gctttaacgg gttttgaaga tgagatgcgg    480

gttatgtttg ttacgcctga cgggaaagag agttatgtga gatatgggtt gacccggggt    540

agattgggtc gggttgtgaa aactcgggtt gtgaggtatg agaaggaaga tttatgtgat    600

gcaccagcta atagtagtat tggatggaga gatcctgggt atatacatga tggtgttatg    660

cttaatttga aaaagggaaa gaagtattat tatcaggttg gcagtgattc agggggctgg    720

agcaccattt acagctttgt gtcacagaat agagactcag gtgaaacatt tgctttcttg    780

tttggagaca tggggactgc taccccatac ttgacatttc ttcgtacaca ggacgaaagt    840

aaatcaacga ttaagtggat tagccgtgat attgaagctc ttggtaataa gcctgccctt    900

atctcacata ttggagatat cagctacgct agaggatact cttggttgtg ggacaacttt    960

tttactcagg tagaacctgt tgcatccaga gttccatacc atgtatgcat cggaaaccat   1020

gaatatgatt ggccacttca accttggaag cctgattggt caagctacgg gaaagatggg   1080

ggaggtgaat gtggtgtacc ctacaggtca tacttccata tgccaagaaa ctcttcagtg   1140

ccgactggaa tgcatgctcc tgcaactcgg aatctttatt actcatttga ttctgggccc   1200

gttcactttg tctatatgtc aactgaaacc aatttccttc caggtagtaa ccagtatgac   1260

tttttaaagc atgacttgga atcagttgat cgagtaaaaa ctccttttgt tgtctttcaa   1320

gggcacagac caatgtacag ttcaagtagc ggagcaaaag atatatcttt gaggaagaga   1380

atgatggagt atttggaacc tcttcttgtg aagaacaatg tgaatcttgt attgtggggg   1440

catgttcata ggtatgagag gttttgccct ttgaataact tcacctgtgg aagcttggcc   1500

ttgaatggga aggagcaaaa ggctttccca gttcaaattg tgattgggat ggcaggacag   1560

gactggcagc ctatctgggc accaagagaa gaccacccta cggatcctat tttcccacag   1620

cctctgcaat ctctgtaccg tgggagtgaa tttggctacg tgaggctgca tgccacaaag   1680

aaaaagctta cactttctta tgtaggaaac catgacggag aggtgcatga taaggtggag   1740

ttcctagctt caggactact tctcagtgct ggtatccgtg atggtcctgc agatgcagta   1800

cacatggagt ctaagttctc atggtatgta aaggttggaa gtgtgctaat gcttggagct   1860
```

```
tttatgggtt acatagttgg attcttatct catgctcgga aaaattctgc tgataaagga   1920

tggagaccta taaaaactga ggaaatatga                                    1950


<210> SEQ ID NO 31
<211> LENGTH: 649
<212> TYPE: PRT
<213> ORGANISM: Solanum tuberosum

<400> SEQUENCE: 31

Met Met Ile Pro Phe Val Thr Phe Thr Leu Leu Ile Phe Phe Asn Leu
1               5                   10                  15

Ile Ser Ser Ser Ser Ser Ser Gln Ile Ser Ile Ser Val Thr Pro Lys
            20                  25                  30

Thr Leu Ser Lys Ser Gly Asp Phe Val Thr Ile Lys Trp Thr Gly Ile
        35                  40                  45

Pro Ser Pro Ser Lys Leu Asp Phe Leu Gly Ile Tyr Ser Pro Pro Ser
    50                  55                  60

Ser Leu His Asp Asn Phe Ile Gly Tyr Ile Phe Leu Ser Ser Thr Pro
65                  70                  75                  80

Glu Trp Glu Ser Gly Ser Gly Ser Ile Ser Ile Pro Leu Val Asn Leu
                85                  90                  95

Arg Ser Gly Tyr Gln Phe Arg Ile Phe Arg Trp Thr Glu Ser Glu Ile
            100                 105                 110

Val Pro Asp Leu Val Asp His Asp His Asn Pro Leu Pro Gln Thr Lys
        115                 120                 125

His Ile Leu Ala Val Ser Glu Glu Val Gly Phe Val Ser Gly Arg Gly
    130                 135                 140

Pro Glu Gln Val His Leu Ala Leu Thr Gly Phe Glu Asp Glu Met Arg
145                 150                 155                 160

Val Met Phe Val Thr Pro Asp Gly Lys Glu Ser Tyr Val Arg Tyr Gly
                165                 170                 175

Leu Thr Arg Gly Arg Leu Gly Arg Val Val Lys Thr Arg Val Val Arg
            180                 185                 190

Tyr Glu Lys Glu Asp Leu Cys Asp Ala Pro Ala Asn Ser Ser Ile Gly
        195                 200                 205

Trp Arg Asp Pro Gly Tyr Ile His Asp Gly Val Met Leu Asn Leu Lys
    210                 215                 220

Lys Gly Lys Lys Tyr Tyr Tyr Gln Val Gly Ser Asp Ser Gly Gly Trp
225                 230                 235                 240

Ser Thr Ile Tyr Ser Phe Val Ser Gln Asn Arg Asp Ser Gly Glu Thr
                245                 250                 255

Phe Ala Phe Leu Phe Gly Asp Met Gly Thr Ala Thr Pro Tyr Leu Thr
            260                 265                 270

Phe Leu Arg Thr Gln Asp Glu Ser Lys Ser Thr Ile Lys Trp Ile Ser
        275                 280                 285

Arg Asp Ile Glu Ala Leu Gly Asn Lys Pro Ala Leu Ile Ser His Ile
    290                 295                 300

Gly Asp Ile Ser Tyr Ala Arg Gly Tyr Ser Trp Leu Trp Asp Asn Phe
305                 310                 315                 320

Phe Thr Gln Val Glu Pro Val Ala Ser Arg Val Pro Tyr His Val Cys
                325                 330                 335

Ile Gly Asn His Glu Tyr Asp Trp Pro Leu Gln Pro Trp Lys Pro Asp
            340                 345                 350
```

```
Trp Ser Ser Tyr Gly Lys Asp Gly Gly Gly Glu Cys Gly Val Pro Tyr
        355                 360                 365

Arg Ser Tyr Phe His Met Pro Arg Asn Ser Ser Val Pro Thr Gly Met
    370                 375                 380

His Ala Pro Ala Thr Arg Asn Leu Tyr Tyr Ser Phe Asp Ser Gly Pro
385                 390                 395                 400

Val His Phe Val Tyr Met Ser Thr Glu Thr Asn Phe Leu Pro Gly Ser
                405                 410                 415

Asn Gln Tyr Asp Phe Leu Lys His Asp Leu Glu Ser Val Asp Arg Val
            420                 425                 430

Lys Thr Pro Phe Val Val Phe Gln Gly His Arg Pro Met Tyr Ser Ser
        435                 440                 445

Ser Ser Gly Ala Lys Asp Ile Ser Leu Arg Lys Arg Met Met Glu Tyr
    450                 455                 460

Leu Glu Pro Leu Leu Val Lys Asn Asn Val Asn Leu Val Leu Trp Gly
465                 470                 475                 480

His Val His Arg Tyr Glu Arg Phe Cys Pro Leu Asn Asn Phe Thr Cys
                485                 490                 495

Gly Ser Leu Ala Leu Asn Gly Lys Glu Gln Lys Ala Phe Pro Val Gln
            500                 505                 510

Ile Val Ile Gly Met Ala Gly Gln Asp Trp Gln Pro Ile Trp Ala Pro
        515                 520                 525

Arg Glu Asp His Pro Thr Asp Pro Ile Phe Pro Gln Pro Leu Gln Ser
    530                 535                 540

Leu Tyr Arg Gly Ser Glu Phe Gly Tyr Val Arg Leu His Ala Thr Lys
545                 550                 555                 560

Lys Lys Leu Thr Leu Ser Tyr Val Gly Asn His Asp Gly Glu Val His
                565                 570                 575

Asp Lys Val Glu Phe Leu Ala Ser Gly Leu Leu Leu Ser Ala Gly Ile
            580                 585                 590

Arg Asp Gly Pro Ala Asp Ala Val His Met Glu Ser Lys Phe Ser Trp
        595                 600                 605

Tyr Val Lys Val Gly Ser Val Leu Met Leu Gly Ala Phe Met Gly Tyr
    610                 615                 620

Ile Val Gly Phe Leu Ser His Ala Arg Lys Asn Ser Ala Asp Lys Gly
625                 630                 635                 640

Trp Arg Pro Ile Lys Thr Glu Glu Ile
                645
```

<210> SEQ ID NO 32
<211> LENGTH: 1959
<212> TYPE: DNA
<213> ORGANISM: Vitis vinifera

<400> SEQUENCE: 32

```
atgtttccaa ttttatcttt ctgcctcttc ttcgtcctcg ctcctcctct cctcgcatct      60

tcttctccag tctccataac cctaaccgcc aaaatcttag ccaaatcggg cgacccgatc     120

cgaatcaaat ggtcggggat cgactccccg tccgacctcg actggctcgg catctactcg     180

ccgccgtcct ccgcccacga caacttcatt ggctatgttt ttctgtcgtc atgtcccaca     240

tgggaatctg gatcgggttc gatcagctta cccctggtta atctccgtgc taactactct     300

tttcggatat tccggtggtc ccggtccgag gtcgacccga cccggatgga ccacgaccac     360

aatcccttgc cggggacaac gcatctggtg gcggagtccg ggaggtgggg gttcgggggc     420
```

```
ggcggggggc cggagcagat ccatttggcg tacacggata gggaggatga gatgcgggtg    480

atgttcgtga cgggggacgc gggcgtgagg actgtgaggt atggcttgag cagggacgcg    540

atgcacaggg tggtgacggc ggcggtgggg agatatgaga gggaggacat gtgtgactcg    600

ccagcgaatg agagtgttgg gtggagagat ccgggtttta ttcaagatgc ggtgatgagg    660

aatttgaaga aagggaagag atattattat aaggttggaa gtgattcagg aggttggagc    720

gcaattcaca actttatgtc acgggatatg gactctgaaa aacaatagc ttttctattt    780

ggtgacatgg ggacagcaac accatactca acctttcttc gtacacaaga ggaaagcaag    840

tcaaccgtta aatggatcct ccgtgacatt gaggctcttg atgacaaccc tgccttcatc    900

tcgcatattg gagatattag ctatgctaga ggttattcat ggttgtggga caatttttc    960

actcaggttg aacctatcgc ctccagactc ccataccatg tgtgtattgg taatcatgaa   1020

tatgattggc cattgcagcc ttggaaacct gattggtcct ccacagttta tggaacagat   1080

ggtggcggtg aatgtggagt gccctacagc cttaagttca aaatgcctgg aaactcttca   1140

gaactaactg gaacccgtgc cccagccact cgaaacctct tctactcatt tgatacgaag   1200

gcagtgcatt ttgtgtacat atcaactgag accaatttcc ttccagggag cagccaatat   1260

gactttataa agcaggattt ggagtcagtt gatcggaaaa aaaccccttt tgtggttgtc   1320

caagggcaca gaccaatgta cacaacaagc aatgaactta gagatgcccc agtgagggag   1380

aggatgctca agtatttgga acctcttttt gtgaagaaca atgtgaccct tgcactctgg   1440

ggtcatgtcc acagatatga gaggttttgc ccaataaata acttcacttg tggaaacatg   1500

ggattgaatg gggaatacct gggggattg cctgttcata tcgtgattgg gatggcaggg   1560

caagactggc agcccacatg ggaaccaaga ccagaccacc cgaaggaccc tgtctaccca   1620

caacctaaat ggtcattgta ccgtgggggt gagtttgggt acactaggtt ggttgccacc   1680

aaagagaagc taactctttc ttatgtagga aaccatgatg gtgaggtgca tgatactgtt   1740

gagattctgg catctggaca agttctcagt ggtgttggag aggatgatgc tcaacccaga   1800

gttgaggtgg cagagtacac attttcatgg tatgttaagg gggcaagtat cttggtgctg   1860

ggggctttta tgggctatgt tattgggttc gtatcacatg ccaggagaga agctgccttg   1920

agaaagaact ggactccagt gaagatcgaa gatagctga                          1959
```

<210> SEQ ID NO 33
<211> LENGTH: 652
<212> TYPE: PRT
<213> ORGANISM: Vitis vinifera

<400> SEQUENCE: 33

```
Met Phe Pro Ile Leu Ser Phe Cys Leu Phe Phe Val Leu Ala Pro Pro
1               5                   10                  15

Leu Leu Ala Ser Ser Ser Pro Val Ser Ile Thr Leu Thr Ala Lys Ile
            20                  25                  30

Leu Ala Lys Ser Gly Asp Pro Ile Arg Ile Lys Trp Ser Gly Ile Asp
        35                  40                  45

Ser Pro Ser Asp Leu Asp Trp Leu Gly Ile Tyr Ser Pro Pro Ser Ser
    50                  55                  60

Ala His Asp Asn Phe Ile Gly Tyr Val Phe Leu Ser Ser Cys Pro Thr
65                  70                  75                  80

Trp Glu Ser Gly Ser Gly Ser Ile Ser Leu Pro Leu Val Asn Leu Arg
                85                  90                  95

Ala Asn Tyr Ser Phe Arg Ile Phe Arg Trp Ser Arg Ser Glu Val Asp
```

```
            100                 105                 110

Pro Thr Arg Met Asp His Asp His Asn Pro Leu Pro Gly Thr Thr His
        115                 120                 125

Leu Val Ala Glu Ser Gly Glu Val Gly Phe Gly Gly Gly Gly Gly Pro
    130                 135                 140

Glu Gln Ile His Leu Ala Tyr Thr Asp Arg Glu Asp Glu Met Arg Val
145                 150                 155                 160

Met Phe Val Thr Gly Asp Ala Gly Val Arg Thr Val Arg Tyr Gly Leu
                165                 170                 175

Ser Arg Asp Ala Met His Arg Val Val Thr Ala Ala Val Gly Arg Tyr
            180                 185                 190

Glu Arg Glu Asp Met Cys Asp Ser Pro Ala Asn Glu Ser Val Gly Trp
        195                 200                 205

Arg Asp Pro Gly Phe Ile Gln Asp Ala Val Met Arg Asn Leu Lys Lys
    210                 215                 220

Gly Lys Arg Tyr Tyr Tyr Lys Val Gly Ser Asp Ser Gly Gly Trp Ser
225                 230                 235                 240

Ala Ile His Asn Phe Met Ser Arg Asp Met Asp Ser Glu Lys Thr Ile
                245                 250                 255

Ala Phe Leu Phe Gly Asp Met Gly Thr Ala Thr Pro Tyr Ser Thr Phe
            260                 265                 270

Leu Arg Thr Gln Glu Glu Ser Lys Ser Thr Val Lys Trp Ile Leu Arg
        275                 280                 285

Asp Ile Glu Ala Leu Asp Asp Asn Pro Ala Phe Ile Ser His Ile Gly
    290                 295                 300

Asp Ile Ser Tyr Ala Arg Gly Tyr Ser Trp Leu Trp Asp Asn Phe Phe
305                 310                 315                 320

Thr Gln Val Glu Pro Ile Ala Ser Arg Leu Pro Tyr His Val Cys Ile
                325                 330                 335

Gly Asn His Glu Tyr Asp Trp Pro Leu Gln Pro Trp Lys Pro Asp Trp
            340                 345                 350

Ser Ser Thr Val Tyr Gly Thr Asp Gly Gly Gly Glu Cys Gly Val Pro
        355                 360                 365

Tyr Ser Leu Lys Phe Lys Met Pro Gly Asn Ser Ser Glu Leu Thr Gly
    370                 375                 380

Thr Arg Ala Pro Ala Thr Arg Asn Leu Phe Tyr Ser Phe Asp Thr Lys
385                 390                 395                 400

Ala Val His Phe Val Tyr Ile Ser Thr Glu Thr Asn Phe Leu Pro Gly
                405                 410                 415

Ser Ser Gln Tyr Asp Phe Ile Lys Gln Asp Leu Glu Ser Val Asp Arg
            420                 425                 430

Lys Lys Thr Pro Phe Val Val Val Gln Gly His Arg Pro Met Tyr Thr
        435                 440                 445

Thr Ser Asn Glu Leu Arg Asp Ala Pro Val Arg Glu Arg Met Leu Lys
    450                 455                 460

Tyr Leu Glu Pro Leu Phe Val Lys Asn Asn Val Thr Leu Ala Leu Trp
465                 470                 475                 480

Gly His Val His Arg Tyr Glu Arg Phe Cys Pro Ile Asn Asn Phe Thr
                485                 490                 495

Cys Gly Asn Met Gly Leu Asn Gly Glu Tyr Leu Gly Gly Leu Pro Val
            500                 505                 510

His Ile Val Ile Gly Met Ala Gly Gln Asp Trp Gln Pro Thr Trp Glu
        515                 520                 525
```

```
Pro Arg Pro Asp His Pro Lys Asp Pro Val Tyr Pro Gln Pro Lys Trp
    530                 535                 540

Ser Leu Tyr Arg Gly Gly Glu Phe Gly Tyr Thr Arg Leu Val Ala Thr
545                 550                 555                 560

Lys Glu Lys Leu Thr Leu Ser Tyr Val Gly Asn His Asp Gly Glu Val
                565                 570                 575

His Asp Thr Val Glu Ile Leu Ala Ser Gly Gln Val Leu Ser Gly Val
            580                 585                 590

Gly Glu Asp Asp Ala Gln Pro Arg Val Glu Val Ala Glu Tyr Thr Phe
        595                 600                 605

Ser Trp Tyr Val Lys Gly Ala Ser Ile Leu Val Leu Gly Ala Phe Met
    610                 615                 620

Gly Tyr Val Ile Gly Phe Val Ser His Ala Arg Arg Glu Ala Ala Leu
625                 630                 635                 640

Arg Lys Asn Trp Thr Pro Val Lys Ile Glu Asp Ser
                645                 650


<210> SEQ ID NO 34
<211> LENGTH: 1962
<212> TYPE: DNA
<213> ORGANISM: Oryza sativa

<400> SEQUENCE: 34

atgcttctct tcctcctctt cctcctcgcc gccggcgagg ccgcggcggc ggcggcggcc     60

accacgctca ccgcgacgcc ggcgaagctc acccagtccg accgcgagat cacgatccgg    120

tggtcgggcc tcccggaccc ggacggcctc gactacgtcg gcatctactc gccgccgacc    180

tcctccgacc gcgacttcct cggctacctc ttcctcaacg gctcggccac ctggcgcacg    240

ggcaccggcg agctcaccct cccgcgcctc cccaacctgc gcgcgcccta ccagttccgc    300

ctcttccgct ggcccgcgag ggagtactcc taccaccaca tcgaccacga cgggaacccg    360

ctcccccacg gccgccaccg cgtcgccgcc tccggtgagg tcgccttcga ctccccctcc    420

cgccccgacc aggtgcacct ctcgttcgcc gacggggtcg acgagatgcg ggtcatgttc    480

gtctgcggcg acggcgggag gagggtggtg aggtacgggc cggcgaagga ggagggggag    540

ggctggaagg aggtggccgc ggaggtgagg acgtacgagc agaagcacat gtgcgactcg    600

ccggcgaact cctccgtcgg gtggagggat ccagggttcg tcttcgatgg actcatgaag    660

ggattggagc ccgggaggag gtacttctac aaggttggta gcaactcttc aggatggagc    720

gatacgtaca gcttcatttc acgtgacaac gaagccaatg aaactattgc atttctcttt    780

ggtgacatgg gcacttatat accatataac acctatgtcc gcacgcaaga tgaaagcttg    840

tcgactgtaa agtggatact tcgtgatatt caagcccttg gagataagcc tgcatttatt    900

tcacacattg ggacatcag ctatgctaga ggttatgctt gggtatggga tcacttcttc     960

aaccagattg agcctattgc tgccaatacc ccataccatg tctgcatagg aaatcatgaa   1020

tatgattggc cattgcaacc ttggaaacct tggtgggcaa ctggtatata tggaacagat   1080

ggtggaggtg aatgtggcat accttacagc gtaaagttca gaatgcctgg caattctttt   1140

gtgcctactg gcaatggagc tcccgacacc cgaaatcttt actactcctt cgattcaggg   1200

gttgtgcatt ttgtttacat gtcaactgag actaattttg ttcagggcag tgaccaatac   1260

aacttcataa aagctgacct agagaaggtc aaccgaagta gaactccttt cattgtgttt   1320

cagggccacc ggccaatgta tacatcaagc aatgaagcta gggattttgc tcatagacag   1380
```

```
cagatgctcc agaacctgga accactcttg gtaacataca aagtgaccct tgcactctgg   1440

ggacatgtcc acaggtacga gaggttctgc cccatgaaaa acttccaatg tgtcaacatg   1500

tcatcaagct tcgtataccc tggtgcccct gttcatcttg tgatcgggat gggtggtcaa   1560

gattatcaac cattctggca gccaaggaag gatcaccctg atgtacctgt ctatccgcag   1620

cctgagaggt ctatgtaccg tggtggggag tttggataca caaaacttgt agctacaaag   1680

gagaagttga cactaacgta catcggcaac catgatgggc aagtccatga tatggtggag   1740

atattctctg ggcaagtatc taataacaat ggtgttcctg aggtgatcga tgatacaaag   1800

ctcagcacag gggtcagcac caaactgaaa atccctctgt tctccttgga aattgtaggc   1860

agcgtgatgt ttgcactggt tctgggtttc tctcttggat ttctgatcag aaggaagaaa   1920

gaagctgcac agtggacccc agtgaagaac gaggagacct aa                      1962
```

<210> SEQ ID NO 35
<211> LENGTH: 653
<212> TYPE: PRT
<213> ORGANISM: Oryza sativa

<400> SEQUENCE: 35

```
Met Leu Leu Phe Leu Leu Phe Leu Leu Ala Ala Gly Glu Ala Ala Ala
1               5                   10                  15

Ala Ala Ala Ala Thr Thr Leu Thr Ala Thr Pro Ala Lys Leu Thr Gln
            20                  25                  30

Ser Asp Arg Glu Ile Thr Ile Arg Trp Ser Gly Leu Pro Asp Pro Asp
        35                  40                  45

Gly Leu Asp Tyr Val Gly Ile Tyr Ser Pro Pro Thr Ser Ser Asp Arg
    50                  55                  60

Asp Phe Leu Gly Tyr Leu Phe Leu Asn Gly Ser Ala Thr Trp Arg Thr
65                  70                  75                  80

Gly Thr Gly Glu Leu Thr Leu Pro Arg Leu Pro Asn Leu Arg Ala Pro
                85                  90                  95

Tyr Gln Phe Arg Leu Phe Arg Trp Pro Ala Arg Glu Tyr Ser Tyr His
            100                 105                 110

His Ile Asp His Asp Gly Asn Pro Leu Pro His Gly Arg His Arg Val
        115                 120                 125

Ala Ala Ser Gly Glu Val Ala Phe Asp Ser Pro Ser Arg Pro Asp Gln
    130                 135                 140

Val His Leu Ser Phe Ala Asp Gly Val Asp Glu Met Arg Val Met Phe
145                 150                 155                 160

Val Cys Gly Asp Gly Gly Arg Arg Val Val Arg Tyr Gly Pro Ala Lys
                165                 170                 175

Glu Glu Gly Glu Gly Trp Lys Glu Val Ala Ala Glu Val Arg Thr Tyr
            180                 185                 190

Glu Gln Lys His Met Cys Asp Ser Pro Ala Asn Ser Ser Val Gly Trp
        195                 200                 205

Arg Asp Pro Gly Phe Val Phe Asp Gly Leu Met Lys Gly Leu Glu Pro
    210                 215                 220

Gly Arg Arg Tyr Phe Tyr Lys Val Gly Ser Asn Ser Ser Gly Trp Ser
225                 230                 235                 240

Asp Thr Tyr Ser Phe Ile Ser Arg Asp Asn Glu Ala Asn Glu Thr Ile
                245                 250                 255

Ala Phe Leu Phe Gly Asp Met Gly Thr Tyr Ile Pro Tyr Asn Thr Tyr
            260                 265                 270
```

```
Val Arg Thr Gln Asp Glu Ser Leu Ser Thr Val Lys Trp Ile Leu Arg
        275                 280                 285

Asp Ile Gln Ala Leu Gly Asp Lys Pro Ala Phe Ile Ser His Ile Gly
    290                 295                 300

Asp Ile Ser Tyr Ala Arg Gly Tyr Ala Trp Val Trp Asp His Phe Phe
305                 310                 315                 320

Asn Gln Ile Glu Pro Ile Ala Ala Asn Thr Pro Tyr His Val Cys Ile
                325                 330                 335

Gly Asn His Glu Tyr Asp Trp Pro Leu Gln Pro Trp Lys Pro Trp Trp
            340                 345                 350

Ala Thr Gly Ile Tyr Gly Thr Asp Gly Gly Gly Glu Cys Gly Ile Pro
        355                 360                 365

Tyr Ser Val Lys Phe Arg Met Pro Gly Asn Ser Phe Val Pro Thr Gly
    370                 375                 380

Asn Gly Ala Pro Asp Thr Arg Asn Leu Tyr Tyr Ser Phe Asp Ser Gly
385                 390                 395                 400

Val Val His Phe Val Tyr Met Ser Thr Glu Thr Asn Phe Val Gln Gly
                405                 410                 415

Ser Asp Gln Tyr Asn Phe Ile Lys Ala Asp Leu Glu Lys Val Asn Arg
            420                 425                 430

Ser Arg Thr Pro Phe Ile Val Phe Gln Gly His Arg Pro Met Tyr Thr
        435                 440                 445

Ser Ser Asn Glu Ala Arg Asp Phe Ala His Arg Gln Gln Met Leu Gln
    450                 455                 460

Asn Leu Glu Pro Leu Leu Val Thr Tyr Lys Val Thr Leu Ala Leu Trp
465                 470                 475                 480

Gly His Val His Arg Tyr Glu Arg Phe Cys Pro Met Lys Asn Phe Gln
                485                 490                 495

Cys Val Asn Met Ser Ser Ser Phe Val Tyr Pro Gly Ala Pro Val His
            500                 505                 510

Leu Val Ile Gly Met Gly Gly Gln Asp Tyr Gln Pro Phe Trp Gln Pro
        515                 520                 525

Arg Lys Asp His Pro Asp Val Pro Val Tyr Pro Gln Pro Glu Arg Ser
    530                 535                 540

Met Tyr Arg Gly Gly Glu Phe Gly Tyr Thr Lys Leu Val Ala Thr Lys
545                 550                 555                 560

Glu Lys Leu Thr Leu Thr Tyr Ile Gly Asn His Asp Gly Gln Val His
                565                 570                 575

Asp Met Val Glu Ile Phe Ser Gly Gln Val Ser Asn Asn Asn Gly Val
            580                 585                 590

Pro Glu Val Ile Asp Asp Thr Lys Leu Ser Thr Gly Val Ser Thr Lys
        595                 600                 605

Leu Lys Ile Pro Leu Phe Ser Leu Glu Ile Val Gly Ser Val Met Phe
    610                 615                 620

Ala Leu Val Leu Gly Phe Ser Leu Gly Phe Leu Ile Arg Arg Lys Lys
625                 630                 635                 640

Glu Ala Ala Gln Trp Thr Pro Val Lys Asn Glu Glu Thr
                645                 650
```

<210> SEQ ID NO 36
<211> LENGTH: 738
<212> TYPE: DNA
<213> ORGANISM: Gossypium hirsutum

<400> SEQUENCE: 36

```
gcacgagcgg gaagcagcca atatgacttt ctgaagcatg atctagagtc ggttgatcgg     60

atgaagaccc cttttgttgt agttcaaggg catagaccaa tgtacactac aagtttcgaa    120

agtagggacg ccccattgag agagaaaatg cttgagcatt tggaaccttt atttgtgaaa    180

aacaatgtga accttgcatt atggggccat gttcatcggt acgagaggtt ttgtccattg    240

aagaacttca catgtggaag catggggcag aaggggaagg attgggaggc atttccagtt    300

catgttgtga ttgggatggc aggacaagac tggcaaccaa catgggaacc tcgaccagac    360

catccaacga tcccgtctac ccacaacccc aagaggtctt tgtaccgcac aggcgagttt    420

gggtacacta gattaattgc tacaaaagag aaacttacac tatcgttcgt aggaaaccat    480

gacggggagg tgcatgacat ggttgagatt ttggcatctg ggcaagttct caatggtggt    540

gatgataaca atggtaaagt cggagcagtc cataaggttg atgatgtgac acggtactca    600

ttttcacact atgtctgggg tggtagtgtc ttggtgcttg gtggttttgt tggctatgtt    660

ctgggtttcg tttcacatgc taggagacaa attgcaacag aaagaggctg gacttccttg    720

aaaaccgagg agcaatga                                                  738
```

```
<210> SEQ ID NO 37
<211> LENGTH: 245
<212> TYPE: PRT
<213> ORGANISM: Gossypium hirsutum

<400> SEQUENCE: 37

Ala Arg Ala Gly Ser Ser Gln Tyr Asp Phe Leu Lys His Asp Leu Glu
1               5                   10                  15

Ser Val Asp Arg Met Lys Thr Pro Phe Val Val Val Gln Gly His Arg
            20                  25                  30

Pro Met Tyr Thr Thr Ser Phe Glu Ser Arg Asp Ala Pro Leu Arg Glu
        35                  40                  45

Lys Met Leu Glu His Leu Glu Pro Leu Phe Val Lys Asn Asn Val Asn
    50                  55                  60

Leu Ala Leu Trp Gly His Val His Arg Tyr Glu Arg Phe Cys Pro Leu
65                  70                  75                  80

Lys Asn Phe Thr Cys Gly Ser Met Gly Gln Lys Gly Lys Asp Trp Glu
                85                  90                  95

Ala Phe Pro Val His Val Val Ile Gly Met Ala Gly Gln Asp Trp Gln
            100                 105                 110

Pro Thr Trp Glu Pro Arg Pro Asp His Pro Thr Ile Pro Ser Thr His
        115                 120                 125

Asn Pro Lys Arg Ser Leu Tyr Arg Thr Gly Glu Phe Gly Tyr Thr Arg
    130                 135                 140

Leu Ile Ala Thr Lys Glu Lys Leu Thr Leu Ser Phe Val Gly Asn His
145                 150                 155                 160

Asp Gly Glu Val His Asp Met Val Glu Ile Leu Ala Ser Gly Gln Val
                165                 170                 175

Leu Asn Gly Gly Asp Asp Asn Asn Gly Lys Val Gly Ala Val His Lys
            180                 185                 190

Val Asp Asp Val Thr Arg Tyr Ser Phe Ser His Tyr Val Trp Gly Gly
        195                 200                 205

Ser Val Leu Val Leu Gly Gly Phe Val Gly Tyr Val Leu Gly Phe Val
    210                 215                 220

Ser His Ala Arg Arg Gln Ile Ala Thr Glu Arg Gly Trp Thr Ser Leu
225                 230                 235                 240
```

Lys Thr Glu Glu Gln
245

<210> SEQ ID NO 38
<211> LENGTH: 930
<212> TYPE: DNA
<213> ORGANISM: Panicum virgatum

<400> SEQUENCE: 38
tggccatcac aaccttggaa accatggtgg gctacatatg gaaaggacgg tgggggtgaa 60
tgtggaatac catacagtgt caagttcaga atgcctggca attcagttct acctactggt 120
aatggtggtc cagacaccag gaatctttat tactcctttg attcaggtgt ggtgcatttc 180
gtgtacatgt caactgaaac taattttctt cagggcagtg accagtacaa cttcttaaaa 240
gcggaccttg agaaggtgaa ccgaactaga acaccattcg ttgtttttca gggccaccgt 300
cccatgtaca cctcaagtga tgaaaccagg gatgctgctt tgaaacagca gatgctccag 360
aatttggaac cactgctggt gacatacaat gtgacccttg cactctgggg acatgtccac 420
aggtatgaga ggttctgccc catgaagaac ttccaatgtg ttaacacttc gtcaagcttc 480
caataccctg gcgcccctgt gcatcttgtg atcgggatgg gtggtcaaga ctggcaacct 540
atatggcaac caaggcctga tcaccctgat gttcccatct ttccgcagcc tgagaggtct 600
atgtaccgtg gtggtgtgtt tggatacaca agacttgtag ctacaaggga gaagctaaca 660
ctaacgtatg tggggaacca tgatgggcaa gtccatgata tggtggagat attttctggc 720
caagtatcca gcaacagcag tgttgctgag gctgttgatg gtgcaaaact cagcacagga 780
gtcagcaccg tgcgaaaaat gcctcctttg tacttggaaa tcggaggcag tgtgatgttt 840
gcactactgc tggggtttgg ttttggattt cttgtcagga gaaagaaaga agctgcacaa 900
tgggctccgg taaagaacga ggaatcttaa 930

<210> SEQ ID NO 39
<211> LENGTH: 309
<212> TYPE: PRT
<213> ORGANISM: Panicum virgatum

<400> SEQUENCE: 39

Trp Pro Ser Gln Pro Trp Lys Pro Trp Trp Ala Thr Tyr Gly Lys Asp
1 5 10 15

Gly Gly Gly Glu Cys Gly Ile Pro Tyr Ser Val Lys Phe Arg Met Pro
20 25 30

Gly Asn Ser Val Leu Pro Thr Gly Asn Gly Gly Pro Asp Thr Arg Asn
35 40 45

Leu Tyr Tyr Ser Phe Asp Ser Gly Val Val His Phe Val Tyr Met Ser
50 55 60

Thr Glu Thr Asn Phe Leu Gln Gly Ser Asp Gln Tyr Asn Phe Leu Lys
65 70 75 80

Ala Asp Leu Glu Lys Val Asn Arg Thr Arg Thr Pro Phe Val Val Phe
85 90 95

Gln Gly His Arg Pro Met Tyr Thr Ser Ser Asp Glu Thr Arg Asp Ala
100 105 110

Ala Leu Lys Gln Gln Met Leu Gln Asn Leu Glu Pro Leu Leu Val Thr
115 120 125

Tyr Asn Val Thr Leu Ala Leu Trp Gly His Val His Arg Tyr Glu Arg
130 135 140

```
Phe Cys Pro Met Lys Asn Phe Gln Cys Val Asn Thr Ser Ser Ser Phe
145                 150                 155                 160

Gln Tyr Pro Gly Ala Pro Val His Leu Val Ile Gly Met Gly Gly Gln
                165                 170                 175

Asp Trp Gln Pro Ile Trp Gln Pro Arg Pro Asp His Pro Asp Val Pro
            180                 185                 190

Ile Phe Pro Gln Pro Glu Arg Ser Met Tyr Arg Gly Gly Val Phe Gly
        195                 200                 205

Tyr Thr Arg Leu Val Ala Thr Arg Glu Lys Leu Thr Leu Thr Tyr Val
    210                 215                 220

Gly Asn His Asp Gly Gln Val His Asp Met Val Glu Ile Phe Ser Gly
225                 230                 235                 240

Gln Val Ser Ser Asn Ser Ser Val Ala Glu Ala Val Asp Gly Ala Lys
                245                 250                 255

Leu Ser Thr Gly Val Ser Thr Val Arg Lys Met Pro Pro Leu Tyr Leu
            260                 265                 270

Glu Ile Gly Gly Ser Val Met Phe Ala Leu Leu Leu Gly Phe Gly Phe
        275                 280                 285

Gly Phe Leu Val Arg Arg Lys Lys Glu Ala Ala Gln Trp Ala Pro Val
    290                 295                 300

Lys Asn Glu Glu Ser
305
```

<210> SEQ ID NO 40
<211> LENGTH: 1179
<212> TYPE: DNA
<213> ORGANISM: Solanum lycopersicum

<400> SEQUENCE: 40

```
gctttcttgt ttggagacat ggggactgct acgccatact tgacatttct tcgtacacag     60

gaagaaagta aatcaacgat taagtggata agccgtgata ttgaagctct tggtaataag    120

cctgccctta tctcacatat tggagatatc agctacgcca gaggatactc ttggttgtgg    180

gacaactttt ttactcaggt ggaacctgtt gcatccagag ttccatacca tgtatgcatc    240

ggaaaccatg aatatgattg gccacttcaa ccttggaagc ctgattggtc aagctacggg    300

aaagatgggg gaggtgaatg tggtgtaccc tacagtcata agttccatat gccaggaaac    360

tcttcagtgc cgactggaat gcatgctcct gcaactcgga atctttatta ctcatttgat    420

tctgggcccg ttcactttgt ctatatgtca actgaaacaa atttcctgcc aggtagtaac    480

cagtatgact ttttaaagca tgacttggaa tcagttgatc gagtaaaaac tccttttgtc    540

gtctttcaag ggcacagacc aatgtacagt tcaagtagcg gaacaaaaga tatatctttg    600

aggaagagaa tggttgagta tttggaacct cttcttgtga agaacaatgt gaatcttgta    660

ttgtgggggc atgttcatag gtatgagagg ttttgccctt tgaataactt cacctgtgga    720

agcttggcct tgaacgggaa ggagcaaaag gctttccctg ttcaaattgt gatcgggatg    780

gcaggacagg actggcagcc tatctgggca ccaagagaag accaccctac ggatcctatt    840

ttcccacagc ctctgcaatc tctgtaccgt gggagtgaat ttggatacat gaggctgcat    900

gccacaaagg aaaagcttac actttcttat gtaggaaacc atgacggaga ggtgcatgat    960

aaggtggagt tcctagcttc aggacaactt ctcaatgctg gtatccgtga tggtcctgca   1020

gatacagtac acatggagtc taacttctca tggtatgtaa aggttggaag tgtgctaatg   1080

cttggagctt tgatgggtta catagttgga ttcatatctc atgctcggaa aaattctgct   1140
```

```
gataatggtt ggaggcctat aaaaactgag gtaatatga                        1179


<210> SEQ ID NO 41
<211> LENGTH: 392
<212> TYPE: PRT
<213> ORGANISM: Solanum lycopersicum

<400> SEQUENCE: 41

Ala Phe Leu Phe Gly Asp Met Gly Thr Ala Thr Pro Tyr Leu Thr Phe
1               5                   10                  15

Leu Arg Thr Gln Glu Glu Ser Lys Ser Thr Ile Lys Trp Ile Ser Arg
            20                  25                  30

Asp Ile Glu Ala Leu Gly Asn Lys Pro Ala Leu Ile Ser His Ile Gly
        35                  40                  45

Asp Ile Ser Tyr Ala Arg Gly Tyr Ser Trp Leu Trp Asp Asn Phe Phe
    50                  55                  60

Thr Gln Val Glu Pro Val Ala Ser Arg Val Pro Tyr His Val Cys Ile
65                  70                  75                  80

Gly Asn His Glu Tyr Asp Trp Pro Leu Gln Pro Trp Lys Pro Asp Trp
                85                  90                  95

Ser Ser Tyr Gly Lys Asp Gly Gly Gly Glu Cys Gly Val Pro Tyr Ser
            100                 105                 110

His Lys Phe His Met Pro Gly Asn Ser Ser Val Pro Thr Gly Met His
        115                 120                 125

Ala Pro Ala Thr Arg Asn Leu Tyr Tyr Ser Phe Asp Ser Gly Pro Val
    130                 135                 140

His Phe Val Tyr Met Ser Thr Glu Thr Asn Phe Leu Pro Gly Ser Asn
145                 150                 155                 160

Gln Tyr Asp Phe Leu Lys His Asp Leu Glu Ser Val Asp Arg Val Lys
                165                 170                 175

Thr Pro Phe Val Val Phe Gln Gly His Arg Pro Met Tyr Ser Ser Ser
            180                 185                 190

Ser Gly Thr Lys Asp Ile Ser Leu Arg Lys Arg Met Val Glu Tyr Leu
        195                 200                 205

Glu Pro Leu Leu Val Lys Asn Asn Val Asn Leu Val Leu Trp Gly His
    210                 215                 220

Val His Arg Tyr Glu Arg Phe Cys Pro Leu Asn Asn Phe Thr Cys Gly
225                 230                 235                 240

Ser Leu Ala Leu Asn Gly Lys Glu Gln Lys Ala Phe Pro Val Gln Ile
                245                 250                 255

Val Ile Gly Met Ala Gly Gln Asp Trp Gln Pro Ile Trp Ala Pro Arg
            260                 265                 270

Glu Asp His Pro Thr Asp Pro Ile Phe Pro Gln Pro Leu Gln Ser Leu
        275                 280                 285

Tyr Arg Gly Ser Glu Phe Gly Tyr Met Arg Leu His Ala Thr Lys Glu
    290                 295                 300

Lys Leu Thr Leu Ser Tyr Val Gly Asn His Asp Gly Glu Val His Asp
305                 310                 315                 320

Lys Val Glu Phe Leu Ala Ser Gly Gln Leu Leu Asn Ala Gly Ile Arg
                325                 330                 335

Asp Gly Pro Ala Asp Thr Val His Met Glu Ser Asn Phe Ser Trp Tyr
            340                 345                 350

Val Lys Val Gly Ser Val Leu Met Leu Gly Ala Leu Met Gly Tyr Ile
        355                 360                 365
```

```
Val Gly Phe Ile Ser His Ala Arg Lys Asn Ser Ala Asp Asn Gly Trp
    370                 375                 380

Arg Pro Ile Lys Thr Glu Val Ile
385                 390


<210> SEQ ID NO 42
<211> LENGTH: 406
<212> TYPE: DNA
<213> ORGANISM: Sorghum bicolor

<400> SEQUENCE: 42

accatgacca gaacccatat ggcaaccgag gcccgatcac ccagatgtcc ccatctttcc      60

acagcctgag aggtccatgt accgtggcgg tgagtttgga tacacaaggc ttgtagcaac     120

aagggagaag ctaacattaa cctatgtggg gaaccatgat gggcaagtcc atggtatggt     180

ggagatattt tctggcctgg tatccagtaa cagtagtgtt gctgtggcag tgcatgacac     240

caaacttggc acagaagtca gcaccgtgcg aaaaatatct ccattgtact tggaaatcgg     300

aggcagtgta ttgtttgcac tgctcctggg attttccttt ggatttctta tcaggagaaa     360

ggaagaagct gcacagtgga ctccagtaaa gaacgaggaa tcataa                    406


<210> SEQ ID NO 43
<211> LENGTH: 130
<212> TYPE: PRT
<213> ORGANISM: Sorghum bicolor

<400> SEQUENCE: 43

Pro Ile Trp Gln Pro Arg Pro Asp His Pro Asp Val Pro Ile Phe Pro
1               5                   10                  15

Gln Pro Glu Arg Ser Met Tyr Arg Gly Gly Glu Phe Gly Tyr Thr Arg
            20                  25                  30

Leu Val Ala Thr Arg Glu Lys Leu Thr Leu Thr Tyr Val Gly Asn His
        35                  40                  45

Asp Gly Gln Val His Gly Met Val Glu Ile Phe Ser Gly Leu Val Ser
    50                  55                  60

Ser Asn Ser Ser Val Ala Val Ala Val His Asp Thr Lys Leu Gly Thr
65                  70                  75                  80

Glu Val Ser Thr Val Arg Lys Ile Ser Pro Leu Tyr Leu Glu Ile Gly
                85                  90                  95

Gly Ser Val Leu Phe Ala Leu Leu Leu Gly Phe Ser Phe Gly Phe Leu
            100                 105                 110

Ile Arg Arg Lys Glu Glu Ala Ala Gln Trp Thr Pro Val Lys Asn Glu
        115                 120                 125

Glu Ser
    130


<210> SEQ ID NO 44
<211> LENGTH: 960
<212> TYPE: DNA
<213> ORGANISM: Triticum aestivum

<400> SEQUENCE: 44

catgtctgca taggaaatca tgagtatgat tggccttcac aaccttggaa accttcgtgg      60

tctacatatg gaaaggatgg tggaggtgaa tgcggaatac catacagtgt caagttcagg     120

atgcctggga attctgttct acctactggc aatggagctc cggacacacg gaatctctat     180

tactcttttg attcaggtgt tgtgcatttt gtgtacatgt cgactgaaac taatttcgtt     240
```

```
cagggcagcg accaacacaa tttcctaaaa gctgacctag agaaggtgaa ccgaagtaga    300

accccatttg ttgtgtttca gggccaccgg cccatgtata cctcgagcaa cgaagccagg    360

gattttgcca tgagacagca gatgatccag catcttgaac tgctcttggt gatgtacaat    420

gtgacccttg ccctgtgggg acatgtccat aggtatgaga ggttctgccc catgaagaat    480

tcacagtgtc tgaacacatc atcaagcttc atataccctg gtgcccctgt tcatgttgtg    540

atcgggatgg ccggacaaga ctggcaaccg atctggcaac caaggcgtga tcatccagat    600

gttcccatct ttccacagcc tgggatctcc atgtaccgtg gtggtgagtt cgggtacaca    660

aaactggtag ctaccaggga gaagctaacg ctgatgtacg tcgggaacca tgacggacaa    720

gtccatgaca tggtggagat attctctgga caaacatcta ctgaagctag tgctaccgag    780

gcggtcaatc aaacaaagct cggctcggga accagcgcca agctgaagat ttccccatta    840

tacttggaaa ttggaggtag tgtgatgttg gcattgctgc ttggttttgc cttgggattt    900

ctcctcagga agaagagaga agcggcacaa tggactccgg tgaagaacga ggaatcctaa    960
```

```
<210> SEQ ID NO 45
<211> LENGTH: 319
<212> TYPE: PRT
<213> ORGANISM: Triticum aestivum

<400> SEQUENCE: 45

His Val Cys Ile Gly Asn His Glu Tyr Asp Trp Pro Ser Gln Pro Trp
1               5                   10                  15

Lys Pro Ser Trp Ser Thr Tyr Gly Lys Asp Gly Gly Gly Glu Cys Gly
            20                  25                  30

Ile Pro Tyr Ser Val Lys Phe Arg Met Pro Gly Asn Ser Val Leu Pro
        35                  40                  45

Thr Gly Asn Gly Ala Pro Asp Thr Arg Asn Leu Tyr Tyr Ser Phe Asp
    50                  55                  60

Ser Gly Val Val His Phe Val Tyr Met Ser Thr Glu Thr Asn Phe Val
65                  70                  75                  80

Gln Gly Ser Asp Gln His Asn Phe Leu Lys Ala Asp Leu Glu Lys Val
                85                  90                  95

Asn Arg Ser Arg Thr Pro Phe Val Val Phe Gln Gly His Arg Pro Met
            100                 105                 110

Tyr Thr Ser Ser Asn Glu Ala Arg Asp Phe Ala Met Arg Gln Gln Met
        115                 120                 125

Ile Gln His Leu Glu Leu Leu Leu Val Met Tyr Asn Val Thr Leu Ala
    130                 135                 140

Leu Trp Gly His Val His Arg Tyr Glu Arg Phe Cys Pro Met Lys Asn
145                 150                 155                 160

Ser Gln Cys Leu Asn Thr Ser Ser Ser Phe Ile Tyr Pro Gly Ala Pro
                165                 170                 175

Val His Val Val Ile Gly Met Ala Gly Gln Asp Trp Gln Pro Ile Trp
            180                 185                 190

Gln Pro Arg Arg Asp His Pro Asp Val Pro Ile Phe Pro Gln Pro Gly
        195                 200                 205

Ile Ser Met Tyr Arg Gly Gly Glu Phe Gly Tyr Thr Lys Leu Val Ala
    210                 215                 220

Thr Arg Glu Lys Leu Thr Leu Met Tyr Val Gly Asn His Asp Gly Gln
225                 230                 235                 240

Val His Asp Met Val Glu Ile Phe Ser Gly Gln Thr Ser Thr Glu Ala
                245                 250                 255
```

```
Ser Ala Thr Glu Ala Val Asn Gln Thr Lys Leu Gly Ser Gly Thr Ser
            260                 265                 270

Ala Lys Leu Lys Ile Ser Pro Leu Tyr Leu Glu Ile Gly Gly Ser Val
        275                 280                 285

Met Leu Ala Leu Leu Leu Gly Phe Ala Leu Gly Phe Leu Leu Arg Lys
    290                 295                 300

Lys Arg Glu Ala Ala Gln Trp Thr Pro Val Lys Asn Glu Glu Ser
305                 310                 315


<210> SEQ ID NO 46
<211> LENGTH: 1959
<212> TYPE: DNA
<213> ORGANISM: Brassica napus

<400> SEQUENCE: 46

atgatcgtcg acttctctac cttcatcctc ttcatctccg tcttcatttc ctcagctaac      60

gccaaagcaa ccttatccat ctcccccaaa actctaagcc gatccggcga ttccatcctc     120

atcaaatggt ccaacgtcga ctctccctcc gatctcgact ggctaggcat ctactccccc     180

ccagactctc cccacgacca cttcatcggc tacaaattcc tcaacgtctc ccccacgtgg     240

caatccggct ccggcgcgat ctccctcccc ctcaccaacc tccgatcgaa ctacacgttc     300

cgtatcttcc gatggacgca gtccgagatc aatccgaagc acaaggacca cgaccagaat     360

cccttaccgg gaacgaagca ccttctggcg gaatcggagc aggtggggtt cggatccgcc     420

ggcgtgggga ggccggagca gatccatttg gcgttcgagg ataaggttaa caggatgcgg     480

gtcacgttcg tagctgggga tggggaagaa aggttcgtga ggtacggaga ggggaaggac     540

gcgttggcga actccgcggc ggcgcgcggg attaggtacg agagggagca tatgtgtaat     600

gctccggcta attccaccgt gggatggaga gatcccgggt ggatttttca taccgttatg     660

aagaatttga acggtggcgt taggtattat tatcaggttg ggagtgattc aaagggatgg     720

agtgagatcc acagctttat cgctcgagat atctactcag aagaaaccat agctttcatg     780

ttcggagaca tgggttgcgc tacaccttac aataccttta tccggacgca ggacgagagt     840

atctcaacag ttaagtggat actccgcgac atcgaagctc ttggtgacaa gccagctctt     900

gtttcgcaca ttggtgatat aagctacgct cgtggttact cgtgggtgtg ggatgagttc     960

ttcgctcaga tcgagcctat tgcctcgaga gttccttacc acgtctgcat tggtaaccac    1020

gagtatgact tccctactca gccgtggaaa cctgattggg gaacttacgg taatgacggt    1080

gggggagagt gcggtgtgcc gtatagtctc aagttcaaca tgcctggaaa ctcgtcggaa    1140

ccaacgggaa cgaaagctcc tcctacaagg aatttgtatt actcttacga catggggtcg    1200

gttcatttcc tttacatctc caccgagacg aactttctca aggagggagc gcaatacgag    1260

tttataaagc gagatcttga gtctgtgaac agggagaaaa caccgtttgt tgtcgtgcaa    1320

ggacacagac cgatgtacac cacgagcaac gaggtgagag acgcgatgat taggcaaaag    1380

atggtggagc atttggagcc gctgtttgtg gagaacaacg tgacgcttgc tctgtgggga    1440

catgttcata gatacgagag gttttgtccg ataagcaaca acacgtgtgg gaaacagtgg    1500

agaggaagcc cggttcatct tgtgatcggt atgggcggtc aagactggca accgatttgg    1560

cagccgagac cgaaccatcc gggtcttcct atattccctc agcctgaaca gtcgatgtac    1620

aggacgggtg agtttgggta cactcgtttg gttgcgaaca aagagaagct tactgtttcg    1680

tttgtgggta accatgatgg agaagttcat gatagtgttg agatcttagc gtctggggaa    1740
```

```
gtaatcagtg ggaggaaaga ggaaactatt aagaccgttc ctgtatctgc aacacttgtg   1800

gggaaacctg agtctgatgt cttatggtat gttaaaggag caggcttgtt ggttatgggt   1860

gtgcttttag ggttccttat agggtttttt acaaggggga agaaaggatc ttcttcatct   1920

gataaccgtt ggatcccagt caagaacgag gagacatga                          1959


<210> SEQ ID NO 47
<211> LENGTH: 652
<212> TYPE: PRT
<213> ORGANISM: Brassica napus

<400> SEQUENCE: 47

Met Ile Val Asp Phe Ser Thr Phe Ile Leu Phe Ile Ser Val Phe Ile
1               5                   10                  15

Ser Ser Ala Asn Ala Lys Ala Thr Leu Ser Ile Ser Pro Lys Thr Leu
            20                  25                  30

Ser Arg Ser Gly Asp Ser Ile Leu Ile Lys Trp Ser Asn Val Asp Ser
        35                  40                  45

Pro Ser Asp Leu Asp Trp Leu Gly Ile Tyr Ser Pro Pro Asp Ser Pro
    50                  55                  60

His Asp His Phe Ile Gly Tyr Lys Phe Leu Asn Val Ser Pro Thr Trp
65                  70                  75                  80

Gln Ser Gly Ser Gly Ala Ile Ser Leu Pro Leu Thr Asn Leu Arg Ser
                85                  90                  95

Asn Tyr Thr Phe Arg Ile Phe Arg Trp Thr Gln Ser Glu Ile Asn Pro
            100                 105                 110

Lys His Lys Asp His Asp Gln Asn Pro Leu Pro Gly Thr Lys His Leu
        115                 120                 125

Leu Ala Glu Ser Glu Gln Val Gly Phe Gly Ser Ala Gly Val Gly Arg
    130                 135                 140

Pro Glu Gln Ile His Leu Ala Phe Glu Asp Lys Val Asn Arg Met Arg
145                 150                 155                 160

Val Thr Phe Val Ala Gly Asp Gly Glu Glu Arg Phe Val Arg Tyr Gly
                165                 170                 175

Glu Gly Lys Asp Ala Leu Ala Asn Ser Ala Ala Ala Arg Gly Ile Arg
            180                 185                 190

Tyr Glu Arg Glu His Met Cys Asn Ala Pro Ala Asn Ser Thr Val Gly
        195                 200                 205

Trp Arg Asp Pro Gly Trp Ile Phe His Thr Val Met Lys Asn Leu Asn
    210                 215                 220

Gly Gly Val Arg Tyr Tyr Tyr Gln Val Gly Ser Asp Ser Lys Gly Trp
225                 230                 235                 240

Ser Glu Ile His Ser Phe Ile Ala Arg Asp Ile Tyr Ser Glu Glu Thr
                245                 250                 255

Ile Ala Phe Met Phe Gly Asp Met Gly Cys Ala Thr Pro Tyr Asn Thr
            260                 265                 270

Phe Ile Arg Thr Gln Asp Glu Ser Ile Ser Thr Val Lys Trp Ile Leu
        275                 280                 285

Arg Asp Ile Glu Ala Leu Gly Asp Lys Pro Ala Leu Val Ser His Ile
    290                 295                 300

Gly Asp Ile Ser Tyr Ala Arg Gly Tyr Ser Trp Val Trp Asp Glu Phe
305                 310                 315                 320

Phe Ala Gln Ile Glu Pro Ile Ala Ser Arg Val Pro Tyr His Val Cys
                325                 330                 335
```

```
Ile Gly Asn His Glu Tyr Asp Phe Pro Thr Gln Pro Trp Lys Pro Asp
            340                 345                 350

Trp Gly Thr Tyr Gly Asn Asp Gly Gly Gly Glu Cys Gly Val Pro Tyr
        355                 360                 365

Ser Leu Lys Phe Asn Met Pro Gly Asn Ser Ser Glu Pro Thr Gly Thr
    370                 375                 380

Lys Ala Pro Pro Thr Arg Asn Leu Tyr Tyr Ser Tyr Asp Met Gly Ser
385                 390                 395                 400

Val His Phe Leu Tyr Ile Ser Thr Glu Thr Asn Phe Leu Lys Gly Gly
                405                 410                 415

Arg Gln Tyr Glu Phe Ile Lys Arg Asp Leu Glu Ser Val Asn Arg Glu
            420                 425                 430

Lys Thr Pro Phe Val Val Val Gln Gly His Arg Pro Met Tyr Thr Thr
        435                 440                 445

Ser Asn Glu Val Arg Asp Ala Met Ile Arg Gln Lys Met Val Glu His
    450                 455                 460

Leu Glu Pro Leu Phe Val Glu Asn Asn Val Thr Leu Ala Leu Trp Gly
465                 470                 475                 480

His Val His Arg Tyr Glu Arg Phe Cys Pro Ile Ser Asn Asn Thr Cys
                485                 490                 495

Gly Lys Gln Trp Arg Gly Ser Pro Val His Leu Val Ile Gly Met Gly
            500                 505                 510

Gly Gln Asp Trp Gln Pro Ile Trp Gln Pro Arg Pro Asn His Pro Gly
        515                 520                 525

Leu Pro Ile Phe Pro Gln Pro Glu Gln Ser Met Tyr Arg Thr Gly Glu
    530                 535                 540

Phe Gly Tyr Thr Arg Leu Val Ala Asn Lys Glu Lys Leu Thr Val Ser
545                 550                 555                 560

Phe Val Gly Asn His Asp Gly Glu Val His Asp Ser Val Glu Ile Leu
                565                 570                 575

Ala Ser Gly Glu Val Ile Ser Gly Arg Lys Glu Glu Thr Ile Lys Thr
            580                 585                 590

Val Pro Val Ser Ala Thr Leu Val Gly Lys Pro Glu Ser Asp Val Leu
        595                 600                 605

Trp Tyr Val Lys Gly Ala Gly Leu Leu Val Met Gly Val Leu Leu Gly
    610                 615                 620

Phe Leu Ile Gly Phe Phe Thr Arg Gly Lys Lys Gly Ser Ser Ser Ser
625                 630                 635                 640

Asp Asn Arg Trp Ile Pro Val Lys Asn Glu Glu Thr
                645                 650


<210> SEQ ID NO 48
<211> LENGTH: 4
<212> TYPE: PRT
<213> ORGANISM: Arabidopsis thaliana
<220> FEATURE:
<221> NAME/KEY: MISC_FEATURE
<222> LOCATION: (3)..(4)
<223> OTHER INFORMATION: Xaa is any amino acid

<400> SEQUENCE: 48

Gly Asp Xaa Gly
1


<210> SEQ ID NO 49
<211> LENGTH: 5
<212> TYPE: PRT
```

<213> ORGANISM: Artificial Sequence
<220> FEATURE:
<223> OTHER INFORMATION: Sequence from plant purple acid phosphatases
      found in plant species such as Arabidopsis thaliana
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(4)
<223> OTHER INFORMATION: Xaa is any amino acid

<400> SEQUENCE: 49

Xaa Asp Xaa Xaa Tyr
1               5

<210> SEQ ID NO 50
<211> LENGTH: 4
<212> TYPE: PRT
<213> ORGANISM: Arabidopsis thaliana

<400> SEQUENCE: 50

Gly Asn His Asp
1

<210> SEQ ID NO 51
<211> LENGTH: 4
<212> TYPE: PRT
<213> ORGANISM: Arabidopsis thaliana

<400> SEQUENCE: 51

Gly Asn His Glu
1

<210> SEQ ID NO 52
<211> LENGTH: 4
<212> TYPE: PRT
<213> ORGANISM: Artificial Sequence
<220> FEATURE:
<223> OTHER INFORMATION: Sequence from plant purple acid phosphatases
      found in plant species such as Arabidopsis thaliana
<220> FEATURE:
<221> NAME/KEY: MISC_FEATURE
<222> LOCATION: (1)..(1)
<223> OTHER INFORMATION: Xaa is Leu, Ile, Val, Phe, or Met
<220> FEATURE:
<221> NAME/KEY: MISC_FEATURE
<222> LOCATION: (2)..(2)
<223> OTHER INFORMATION: Xaa is any amino acid

<400> SEQUENCE: 52

Xaa Xaa Gly His
1

<210> SEQ ID NO 53
<211> LENGTH: 4
<212> TYPE: PRT
<213> ORGANISM: Artificial Sequence
<220> FEATURE:
<223> OTHER INFORMATION: Sequence from plant purple acid phosphatases
      found in plant species such as Arabidopsis thaliana
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid

<400> SEQUENCE: 53

Xaa His Xaa His
1

<210> SEQ ID NO 54
<211> LENGTH: 12
<212> TYPE: PRT
<213> ORGANISM: Arabidopsis thaliana
<220> FEATURE:
<221> NAME/KEY: MISC_FEATURE
<222> LOCATION: (12)..(12)
<223> OTHER INFORMATION: Xaa is Phe or Trp

<400> SEQUENCE: 54

Tyr His Val Cys Ile Gly Asn His Glu Tyr Asp Xaa
1 5 10

<210> SEQ ID NO 55
<211> LENGTH: 12
<212> TYPE: PRT
<213> ORGANISM: Artificial Sequence
<220> FEATURE:
<223> OTHER INFORMATION: Sequence from plant purple acid phosphatases found in plant species such as Arabidopsis thaliana
<220> FEATURE:
<221> NAME/KEY: MISC_FEATURE
<222> LOCATION: (12)..(12)
<223> OTHER INFORMATION: Xaa is Phe or Trp

<400> SEQUENCE: 55

Tyr His Val Cys Ile Gly Asn His Glu Tyr Asn Xaa
1 5 10

<210> SEQ ID NO 56
<211> LENGTH: 13
<212> TYPE: PRT
<213> ORGANISM: Arabidopsis thaliana

<400> SEQUENCE: 56

His Ile Gly Asp Ile Ser Tyr Ala Arg Gly Tyr Ser Trp
1 5 10

<210> SEQ ID NO 57
<211> LENGTH: 18
<212> TYPE: PRT
<213> ORGANISM: Arabidopsis thaliana

<400> SEQUENCE: 57

Lys Glu Lys Leu Thr Val Ser Phe Val Gly Asn His Asp Gly Glu Val
1 5 10 15

His Asp

<210> SEQ ID NO 58
<211> LENGTH: 18
<212> TYPE: PRT
<213> ORGANISM: Artificial Sequence
<220> FEATURE:
<223> OTHER INFORMATION: Sequence derived from plant purple acid phosphatases found in plant species such as Arabidopsis thaliana

<400> SEQUENCE: 58

Lys Glu Arg Leu Thr Leu Ser Tyr Val Gly Asn His Asp Gly Glu Val
1 5 10 15

His Asp

```
<210> SEQ ID NO 59
<211> LENGTH: 18
<212> TYPE: PRT
<213> ORGANISM: Zea mays

<400> SEQUENCE: 59

Arg Glu Lys Leu Thr Leu Thr Tyr Val Gly Asn His Asp Gly Gln Val
1               5                   10                  15

His Asp


<210> SEQ ID NO 60
<211> LENGTH: 18
<212> TYPE: PRT
<213> ORGANISM: Artificial Sequence
<220> FEATURE:
<223> OTHER INFORMATION: Sequence derived from plant purple acid
      phosphatases found in plant species such as Arabidopsis thaliana

<400> SEQUENCE: 60

Lys Glu Lys Leu Thr Leu Thr Tyr Ile Gly Asn His Asp Gly Gln Val
1               5                   10                  15

His Asp


<210> SEQ ID NO 61
<211> LENGTH: 10
<212> TYPE: PRT
<213> ORGANISM: Arabidopsis thaliana
<220> FEATURE:
<221> NAME/KEY: MISC_FEATURE
<222> LOCATION: (8)..(9)
<223> OTHER INFORMATION: Xaa is any amino acid

<400> SEQUENCE: 61

Phe Val Gly Asn His Asp Gly Xaa Xaa His
1               5                   10


<210> SEQ ID NO 62
<211> LENGTH: 10
<212> TYPE: PRT
<213> ORGANISM: Artificial Sequence
<220> FEATURE:
<223> OTHER INFORMATION: Sequence derived from plant purple acid
      phosphatases found in plant species such as Arabidopsis thaliana
<220> FEATURE:
<221> NAME/KEY: MISC_FEATURE
<222> LOCATION: (8)..(9)
<223> OTHER INFORMATION: Xaa is any amino acid

<400> SEQUENCE: 62

Phe Ile Gly Asn His Asp Gly Xaa Xaa His
1               5                   10


<210> SEQ ID NO 63
<211> LENGTH: 10
<212> TYPE: PRT
<213> ORGANISM: Zea mays
<220> FEATURE:
<221> NAME/KEY: MISC_FEATURE
<222> LOCATION: (8)..(9)
<223> OTHER INFORMATION: Xaa is any amino acid

<400> SEQUENCE: 63

Tyr Val Gly Asn His Asp Gly Xaa Xaa His
1               5                   10


<210> SEQ ID NO 64
<211> LENGTH: 10
```

```
<212> TYPE: PRT
<213> ORGANISM: Artificial Sequence
<220> FEATURE:
<223> OTHER INFORMATION: Sequence derived from plant purple acid
      phosphatases found in plant species such as Arabidopsis thaliana
<220> FEATURE:
<221> NAME/KEY: MISC_FEATURE
<222> LOCATION: (8)..(9)
<223> OTHER INFORMATION: Xaa is any amino acid

<400> SEQUENCE: 64

Tyr Ile Gly Asn His Asp Gly Xaa Xaa His
1               5                   10


<210> SEQ ID NO 65
<211> LENGTH: 23
<212> TYPE: PRT
<213> ORGANISM: Arabidopsis thaliana

<400> SEQUENCE: 65

Leu Trp Tyr Ala Lys Gly Ala Gly Leu Met Val Val Gly Val Leu Leu
1               5                   10                  15

Gly Phe Ile Ile Gly Phe Phe
            20


<210> SEQ ID NO 66
<211> LENGTH: 12
<212> TYPE: PRT
<213> ORGANISM: Artificial Sequence
<220> FEATURE:
<223> OTHER INFORMATION: Sequence derived from plant purple acid
      phosphatases found in plant species such as Arabidopsis thaliana
<220> FEATURE:
<221> NAME/KEY: MISC_FEATURE
<222> LOCATION: (1)..(2)
<223> OTHER INFORMATION: Xaa  is Leu, M, or V
<220> FEATURE:
<221> NAME/KEY: MISC_FEATURE
<222> LOCATION: (3)..(3)
<223> OTHER INFORMATION: Xaa  is Leu, Ile, Val, Phe, or Met
<220> FEATURE:
<221> NAME/KEY: MISC_FEATURE
<222> LOCATION: (4)..(4)
<223> OTHER INFORMATION: Xaa  is Gly or Ala
<220> FEATURE:
<221> NAME/KEY: MISC_FEATURE
<222> LOCATION: (5)..(5)
<223> OTHER INFORMATION: Xaa  is Val, Ala, or Leu
<220> FEATURE:
<221> NAME/KEY: MISC_FEATURE
<222> LOCATION: (6)..(7)
<223> OTHER INFORMATION: Xaa  is Leu, Ile, Val, Phe, or Met
<220> FEATURE:
<221> NAME/KEY: MISC_FEATURE
<222> LOCATION: (9)..(9)
<223> OTHER INFORMATION: Xaa  is Phe or Tyr
<220> FEATURE:
<221> NAME/KEY: MISC_FEATURE
<222> LOCATION: (10)..(10)
<223> OTHER INFORMATION: Xaa  is any amino acid residue
<220> FEATURE:
<221> NAME/KEY: MISC_FEATURE
<222> LOCATION: (11)..(11)
<223> OTHER INFORMATION: Xaa  is Leu, Ile, Val, Phe, or Met

<400> SEQUENCE: 66

Xaa Xaa Xaa Xaa Xaa Xaa Xaa Gly Xaa Xaa Xaa Gly
1               5                   10


<210> SEQ ID NO 67
<211> LENGTH: 529
<212> TYPE: PRT
```

<213> ORGANISM: Arabidopsis thaliana

<400> SEQUENCE: 67

Met Thr Phe Leu Leu Leu Leu Leu Phe Cys Phe Leu Ser Pro Ala Ile
1 5 10 15

Ser Ser Ala His Ser Ile Pro Ser Thr Leu Asp Gly Pro Phe Val Pro
20 25 30

Val Thr Val Pro Leu Asp Thr Ser Leu Arg Gly Gln Ala Ile Asp Leu
35 40 45

Pro Asp Thr Asp Pro Arg Val Arg Arg Arg Val Ile Gly Phe Glu Pro
50 55 60

Glu Gln Ile Ser Leu Ser Leu Ser Ser Asp His Asp Ser Ile Trp Val
65 70 75 80

Ser Trp Ile Thr Gly Glu Phe Gln Ile Gly Lys Lys Val Lys Pro Leu
85 90 95

Asp Pro Thr Ser Ile Asn Ser Val Val Gln Phe Gly Thr Leu Arg His
100 105 110

Ser Leu Ser His Glu Ala Lys Gly His Ser Leu Val Tyr Ser Gln Leu
115 120 125

Tyr Pro Phe Asp Gly Leu Leu Asn Tyr Thr Ser Gly Ile Ile His His
130 135 140

Val Arg Ile Thr Gly Leu Lys Pro Ser Thr Ile Tyr Tyr Tyr Arg Cys
145 150 155 160

Gly Asp Pro Ser Arg Arg Ala Met Ser Lys Ile His His Phe Arg Thr
165 170 175

Met Pro Val Ser Ser Pro Ser Ser Tyr Pro Gly Arg Ile Ala Val Val
180 185 190

Gly Asp Leu Gly Leu Thr Tyr Asn Thr Thr Asp Thr Ile Ser His Leu
195 200 205

Ile His Asn Ser Pro Asp Leu Ile Leu Leu Ile Gly Asp Val Ser Tyr
210 215 220

Ala Asn Leu Tyr Leu Thr Asn Gly Thr Ser Ser Asp Cys Tyr Ser Cys
225 230 235 240

Ser Phe Pro Glu Thr Pro Ile His Glu Thr Tyr Gln Pro Arg Trp Asp
245 250 255

Tyr Trp Gly Arg Phe Met Glu Asn Leu Thr Ser Lys Val Pro Leu Met
260 265 270

Val Ile Glu Gly Asn His Glu Ile Glu Leu Gln Ala Glu Asn Lys Thr
275 280 285

Phe Glu Ala Tyr Ser Ser Arg Phe Ala Phe Pro Phe Asn Glu Ser Gly
290 295 300

Ser Ser Ser Thr Leu Tyr Tyr Ser Phe Asn Ala Gly Gly Ile His Phe
305 310 315 320

Val Met Leu Gly Ala Tyr Ile Ala Tyr Asp Lys Ser Ala Glu Gln Tyr
325 330 335

Glu Trp Leu Lys Lys Asp Leu Ala Lys Val Asp Arg Ser Val Thr Pro
340 345 350

Trp Leu Val Ala Ser Trp His Pro Pro Trp Tyr Ser Ser Tyr Thr Ala
355 360 365

His Tyr Arg Glu Ala Glu Cys Met Lys Glu Ala Met Glu Glu Leu Leu
370 375 380

Tyr Ser Tyr Gly Thr Asp Ile Val Phe Asn Gly His Val His Ala Tyr
385 390 395 400

-continued

```
Glu Arg Ser Asn Arg Val Tyr Asn Tyr Glu Leu Asp Pro Cys Gly Pro
                405                 410                 415

Val Tyr Ile Val Ile Gly Asp Gly Gly Asn Arg Glu Lys Met Ala Ile
            420                 425                 430

Glu His Ala Asp Asp Pro Gly Lys Cys Pro Glu Pro Leu Thr Thr Pro
        435                 440                 445

Asp Pro Val Met Gly Gly Phe Cys Ala Trp Asn Phe Thr Pro Ser Asp
    450                 455                 460

Lys Phe Cys Trp Asp Arg Gln Pro Asp Tyr Ser Ala Leu Arg Glu Ser
465                 470                 475                 480

Ser Phe Gly His Gly Ile Leu Glu Met Lys Asn Glu Thr Trp Ala Leu
                485                 490                 495

Trp Thr Trp Tyr Arg Asn Gln Asp Ser Ser Ser Glu Val Gly Asp Gln
            500                 505                 510

Ile Tyr Ile Val Arg Gln Pro Asp Arg Cys Pro Leu His His Arg Leu
        515                 520                 525

Val
```

METHOD FOR SPEEDING UP PLANT GROWTH AND IMPROVING YIELD BY INTRODUCING PHOSPHATASES IN TRANSGENIC PLANT

RELATED APPLICATIONS

This application is a divisional of U.S. application Ser. No. 12/640,674 filed Dec. 17, 2009, which claims priority to provisional application Ser. No. 61/138,918, filed on Dec. 18, 2008, the disclosures of which are incorporated herein by reference.

INCORPORATION OF SEQUENCE LISTING

A computer readable form of the sequence listing is contained in the file named "VRST002USD1_ST25.txt" which is 143 kb (measured in MS-Windows) and was created on Jul. 9, 2013, which is filed herewith and herein incorporated by reference.

1. TECHNICAL FIELD

The present disclosure provides methods that speeds up plant growth and elevates plant yields by introducing phosphatases with a C-terminal motif into plants. The present disclosure relates to phosphatases with a C-terminal motif, and their respectively encoded protein products, as well as fragments, derivatives, homologues, and variants thereof. Methods for introducing these genes into plants to (1) speed up the growth rate of plants, (2) to increase the sugar contents of plants, and (3) to increase of yield of plants, are provided.

2. BACKGROUND

Purple acid phosphatases (PAPs) catalyze the hydrolysis of a wide range of activated phosphoric acid mono- and di-esters and anhydrides (Klabunde et al., 1996). The PAP proteins are characterized by seven conserved amino acid residues (shown in bold face) in the five conserved motifs XDXX, XDXXY, GNH(D/E), XXXH, XHXH, which are involved in the coordination of the dimetal nuclear center ($Fe^{3+}$-$Me^{2+}$) in the active site (Li et al., 2002), where Me is a transition metal and $Me^{2+}$ is mostly found to be $Fe^{2+}$ in mammalian, and $Zn^{2+}$, or $Mn^{2+}$ in plants (Klabunde and Krebs, 1997; Schenk et al., 1999).

Purple acid phosphatases are distinguished from the other phosphatases by their characteristic purple color, which is caused by a charge transfer transition at 560 nm from a metal-coordinating tyrosine to the metal ligand $Fe^{3+}$ (Klabunde and Krebs, 1997; Schenk et al., 2000). Different from the other acid phosphatases, PAPs are insensitive to inhibition by tartrate, so they are also known as tartrate-resistant acid phosphatases (TRAPs).

The biochemical properties of some plant PAPs have been characterized, firstly in red kidney bean, and later in soybean suspension cell, soybean seedlings, rice culture cells, spinach leaves, sweet potato tubers, tomato, yellow lupin seeds, *medicago* and *Arabidopsis*, etc. (Schenk et al., 1999). Plant PAPs are generally considered to mediate phosphorus acquisition and redistribution based on their ability to hydrolyze phosphate compounds (Cashikar et al., 1997; Bozzo et al., 2004; Lung et al., 2008). Regulation of some plant PAPs transcripts by external phosphate level in medium or soil, strongly suggest their involving in phosphate acquisition. For example, the transcription level of *Medicago* MtPAP1 in roots was increased under P stress, implicating a role in P acquisition or internal mobilization (Xiao et al., 2005; Xiao et al., 2006). Some plant PAPs could be secreted from root cells to extracellular environment, then hydrolyze various phosphate esters. Lung et al. purified a secreted PAP phosphatase from tobacco, which could hydrolyze broad substrates and help to alleviate P starvation (Lung et al., 2008). Certain plant PAPs can also hydrolyze phytate, a major storage compound of phosphorus in plants. Hegeman and Grabeu (2001) purified a novel PAPs (GmPhy) from the cotyledon of the germinating soybean seedlings. GmPhy was introduced into soybean tissue culture and was assayed to show phosphatase activity. Most recently, AtPAP15 and 23 in *Arabidopsis* sharing high sequence homology (73-52%) with this soybean PAP, were found to exhibit phytase activity (Zhu et al., 2005; Zhang et al., 2008).

Besides involvement in P acquisition, plant PAPs may perform some other physiological roles. For example, the PAPs AtACP5 (AtPAP17), SAP1, and SAP2 (del Pozo et al., 1999; Bozzo et al., 2002) display not only phosphatase but also peroxidase activity, suggesting their involvement in the removal of reactive oxygen compounds in plant organs. A pollen-specific PAP from Ester lily was suggested to function as an iron carrier in mature pollen (Kim and Gynheung, 1996). Other studies indicate that plant PAPs may also be involved in NaCl stress adaption or cell regeneration (Kaida, 2003; Liao et al., 2003).

In the *Arabidopsis* genome, twenty-nine potential PAP genes were identified based on sequence comparison. Twenty-four of these putative enzymes contain seven conserved amino-acids residues involved in metal binding. One (AtPAP13) lacked four of these seven residues, and the other four (AtPAP14, 16, 28 and 29) lacked either the first, the second, or both motifs of the five conserved motifs. Twenty-eight are actively transcribed in *Arabidopsis* (Zhu et al., 2005).

To date, relatively little is known about AtPAPs biochemical properties and physiological roles, though several members have been characterized (del Pozo et al., 1999). AtPAP17 (AtACP5) was first known to be induced by phosphorus starvation. The transcription of AtPAP17 was also responsive to ABA, salt stress (NaCl), oxidative stress ($H_2O_2$) and leaves senescence, according to GUS activity assay. No alteration in the expression of AtPAP17 was observed during the nitrogen or potassium starvation, and paraquat or salicylic acid. Like the other type 5 acid phosphatases, AtPAP17 displayed peroxidation activity, which may be involved in the metabolism of reactive oxygen species in stressed or senescent parts of plants.

Besides AtPAP17, several AtPAPs were found to be involved in phosphorus metabolism in *Arabidopsis*. Root secretion of AtPAP12 was induced by P stress, and its regulation was mainly at transcriptional level (Patel et al., 1998; Coello, 2002/11). AtPAP4, as well as AtPAP10, AtPAP11 and AtPAP12 were involved in phosphorus starvation response since their transcription levels increased during phosphate deprivation (Li et al., 2002; Wu et al., 2003). In contrast, AtPAP20, 21 and 22 were irrespective to P starvation and expressed constitutively in Pi sufficient or deficient condition. Fluorescent signals were detected in the cytoplasm via the baculovirus expression system, indicating that they may function in the cytoplasm (Li and Wang, 2003).

AtPAP26 was purified and characterized from Pi-starved *Arabidopsis* suspension cell culture (Veljanovski et al., 2006). It exists as a homodimer with 55 kDa glycosylated protein, showing wide substrate specificity with the highest activity against phosphoenolpyruvate (PEP) and polypeptide phosphate. AtPAP26 also displayed alkaline peroxidase activity with the probable roles in the metabolism of reactive oxygen species. Proteomic study suggested that it may be localized in vacuole, and involved in recycling Pi from intracellular P metabolites (Shimaoka et al., 2004).

PAPs can act on a wide range of substrates, but not all of them exhibit phytase activity. An enzyme assay involving the GST-AtPAP23 fusion protein revealed that AtPAP23 exhibits phytase activity. A GUS study showed that AtPAP23 is exclusively expressed in the flower of the *Arabidopsis*, and may play certain roles in flower development (Zhu et al., 2005). In a recent report, a recombinant AtPAP15 expressed and partial purified in *E. coli* and yeast was also found to exhibit phytase activity) (Zhang et al., 2008). It was proposed that AtPAP15 may be involved in ascorbic acid biosynthesis with the end product myo-inositol of phytate hydrolysis as the precursor of ascorbic acid synthesis.

As stated above, most of the functions of characterized plant PAPs are related to phosphorus metabolism. None of the functionally or biochemically characterized plant PAPs carry transmembrane motif, and none of them were shown to be associated with membrane. Furthermore, to date, no AtPAPs or any plant PAPs, have been showed to affect sugar signalling and carbon metabolism in plant.

The first report of transgenic expression of plant PAP in plant was reported in 2005 (Xiao et al., 2005). The PAP-phosphatase gene from *Medicago* (MtPHY1) was expressed in transgenic *Arabidopsis*, resulting in increased capacity of P acquisition from phytate in agar culture (Xiao et al., 2005). Nonetheless, the growth performance of the plants was not reported to be different under normal growth.

3. SUMMARY

The present disclosure provides a method that speeds up plant growth and elevates plant yields by introducing phosphatases with a C-terminal motif into plants, Phosphatases with a C-terminal motif, and their respectively encoded protein products, as well as fragments, derivatives, homologues, and variants thereof are disclosed. Methods for introducing this class of genes into plants to speed up the growth rate of plants, to increase the sugar contents of plants, and to increase of yield of plants, are provided. Without wishing to be bound by any particular theory, the C-terminal motif is believed to function as a transmembrane structural element (transmembrane motif).

As stated above in the Background section, most of the functions of characterized plant PAPs are related to phosphorus metabolism. None of the functionally or biochemically characterized plant PAPs carry transmembrane motif, and none of them were shown to be associated with membrane. Furthermore, to date, no AtPAPs or any plant PAPs, have been showed to affect sugar signalling and carbon metabolism in plant.

The first report of transgenic expression of plant PAP in plant was reported in 2005 (Xiao et al., 2005). The PAP-phosphatase gene from *Medicago* (MtPHY1) was expressed in transgenic *Arabidopsis*, resulting in increased capacity of P acquisition from phytate in agar culture. Nonetheless, the growth performance of the plants was not reported to be different under normal growth.

We also produced transgenic tobacco and *Arabidopsis* that overexpressed AtPAP15, a PAP with phosphatase activity, which does not carry any C-terminal motif equivalent to that of AtPAP2; phosphatase activity was secreted into extracellular growth medium. Significant secretion of phosphatase activity was observed in the transgenic plants and the transgenic plants showed larger biomass than the control plants in agar and soil supplemented with exogenous phytate. Higher P content was also obtained in overexpressed transgenic lines in phytate treatment. However, the growth of transgenic plants overexpressing AtPAP15 did not show any difference in growth phenotypes when it was compared with the wild-type, under treatments of K—P or No—P, or in soil.

Here, we have developed a technology to speed up plant growth and improve seed yield by overexpressing a phosphatase with a C-terminal motif in plants. An example is the use of a purple acid phosphatase (PAP). This disclosure is the first report to show that overexpressing a phosphatase with a C-terminal motif in transgenic plant is able to speed up the growth of the plants, to increase the sugar contents of plants, and to increase the yield of plants, by altering the carbon metabolism of the plants.

The present advances are based, in part, on the characterization of a group of purple acid phosphatases (SEQ ID NOS: 1-8 and 18-47) from plants and the observations that overexpression of a purple acid phosphatase (AtPAP2, SEQ ID NO:1) of this group in plants resulted in rapid plant growth, higher sugar content, and higher yield. Accordingly, nucleotide sequences of a group of purple acid phosphatase genes (SEQ ID NOs:1, 3, 5, 7, 18, 20, 22, 24, 26, 28, 30, 32, 34, 36, 38, 40, 42, 44 and 46), which share a C-terminal motif/domain, from plants and amino acid sequences of their encoded proteins (SEQ ID NOS:2, 4, 6, 8, 19, 21, 23, 25, 27, 29, 31, 33, 35, 37, 39, 41, 43, 45 and 47), as well as fragments, derivatives, homologues, and variants thereof, as defined herein, are disclosed. Furthermore, nucleic acid molecules encoding the polypeptides of interest, and include cDNA, genomic DNA, and RNA, are disclosed.

As used herein, italicizing the name of a gene shall indicate the gene, in contrast to its encoded protein or polypeptide product which is indicated by the name of the gene in the absence of any italicizing. For example, "Gene" shall mean the Gene gene, whereas "Gene" shall indicate the protein or polypeptide product of the Gene gene.

In one embodiment, isolated nucleic acid molecules hybridize under stringent conditions, as defined herein, to nucleic acids having the sequence of SEQ ID NOS: 1, 3, 5, 7, 18, 20, 22, 24, 26, 28, 30, 32, 34, 36, 38, 40, 42, 44 or 46, or homologues thereof, wherein the nucleic acid molecules encode proteins or polypeptides which exhibit at least one structural and/or functional feature of the polypeptides of the invention.

Another embodiment includes, nucleic acid molecules, which are suitable for use as primers or hybridization probes for the detection of nucleic acids encoding one of the disclosed phosphatase polypeptides or other sequences.

Yet another embodiment includes vectors, e.g., recombinant expression vectors, comprising a nucleic acid molecule of the invention. Furthermore, host cells containing such a vector or engineered to contain and/or express a nucleic acid molecule of the invention and host cells containing a nucleotide sequence of the invention operably linked to a heterologous promoter are disclosed.

A further embodiment includes methods for preparing a polypeptide of the invention by a recombinant DNA technology in which the host cells containing a recombinant expression vector encoding a polypeptide of the invention or a nucleotide sequence encoding a polypeptide of the invention operably linked to a heterologous promoter, are cultured, and the polypeptide of the invention are produced.

In still further another embodiment, a transgenic plant contains a nucleic acid molecule which encodes an isolated polypeptides or proteins comprising the five conserved motifs of purple acid phosphatases, including XDXX, XDXXY, GNH(D/E), XXXH, XHXH, and linked to a C-terminal motif.

Embodiments further provide antibodies that immunospecifically bind a polypeptide of the invention. Such antibodies include, but are not limited to, antibodies from various animals, humanized, chimeric, polyclonal, monoclonal, bi-specific, multi-specific, single chain antibodies, Fab fragments, $F(ab')_2$ fragments, disulfide-linked Fvs, fragments containing either a VL or VH domain or even a complementary determining region (CDR), that immunospecifically binds to a polypeptide of the invention.

In an additional embodiment, method for detecting the presence, activity or expression of a polypeptide of the invention or similar polypeptide in a biological material, such as cells, culture media, and so forth are provided. The increased or decreased activity or expression of the polypeptide in a sample relative to a control sample can be determined by contacting the biological material with an agent that can detect directly or indirectly the presence, activity or expression of the polypeptide of the invention. In a particular embodiment, such an agent is an antibody or a fragment thereof which immunospecifically binds to a one of the disclosed polypeptides.

In a still another embodiment, a fusion protein comprising a bioactive molecule and one or more domains of a disclosed polypeptide or fragment thereof is provided. In particular, fusion proteins comprising a bioactive molecule recombinantly fused or chemically conjugated (including both covalent and non-covalent conjugations) to one or more domains of a disclosed polypeptide or fragments thereof.

We also produced transgenic tobacco and *Arabidopsis* that overexpressed AtPAP15, a PAP with phosphatase activity, which does not carry any C-terminal motif and was found to be secreted into extracellular growth medium. Significant secretion of phosphatase activity was observed in the transgenic plants and the transgenic plants showed larger biomass than the control plants in agar and soil supplemented with exogenous phytate. Higher P content was also obtained in overexpressed transgenic lines in phytate treatment. However, the growth of transgenic plants overexpressing AtPAP15 did not show any difference in growth phenotypes when it was compared with the wild-type, under treatments of K—P or No P, or in soil.

In conclusion, this disclosure is the first report to show that overexpressing a phosphatase with a C-terminal motif in transgenic plant is able to speed up the growth of the plants, to increase the sugar contents of plants, and to increase the yield of plants, by altering the carbon metabolism of the plants.

3.1 DEFINITIONS

The term “acidic” or “acid pH” as used herein refers to a pH value of less than about 6.0.

The term “homologue” as used herein refers to a polypeptide that possesses a similar or identical function to polypeptides encoded by SEQ ID NOS: 2, 4, 6, 8, 19, 21, 23, 25, 27, 29, 31, 33, 35, 37, 39, 41, 43, 45 and 47, and/or a fragment of these polypeptides, that do not have an identical amino acid sequence of these polypeptides and/or a fragment of these polypeptides. A polypeptide that has a similar amino acid sequence included in the definition of the term “homologue” includes a polypeptide that satisfied at least one of the following: (i) polypeptide having an amino acid sequence that is one or more of at least about 30%, at least about 40%, at least about 50%, at least about 60%, at least about 70%, at least about 80%, at least about 90%, and at least about 98% identical. (ii) a polypeptide encoded by a nucleotide sequence that is one or more of at least about 30%, at least about 40%, at least about 50%, at least about 60%, at least about 70%, at least about 80%, at least about 90%, and at least about 98% identical and/or conservatively substituted to one or more of the nucleotide sequences encoding the polypeptides of SEQ ID NOS: 2, 4, 6, 8, 19, 21, 23, 25, 27, 29, 31, 33, 35, 37, 39, 41, 43, 45 and 47, and/or a fragment of the these polypeptides; (iii) a polypeptide encoded by a nucleotide sequence that hybridizes under stringent conditions as defined herein to one or more of nucleotide sequences SEQ ID NOS: 1, 3, 5, 7, 18, 20, 22, 24, 26, 28, 30, 32, 34, 36, 38, 40, 42, 44 and 6; (iv) a polypeptide having an amino acid sequence that is one or more of at least about 30%, at least about 40%, at least about 50%, at least about 60%, at least about 70%, at least about 80%, at least about 90, and at least about 98% identical and/or conservatively substituted; (v) a nucleic acid sequence encoding an amino acid sequence that is one or more of at least about 30%, at least about 40%, at least about 50%, at least about 60%, at least about 70%, at least about 80%, at least about 90%, and at least about 98% identical and/or conservatively substituted; (vi) a fragment of any of the polypeptides or nucleic acid sequences described in (i) through (v) having one of at least 20 amino acid residues, at least 25 amino acid residues, at least 40 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, at least 225 amino acid residues, at least 250 amino acid residues, at least 275 amino acid residues, at least 300 amino acid residues, at least 325 amino acid residues, at least 350 amino acid residues, or at least 375 amino acid residues; (vii) a polypeptide with similar structure and function or a nucleotide sequence encoding a polypeptide with similar structure and function, exhibiting the antigenicity, immunogenicity, catalytic activity, and other readily assayable activities, to polypeptides encoded by SEQ ID NOS: 2, 4, 6, 8, 19, 21, 23, 25, 27, 29, 31, 33, 35, 37, 39, 41, 43, 45 and 47, and/or a fragment of these polypeptides, refers to a polypeptide that has a similar secondary, tertiary, or quaternary structure of these polypeptides, or a fragment of these polypeptides. The structure of a polypeptide can be determined by methods known to those skilled in the art, including but not limited to, X-ray crystallography, nuclear magnetic resonance, and crystallographic electron microscopy. The term “homologue” is used herein to describe a sequence that has sequence homology. A sequence having sequence homology can be made using standard molecular biology techniques including site-directed mutagenesis including insertion or deletion of sequences. The term “homologue” is not limited to homologous genes or proteins originating from different species and expressly includes artificial modification to the sequences disclosed herein.

The term “conservatively substituted variant” refers to a polypeptide or a nucleic acid sequence encoding a homologue polypeptide in which one or more amino acid residues or codons have been modified by conservative substitution with an amino acid residue or a codon coding for an amino acid residue of similar chemical-type, as described below.

The term “an antibody or an antibody fragment which immunospecifically binds to polypeptides encoded by SEQ ID NOS: 2, 4, 6, 8, 19, 21, 23, 25, 27, 29, 31, 33, 35, 37, 39, 41, 43, 45 and 47," as used herein refers to an antibody or a fragment thereof that immunospecifically binds to polypeptides encoded by SEQ ID NOS: 2, 4, 6, 8, 19, 21, 23, 25, 27, 29, 31, 33, 35, 37, 39, 41, 43, 45 and 47, or a fragment of these polypeptide and does not non-specifically bind to other polypeptides. An antibody or a fragment thereof that immunospecifically binds to polypeptides encoded by SEQ ID NOS: 2, 4, 6, 8, 19, 21, 23, 25, 27, 29, 31, 33, 35, 37, 39, 41, 43, 45 and 47, or a fragment of these polypeptide, may cross-react with other antigens. Preferably, an antibody or a fragment thereof that immunospecifically binds to polypeptides encoded by SEQ ID NOS: 2, 4, 6, 8, 19, 21, 23, 25, 27, 29, 31, 33, 35, 37, 39, 41, 43, 45 and 47, or a fragment of these polypeptides, does not cross-react with other antigens. An antibody or a fragment thereof that immunospecifically binds to polypeptides encoded by SEQ ID NOS: 2, 4, 6, 8, 19, 21, 23, 25, 27, 29, 31, 33, 35, 37, 39, 41, 43, 45 and 47, or a fragment of these polypeptide, can be identified by, for example, immunoassays or other techniques known to those skilled in the art. An antibody or an antibody fragment which immunospecifically binds polypeptides encoded by SEQ ID NOS: 2, 4, 6, 8, 19, 21, 23, 25, 27, 29, 31, 33, 35, 37, 39, 41, 43, 45 and 47, may be interchangeably referred to as "anti-PAP antibody".

The term "derivative" as used herein refers to a given peptide or protein that is otherwise modified, e.g., by covalent attachment of any type of molecule, preferably having bioactivity, to the peptide or protein, including the incorporation of non-naturally occurring amino acids. The resulting bioactivity retains one or more biological activities of the peptide protein.

The term "fragment" as used herein refers to a fragment of a nucleic acid molecule containing one of at least about 25, at least about 30, at least about 35, at least about 40, at least about 45, at least about 100, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950, at least about 1000, at least about 1050, at least about 1100, at least about 1150, at least about 1200, at least about 1250, at least about 1300, at least about 1350, from about 500 to about 2000, from about 1000 to about 2000 from about 200 to about 500, from about 500 to about 1000, form about 1000 to about 1500, and from about 1500 to about 2000 nucleic acid bases in length of the relevant nucleic acid molecule and having at least one functional feature of the nucleic acid molecule (or the encoded protein has one functional feature of the protein encoded by the nucleic acid molecule); or a fragment of a protein or a polypeptide containing one or more of at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 90, at least about 100, at least about 120, at least about 140, at least about 160, at least about 180, at least about 200, at least about 220, at least about 240, at least about 260, at least about 280, at least about 300, at least about 320, at least about 340, at least about 360, from about 250 to about 660, from about 350 to about 660, form about 450 to about 660, and form about 550 to about 660 amino acid residues in length of the relevant protein or polypeptide and having at least one functional feature of the protein or polypeptide, such functional features include ability to bind a $Fe^{3+}$-$Me^{2+}$ dimetal nuclear center and form a C-terminal motif.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular materials, or culture medium when produced by recombinant techniques, or substantially free of chemical precursors or other chemicals when chemically synthesized, but excludes nucleic acid molecules present in recombinant DNA libraries. In a preferred embodiment, nucleic acid molecules encoding the disclosed polypeptides/proteins are isolated or purified.

The term "operably linked" as used herein refers to when transcription under the control of the "operably linked" promoter produces a functional messenger RNA, translation of which results in the production of the polypeptide encoded by the DNA operably linked to the promoter.

The term "under stringent condition" refers to hybridization and washing conditions under which nucleotide sequences having homology to each other remain hybridized to each other. Such hybridization conditions are described in, for example but not limited to, *Current Protocols in Molecular Biology*, John Wiley & Sons, N.Y. (1989), 6.3.1-6.3.6; *Basic Methods in Molecular Biology*, Elsevier Science Publishing Co., Inc., N.Y. (1986), pp. 75-78, and 84-87; and Molecular Cloning, Cold Spring Harbor Laboratory, N.Y. (1982), pp. 387-389, and are well known to those skilled in the art. A preferred, non-limiting example of stringent hybridization conditions is hybridization in 6× sodium chloride/sodium citrate (SSC), 0.5% SDS at about 68° C. followed by one or more washes in 2×SSC, 0.5% SDS at room temperature. Another preferred, non-limiting example of stringent hybridization conditions is hybridization in 6×SSC at about 45° C. followed by one or more washes in 0.2×SSC, 0.1% SDS at about 50-65° C.

The term "variant" as used herein refers either to a naturally occurring allelic variation of a given peptide or a recombinantly prepared variation of a given peptide or protein in which one or more amino acid residues have been modified by amino acid substitution, addition, or deletion.

The term "aligned" as used herein refers to a homology alignment between two or more sequences using a standard algorithm such as BLAST (http://blast.ncbi.nlm.nih.gov/Blast.cgi).

The term "predicted to form a transmembrane motif by TMHMM analysis" or "predicted to form a C-terminal motif by TMHMM analysis" (http://www.cbs.dtu.dk/services/TMHMM/) herein refers to a probability that is equal to or greater than about 0.5.

BRIEF DESCRIPTION OF THE FIGURES

The following figures illustrate the embodiments and are not meant to limit the scope of the invention encompassed by the claims.

FIG. 2A is the amino acid alignment of the C-terminal transmembrane-like motifs in AtPAP2 (SEQ ID NO. 2) with other PAP sequences.

FIG. 2B is the amino acid alignment of AtPAP2 (SEQ ID NO. 2) with other PAP sequences, showing the full length of each sequence. These sequences include homologous sequences from *B. napus* (BnPAP2) SEQ ID NO. 47, *G. max* (GmPAP2, SEQ ID NO. 6) and *Z. may* (ZmPAP2, SEQ ID NO. 8). The five conserved motifs (XDXX, XDXXY, GNH (D/E), XXXH, XHXH) are boxed. Residues in shades have low or no homology. Hydrophobic motifs at the C-termini of these polypeptides are underlined by a bar ($614^{th}$-$636^{th}$ amino acid), which is absent from the sequence of AtPAP15. As shown, AtPAP15 (SEQ ID NO:67) does not have a C-terminal region corresponding to the other PAP sequences.

FIG. 4 shows the characteristics of the T-DNA lines. The T-DNA line (Salk_013567) was obtained from TAIR. The AtPAP2 genomic sequence carries two exons and the T-DNA was inserted in exon 2 and causes a disruption of the AtPAP2 mRNA (a). Three PCR primers (A, B and C) were designed for the differentiation of the wild-type (WT) and the T-DNA line (atpap2-8) and they were used for PCR screening of genomic DNA extracted from WT and the T-DNA line (b). Total RNA was extracted from 10-day-old seedlings grown on MS with 2% sucrose using the TRIzol RNA isolation method and were used for RT-PCR (c). 50 μg of seedlings proteins were loaded for Western blotting studies, using the anti-AtPAP2 specific antiserum (Section 6.3).

FIG. 6A shows the results of the Western blot analysis of the overexpression lines (OE), wild-type (WT), T-DNA and the complementation lines (CP) of AtPAP2 and FIG. 6B shows the results of the Western blot analysis of the overexpression lines (C-15) and wild-type (WT) of AtPAP15.

FIG. 7 shows the expression analysis of AtPAP2. The mRNA expression profile was analysed by the Spot History program of NASC (a). The protein expression profiles of 30 day old, soil-grown plant (b), seedlings germinated on MS agar (c) and 2 week old plants transferred to Pi-sufficient/Pi-deficient MS agar for 3 days (d), were analyzed by Western blotting using the anti-PAP2 antiserum.

DETAILED DESCRIPTION

5.1 Method of Speeding Up Plant Growth and Improving Crop Yield

The present disclosure provides a method that speeds up plant growth and elevates plant yields by introducing phosphatases with a C-terminal motif into plants. In an embodiment, the present disclosure relates to a class of genes of purple acid phosphates, and their respectively encoded protein products, as well as fragments, derivatives, homologues, and variants thereof. Methods for introducing this class of genes into plants to speed up the growth rate of plants, to increase the sugar contents of plants, and to increase of yield of plants, are provided.

Figure 1:
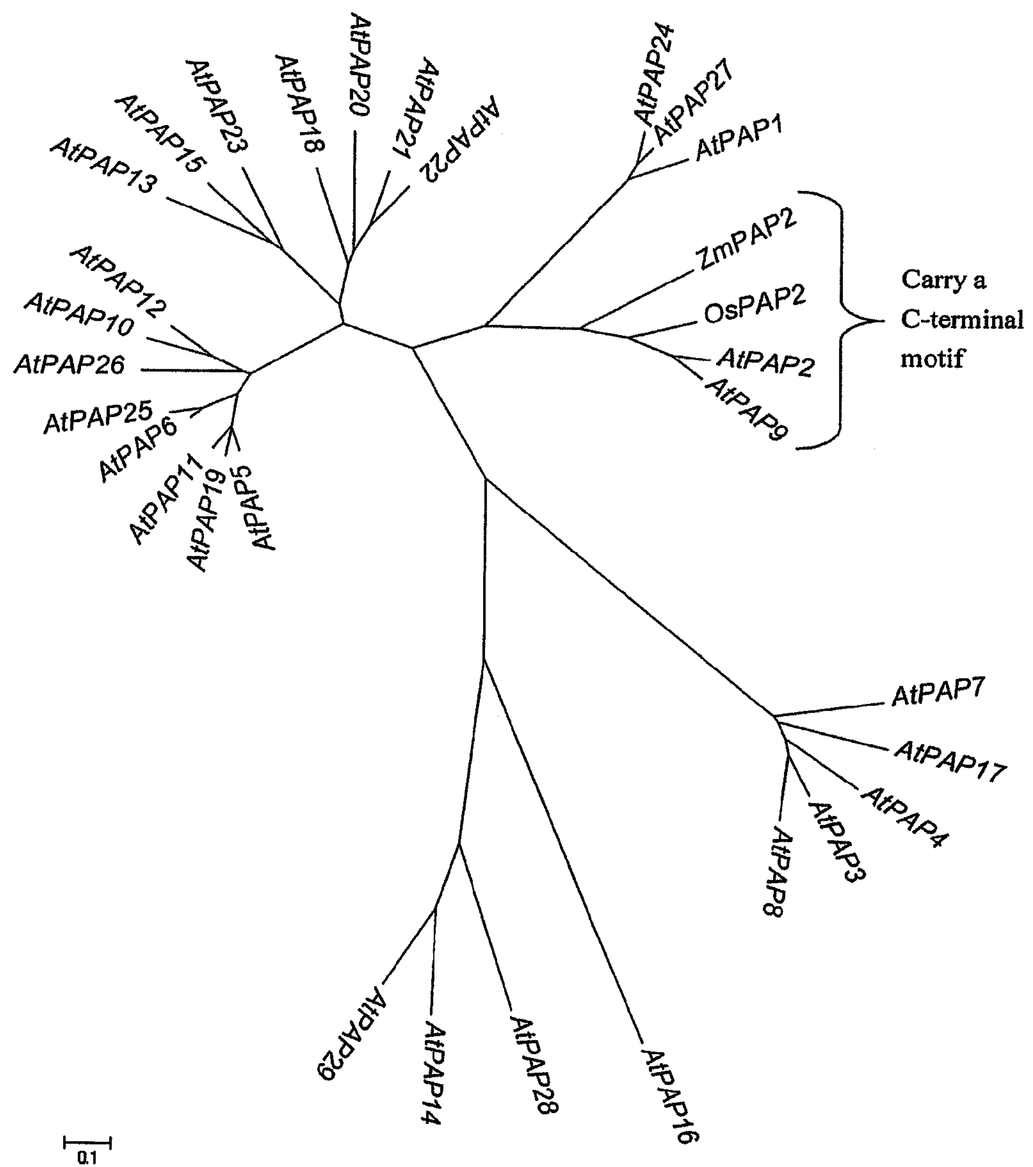
FIG. 1 shows the phylogenetic tree of PAP-like sequences in the *Arabidopsis* genome. Twenty-nine PAPs were aligned using ClustalX and the phylogenetic tree was created by the neighbor-joining algorithm of the MEGA4 program. The accession numbers of the PAP-like, transmembrane-like C-terminal motif containing, polypeptide from *Zea mays* (ZmPAP2) and *Oryza sativa* (OsPAP2) were ACG47621 and BAC15853.1, respectively.
Figure 3:
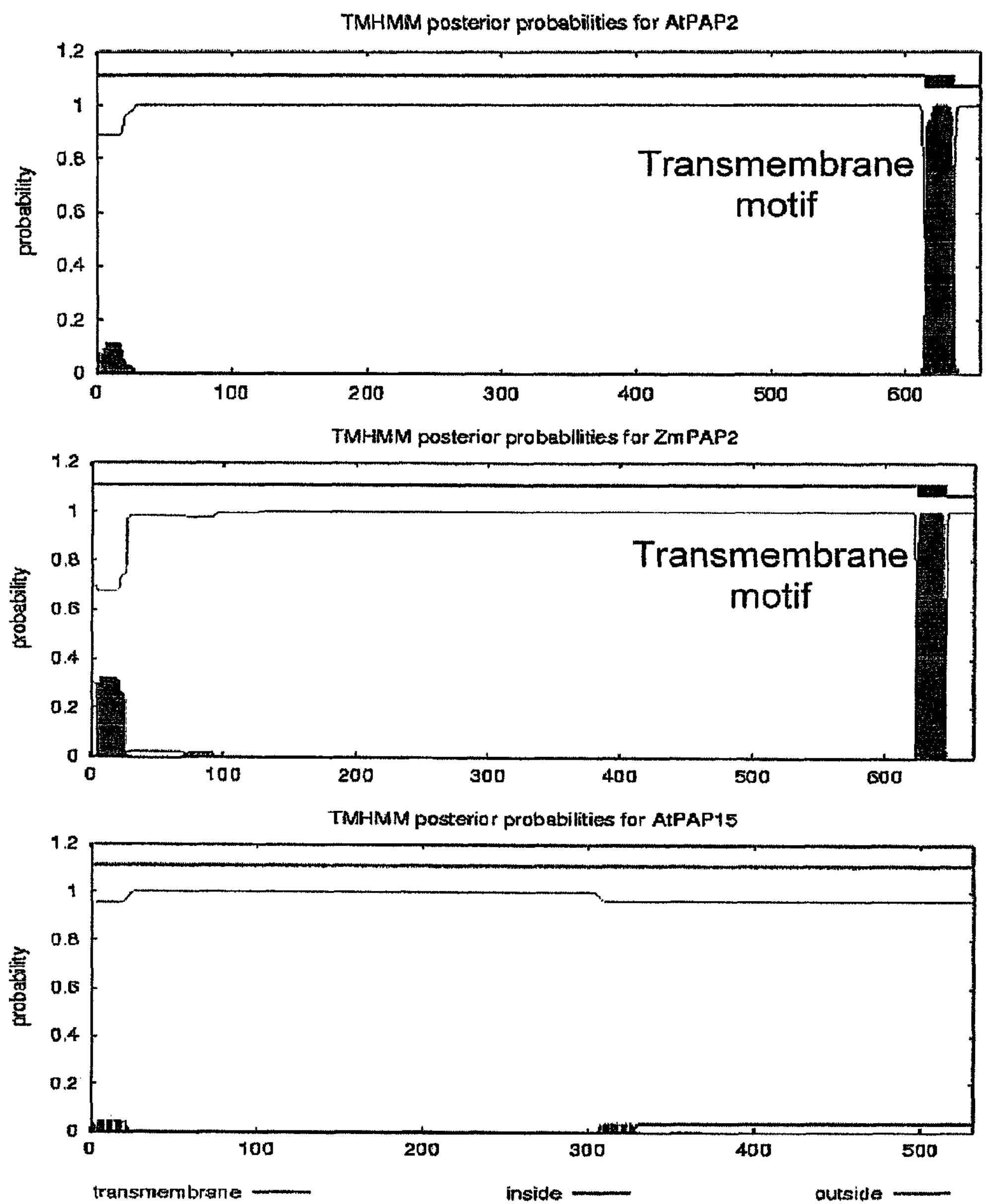
FIG. 3 shows that a unique hydrophobic motif is present at the C-termini of AtPAP2 and ZmPAP2 by TMHMM analysis. This transmembrane-like C-terminal motif is absent from AtPAP15.
Figure 11:
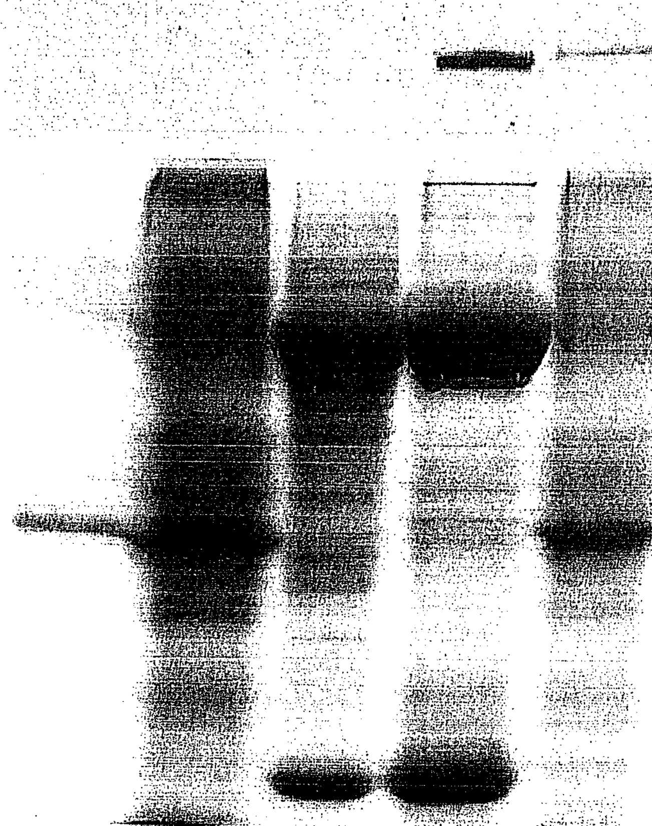
FIG. 11. Detection of AtPAP2 protein in subcellular fractions by Western blotting. Mito.: Mitochondria; Chlorop.: Chloroplasts.

A group of purple acid phosphatases (PAPs) which carry seven conserved amino acid residues (shown in bold face) in the five conserved motifs XDXX (example GDXG (SEQ ID NO: 48)), XDXXY (SEQ ID NO: 49), GNH(D/E) (SEQ ID NOS: 50-51), XXXH (example ZXGH (SEQ ID NO: 52)), XHXH (SEQ ID NO: 53), where X is any amino acid and Z is any amino acid selected from L, I, V, F, and M, and a transmembrane-like motif at their C-termini were identified in the genomes of a number of plants (FIGS. 1, 2A, and 2B). The presence of the C-terminal transmembrane-like motif enables the localization of this group of PAN to the membrane fraction (FIGS. 3 and 11). This property makes this group of PAPs differ from the other previously characterized PAPs because all previously characterized PAPs did not carry any C-terminal motif (FIGS. 2A, 2B, and 3). By using the protein sequence of a representative gene of this group, AtPAP2, to blast the NCBI database and various EST databases, a number of genomic or cDNA sequences were identified to encodes polypeptides that carry the five conserved motifs XDXX, XDXXY, GNH(D/E), XXXH, XHXH of PAPs and a transmembrane motif at their C-termini (FIG. 2B).

Figure 8:
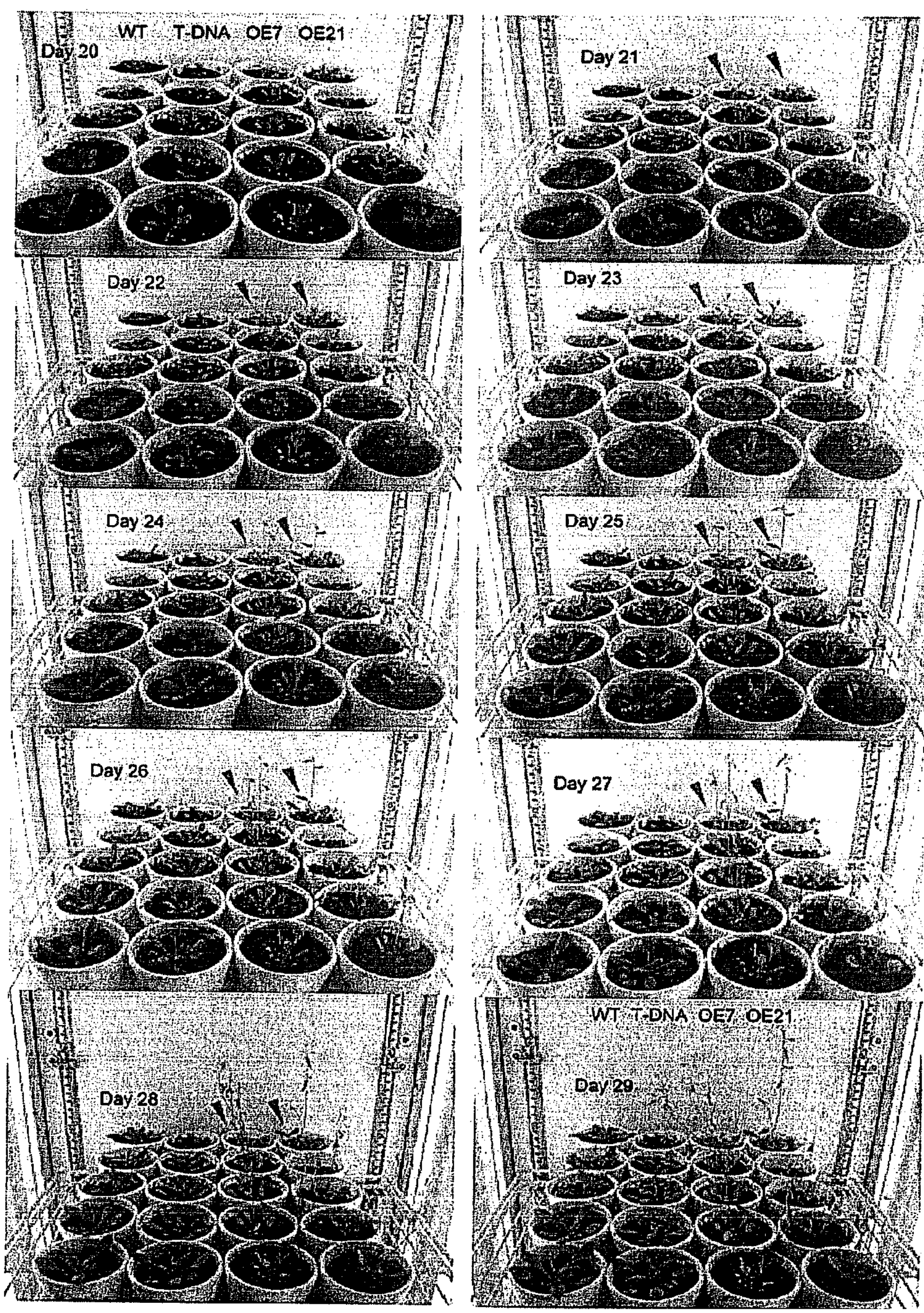
FIG. 8 shows the growth performance of the wild-type, T-DNA and overexpression lines in soil. Seeds were germinated in MS agar with 2% sucrose for 10 days. Seedlings with 2 small visible rosette leaves (~1 mm) were transferred to soil and grown under 16 h/8 h light/dark cycles.
Figure 9:
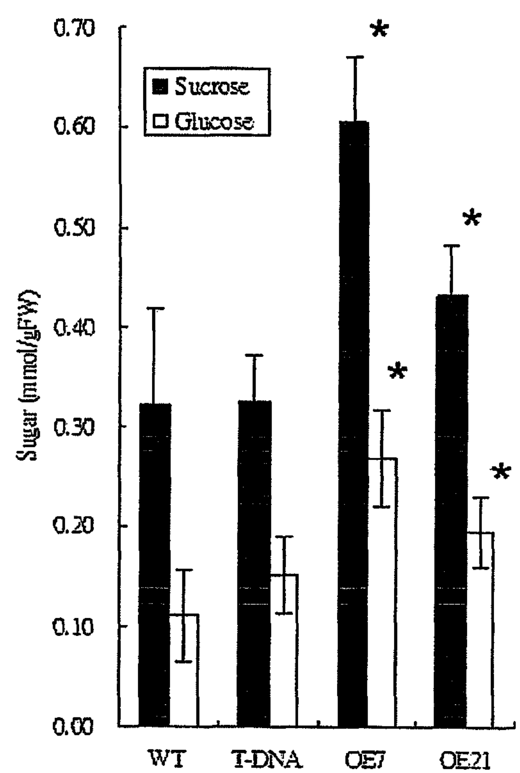
FIG. 9 shows the levels of sucrose and glucose in the rosette leaves of 21-day-old, soil grown seedlings.

The introduction of a representative gene of this group of phosphatases, AtPAP2, into the genome of *Arabidopsis* by transgenic technology produced transgenic *Arabidopsis* that grew faster than the wild-type plants (FIG. 8), and the yield of seeds were elevated by approximately 40% (Table 3). However, transgenic plant that expressed AtPAP15 did not show these phenotypes. The sugar contents, including glucose and sucrose, in the leaf of the transgenic lines, were also found to be higher than that of the wild-types (FIG. 9).

Thus, this disclosure provides a method that speeds up plant growth and elevates plant yields by introducing phosphatases into plants. In an embodiment, a group of genes of purple acid phosphatases, and their respectively encoded protein products, as well as fragments, derivatives, homologues, and variants thereof are described.

5.2 Homologues, Derivatives, and Variants of Phosphatases

In addition to the nucleic acid molecules (SEQ ID NOS: 1, 3, 5, 7, 18, 20, 22, 24, 26, 28, 30, 32, 34, 36, 38, 40, 42, 44 and 46) and polypeptides (SEQ ID NOS: 2, 4, 8, 19, 21, 23, 25, 27, 29, 31, 33, 35, 37, 39, 41, 43, 45 and 47) described in claims 9-16, the nucleic acid molecules and polypeptides also encompass those nucleic acid molecules and polypeptides having a common biological activity, similar or identical structural domain and/or having sufficient nucleotide sequence or amino acid identity (homologues) to those of the nucleic acid molecules and polypeptides described above.

Such common biological activities of the polypeptides include antigenicity, immunogenicity, catalytic activity especially phosphatase activity, ability to bind a $Fe^{3+}$-$Me^{2+}$ dimetal nuclear center, fold into or form a transmembrane-like C-terminal motif and other activities readily assayable by the skilled artisan.

A polypeptide that has a similar amino acid sequence (homologue) refers to a polypeptide that satisfied at least one of the following: (i) a polypeptide having an amino acid sequence that is one of at least about 30%, at least about 40%, at least about 50%, at least about 60%, at least about 70%, at least about 80%, at least about 90%, and at least about 95%, and at least about 98% identical and/or conservatively substituted to the amino acid sequence of a AtPAP2 (SEQ ID NO: 2) and/or other PAPs with a transmembrane-like C-terminal motif including SEQ ID NOS: 4, 6, 8, 19, 21, 23, 25, 27, 29, 31, 33, 35, 37, 39, 41, 43, 45 and/or 47, a fragment of AtPAP2, and having at least one biological feature of the described polypeptides; (ii) a polypeptide encoded by a nucleotide sequence that is one of at least about 30%, at least about 40%, at least about 40%, at least about 50%, at least about 60%, at least about 70%, at least about 80%, at least about 90%, at least about 95%, and at least about 98% identical to the nucleotide sequence encoding AtPAP2 (SEQ ID NO: 1) and/or other PAPs with a transmembrane-like C-terminal motif including SEQ ID NOS: 3, 5, 7, 18, 20, 22, 24, 26, 28, 30, 32, 34, 36, 38, 40, 42, 44 and/or 46, a fragment of AtPAP2 and having at least one structural and/or biological feature of AtPAP2; (iii) a polypeptide encoded by a nucleotide sequence that hybridizes under stringent conditions as defined herein to a nucleotide sequence encoding AtPAP2 (SEQ ID NO: 1) and/or other PAPs with a motif including SEQ ID NOS: 3, 5, 7, 18, 20, 22, 24, 26, 28, 30, 32, 34, 36, 38, 40, 42, 44 and/or 46, a fragment of AtPAP2 and having at least one structural and/or biological feature of AtPAP2. A polypeptide with similar structure to AtPAP2, or a fragment of AtPAP2, refers to a polypeptide that has a similar secondary, tertiary, or quaternary structure of AtPAP2, a fragment of AtPAP2 and has at least one functional feature of a AtPAP2, including one or more of ability to bind a $Fe^{3+}$-$Me^{2+}$ dimetal nuclear center and fold into or form a transmembrane-like C-terminal motif. The structure of a polypeptide can be determined by methods known to those skilled in the art, including but not limited to, X-ray crystallography, nuclear magnetic resonance, and crystallographic electron microscopy.

Those having skill in the art will readily recognized that mutations, deletions or insertions can be made in any of the sequences disclosed herein, including SEQ ID NOS: 1-8 and 18-47, without affecting function. Sequences useful in practicing the embodiments include sequences having homology to SEQ ID NOS: 1-8 and 18-47 and being a protein, polypeptide, or polynucleotide coding for such protein or peptide having functionality to bind a dimetal nuclear center ($Fe^{3+}$-$Me^{2+}$) and being a protein, polypeptide, or polynucleotide coding for such protein or peptide having a C-terminal motif. That is, those skilled in the art will recognize that many mutations can be made to any of SEQ ID NOS: 1-8 and 18-47 without affecting the catalytic functionality nor interrupting the transmembrane-like C-terminal motif. Such modified sequences that maintain catalytic activity and a transmembrane-like C-terminal motif are defined as homologues to SEQ ID NOS: 1-8 and 18-47 and are including within the scope of useful sequences.

In one embodiment, such homologues can have about 30% or more identity to the sequences disclosed herein. In another embodiment, such homologues can have about 40% or more identity to the sequences disclosed herein. In yet another embodiment, such homologues can have about 50% or more identity to the sequences disclosed herein. In sill yet another embodiment, such homologues can have about 60% or more identity to the sequences disclosed herein. In even sill yet another embodiment, such homologues can have about 70% or more identity to the sequences disclosed herein. In a further embodiment, such homologues can have about 80% or more identity to the sequences disclosed herein. In yet a still further embodiment, homologues can have about 90% or more identity to the sequences disclosed herein. In a still further embodiment, homologues can have about 98% or more identity to the sequences disclosed herein.

Those having skill in the art will recognize that mutations can be made to proteins and peptides and/or to polynucleotides coding for protein and peptides or complementary thereto that substitute amino acid residue for other amino acids residues having similar chemical properties (conservative substitutions) and that such mutations are less likely to cause structural changes that affect functionality including catalytic activity and/or the function of a transmembrane-like C-terminal motif. Conservatively substituting amino acids are substituting an amino acid residue belong to any of the following 11 chemical groups with another amino acid from the same chemical group: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; (4) neutral nonpolar (hydrophobic) amino acids such as alanine, leucine, isoleucine, valine, proline, phenylalanine, tryptophan, and methionine; (5) amino acids having aliphatic side chains such as glycine, alanine, valine, leucine, and isoleucine; (6) amino acids having aliphatic-hydroxyl side chains such as serine and threonine; (7) amino acids having amide-containing side chains such as asparagine and glutamine; (8) amino acids having aromatic side chains such as phenylalanine, tyrosine, and tryptophan; (9) amino acids having basic side chains such as lysine, arginine, and histidine; (10) amino acids having sulfur-containing side chains such as cysteine and methionine; (11); amino acids having similar geometry and hydrogen bonding patterns such as aspartic acid, asparagine, glutamic acid and glutamine.

In one embodiment, homologues can have about 30% or more identity and/or conservative substitutions to the sequences disclosed herein. In another embodiment, homologues can have about 40% or more identity and/or conservative substitutions to the sequences disclosed herein. In yet another embodiment, homologues can have about 50% or more identity and/or conservative substitutions to the sequences disclosed herein. In still yet another embodiment, homologues can have about 60% or more identity and/or conservative substitutions to the sequences disclosed herein. In a further embodiment, homologues can have about 70% or more identity and/or conservative substitutions to the sequences disclosed herein. In a still further embodiment, homologues can have about 80% or more identity and/or conservative substitutions to the sequences disclosed herein. In still another embodiment, homologues can have about 90% or more identity and/or conservative substitutions to the sequences disclosed herein. In still another further embodiment, homologues can have about 98% or more identity and/or conservative substitutions to the sequences disclosed herein.

Embodiments further provide isolated nucleic acid molecules which comprise or consist of one or more of at least about 25, at least about 30, at least about 35, at least about 40, at least about 45, at least about 100, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950, at least about 1000, at least about 1050, at least about 1100, at least about 1150, at least about 1200, at least about 1250, at least about 1300, at least about 1350, from about 500 to about 2000, from about 1000 to about 2000, from about 200 to about 500, from about 500 to about 1000, form about 1000 to about 1500, and from about 1500 to about 2000 nucleotides of the nucleotide sequences of SEQ ID NOS: 1, 3, 5, 7, 18, 20, 22, 24, 26, 28, 30, 32, 34, 36, 38, 40, 42, 44 and 46, or a complement thereof encoding a protein or polypeptide having one or more activity of the amino acid sequences of their encoded proteins (SEQ ID NOS: 2, 4, 6, 8, 19, 21, 23, 25, 27, 29, 31, 33, 35, 37, 39, 41, 43, 45 and 47). The activity includes one or more of antigenicity, immunogenicity, catalytic activity (e.g., phosphatase activity), ability to bind a $Fe^{3+}$-$Me^{2+}$ dimetal nuclear center, fold into or form a transmembrane-like C-terminal motif, and other activities readily assayable.

Embodiments provide isolated polypeptides or proteins consisting of an amino acid sequence that contains one of about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 90, at least about 100, at least about 120, at least about 140, at least about 160, at least about 180, at least about 200, at least about 220, at least about 240, at least about 260, at least about 280, at least about 300, at least about 320, at least about 340, at least about 360, from about 250 to about 660, from about 350 to about 660, form about 450 to about 660, and form about 550 to about 660 amino acid bases in length of the relevant protein or polypeptide and having at least one functional feature of the protein or polypeptide, such functional features including ability to bind a $Fe^{3+}$-$Me^{2+}$ dimetal nuclear center and form a transmembrane-like C-terminal motif.

Additional embodiments are any of the phosphatases and homologues thereof with the identity and/or conservative substitutions to SEQ ID NOS: 1-8 and 18-47 described above that additionally consist of a protein, polypeptide, or polynucleotide encoding a protein having the five conserved motifs in purple acid phosphatases, including XDXX, XDXXY, GNH(D/E), XXXH, XHXH, where X is any amino acid. In one embodiment, the described phosphatases and homologues thereof consist of a protein, polypeptide, or polynucleotide encoding one of the sequences YHVCIGNHEYDF (SEQ ID NO: 54) and YHVCIGNHEYDW (SEQ ID NO: 55). In one embodiment, the described phosphatases and homologues thereof consist of a protein, polypeptide, or polynucleotide encoding a sequence of amino acid residues having one of the sequences YHVCIGNHEYD(W/F) (SEQ ID NO: 54) and YHVCIGNHEYN(W/F) (SEQ ID NO: 55) or a protein, polypeptide, or polynucleotide encoding a homologue to one of the foregoing sequences with only conservative substitutions, as described above, to those sequences. In yet another embodiment, the described phosphatases and homologues thereof consist of a protein, polypeptide, or polynucleotide encoding a sequence of amino acid residues having one of the sequences GNHE (SEQ ID NO: 51) and GNHD (SEQ ID NO: 50). In still yet another embodiment, the described phosphatases and homologues thereof consist of a protein, polypeptide, or polynucleotide encoding a sequence of amino acid residues having one of the sequences GNHE (SEQ ID NO: 51) and GNHD (SEQ ID NO: 50) or a protein, polypeptide, or polynucleotide encoding a protein having a homologous sequence to one of the foregoing sequences SEQ 1N NOS: 50-51 with only conservative substitutions.

Additional embodiments are any of the phosphatases and homologues thereof with the identity and/or conservative substitutions to SEQ ID NOS: 1-8 and 18-47 described above that additionally consist of a protein, polypeptide, or polynucleotide encoding a sequence having at least about 70% or more identity and/or conservative substitutions to amino acid residues 302-315 of SEQ ID NO: 2 when such sequence is aligned with SEQ ID NO: 2. In another embodiment, the described phosphatases and homologues thereof consist of a protein, polypeptide, or polynucleotide encoding a protein having about 80% or more identity and/or conservative substitutions to amino acid residues 302-315 of SEQ ID NO: 2 when such sequence is aligned with SEQ ID NO: 2. In another embodiment, the described phosphatases and homologues consist of a protein, polypeptide, or polynucleotide encoding a sequence of amino acid residues having at least about 70% or more identity to the sequence HIGDISYARGYSW (SEQ ID NO: 56). In another embodiment, the described phosphatases and homologues thereof consist of a protein, polypeptide, or polynucleotide encoding a sequence of amino acid residues having the sequence HIGDISYARGYSW (SEQ ID NO: 56) or a protein, polypeptide, or polynucleotide encoding a protein having a homologous sequence to the foregoing sequences with only conservative substitutions, as described above, to those sequences.

In another embodiment, the described phosphatases and homologues thereof consist of a protein, polypeptide, or polynucleotide encoding a sequence of amino acid residues having at least about 70% or more identity to the sequences KEKLTVSFVGNHDGEVHD (SEQ ID NO: 57), KERLTLSYVGNHDGEVHD (SEQ ID NO: 58), REKLTLTYVGNHDGQVHD (SEQ ID NO: 59), and KEKLTLTYIGNHDGQVHD (SEQ ID NO: 60). In still yet another embodiment, the described phosphatases and homologues thereof consist of a protein, polypeptide, or polynucleotide encoding a sequence of amino acid residues having one or more of the sequences KEKLTVSFVGNHDGEVHD (SEQ ID NO: 57), KERLTLSYVGNHDGEVHD (SEQ ID NO 58), REKLTLTYVGNHDGQVHD (SEQ ID NO: 59), and KEKLTLTYIGNHDGQVHD (SEQ ID NO: 60) or a protein, polypeptide, or polynucleotide encoding a protein having a homologous sequence to one of the foregoing sequences with only conservative substitutions, as described above, to those sequences.

In a further embodiment, the described phosphatases and homologues thereof consist of a protein, polypeptide, or polynucleotide encoding a sequence of amino acid residues having the sequence (F/Y)(V/I)GNHDGXXH (SEQ ID NOS: 61-64), where the first residue of the sequence can be F or Y and the second residue of the sequence can be V or I. In a still further embodiment, the described phosphatases and homologues thereof consist of a protein, polypeptide, or polynucleotide encoding a sequence of amino acid residues having the sequence (F/Y)(V/I)GNHDGXXH (SEQ ID NOS: 61-64), where the first residue of the sequence can be F or Y and the second residue of the sequence can be V or I, or a protein, polypeptide, or polynucleotide encoding a protein having a homologous sequence to the foregoing sequence with only conservative substitutions, as described above, to the foregoing sequence. In a yet still further embodiment, the described phosphatases and homologues thereof consist of a protein, polypeptide, or polynucleotide encoding a sequence of amino acid residues having the sequence (F/Y)(V/I)GNHDGXXH (SEQ ID NOS: 61-64), where the first residue of the sequence can be F or Y and the second residue of the sequence can be V or I, or a protein, polypeptide, or polynucleotide encoding a protein having a homologous sequence having at least about 70% identity and/or conservative substitution, as described above, to the foregoing sequence.

In one embodiment, the described phosphatases and homologues thereof consist of a protein, polypeptide, or polynucleotide encoding a sequence of amino acid residues having at least about 60% or more identity and/or conservative substitutions to amino acid residues 614-636 of SEQ ID NO: 2 (SEQ ID NO: 65) and/or having at least about 60% or more identity and/or conservative substitutions to the sequence of 23 amino acid residues of SEQ ID NOS: 4, 6, 8, 19, 21, 23, 25, 27, 29, 31, 33 and 47 aligned with residues 614-636 of SEQ ID NO: 2 (SEQ ID NO: 65), and where amino acid residues aligned with amino acid residues 614-636 of SEQ ID NO: 2 are predicted to form a transmembrane-like C-terminal motif by TMHMM analysis (http://www.cbs.dtu.dk/services/TMHMM/). In one embodiment, the described phosphatases and homologues thereof consist of a protein, polypeptide, or polynucleotide encoding a sequence of amino acid residues having at least about 70% or more identity and/or conservative substitutions to amino acid residues 614-636 of SEQ ID NO: 2 (SEQ ID NO: 65) and/or having at least about 60% or more identity and/or conservative substitutions to the sequence of 23 amino acid residues of SEQ ID NOS: 4, 6, 8, 19, 21, 23, 25, 27, 29, 31, 33 and 47 aligned with residues 614-636 of SEQ ID NO: 2 (SEQ ID NO: 65), and where amino acid residues aligned with amino acid residues 614-636 of SEQ ID NO: 2 (SEQ ID NO: 65) are predicted to form a transmembrane-like C-terminal motif by TMHMM analysis (http://www.cbs.dtu.dk/services/TMHMM/). In one embodiment, the described phosphatases and homologues thereof consist of a protein, polypeptide, or polynucleotide encoding a sequence of amino acid residues having at least about 80% or more identity and/or conservative substitutions to amino acid residues 614-636 of SEQ ID NO: 2 and/or having at least about 60% or more identity and/or conservative substitutions to the sequence of 23 amino acid residues of SEQ ID NOS: 4, 6, 8, 19, 21, 23, 25, 27, 29, 31, 33 and 47 aligned with residues 614-636 of SEQ ID NO: 2 (SEQ ID NO: 65), and where amino acid residues aligned with amino acid residues 614-636 of SEQ ID NO: 2 (SEQ ID NO: 65) are predicted to form a transmembrane-like C-terminal motif by TMHMM analysis (http://www.cbs.dtu.dk/services/TMHMM/). In one embodiment, the described phosphatases and homologues thereof consist of a protein, polypeptide, or polynucleotide encoding a sequence of amino acid residues having at least about 90% or more identity and/or conservative substitutions to amino acid residues 614-636 of SEQ ID NO: 2 and/or having at least about 90% or more identity and/or conservative substitutions to the sequence of 23 amino acid residues of SEQ ID NOS: 4, 6, 8, 19, 21, 23, 25, 27, 29, 31, 33 and 47 aligned with residues 614-636 of SEQ ID NO: 2, and where amino acid residues aligned with amino acid residues 614-636 of SEQ ID NO: 2 are predicted to form a transmembrane-like C-terminal motif by TMHMM analysis (http://www.cbs.dtu.dk/services/TMHMM/).

In one embodiment, the described phosphatases or phosphatase genes consist of a protein, polypeptide, or polynucleotide encoding the sequence (L/M/V)-(L/MN)-Z-(G/A)-(V/A/L)-Z-Z-G-(F/Y)-X-Z-G (SEQ ID NO: 66), where Z is any of the hydrophobic residues L, I, V, F, and M. In another embodiment, the described phosphatase or phosphatase genes consist of a protein, polypeptide, or polynucleotide encoding the sequence (L/M/V)-(L/MN)-Z-(G/A)-(V/A/L)-Z-Z-G-(F/Y)-X-Z-G (SEQ ID NO: 66), or a protein, polypeptide, or polynucleotide encoding a sequence having at least 70% identity and/or conservative substitution to the foregoing sequence.

Embodiments also encompass derivatives of the disclosed polypeptides. For example, but not by way of limitation, derivatives may include peptides or proteins that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, etc. Additionally, the derivative may contain one or more non-classical amino acids.

In another aspect, an isolated nucleic acid molecule encodes a variant of a polypeptide in which the amino acid sequences have been modified by genetic engineering so that biological activities of the polypeptides are either enhanced or reduced, or the local structures thereof are changed without significantly altering the biological activities. In one aspect, these variants can act as either agonists or as antagonists. An agonist can retain substantially the same or a portion of the biological activities of the polypeptides and an antagonist can inhibit one or more of the activities of the polypeptides. Such modifications include amino acid substitution, deletion, and/or insertion. Amino acid modifications can be made by any method known in the art and various methods are available to and routine for those skilled in the art.

For example, mutagenesis may be performed in accordance with any of the techniques known in the art including, but not limited to, synthesizing an oligonucleotide having one or more modifications within the sequence of a given polypeptide to be modified. Site-specific mutagenesis can be conducted using specific oligonucleotide sequences which encode the nucleotide sequence containing the desired mutations in addition to a sufficient number of adjacent nucleotides in the polypeptide. Such oligonucleotides can serve as primers which can form a stable duplex on both sides of the deletion junction being traversed. Typically, a primer of about 15 to about 75 nucleotides or more in length is preferred, with about 10 to about 25 or more residues on both sides of the junction of the sequence being altered. A number of such primers introducing a variety of different mutations at one or more positions can be used to generate a library of mutants.

The technique of site-specific mutagenesis is well known in the art, as described in various publications (e.g., Kunkel et al., Methods Enzymol., 154:367-82, 1987, which is hereby incorporated by reference in its entirety). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as T7 DNA polymerase, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phages are readily commercially available and their use is generally well known to those skilled in the art. Double stranded plasmids are also routinely employed in site directed mutagenesis which eliminates the step of transferring the gene of interest from a plasmid to a phage.

Alternatively, the use of PCR with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic et al., *Nucleic Acids Res.,* 18(6):1656, 1987, and Upender et al., *Biotechniques,* 18(1):29-30, 32, 1995, for PCR-mediated mutagenesis procedures, which are hereby incorporated in their entireties. PCR employing a thermostable ligase in addition to a thermostable polymerase may also be used to incorporate a phosphorylated mutagenic oligonucleotide into an amplified DNA fragment that may then be cloned into an appropriate cloning or expression vector (see e.g., Michael, *Biotechniques,* 16(3):410-2, 1994, which is hereby incorporated by reference in its entirety).

Other methods known to those skilled in art of producing sequence variants of a given polypeptide or a fragment thereof can be used. For example, recombinant vectors encoding the amino acid sequence of the polypeptide or a fragment thereof may be treated with mutagenic agents, such as hydroxylamine, to obtain sequence variants.

Optionally, the amino acid residues to be modified are surface exposed residues. Additionally, in making amino acid substitutions, preferably the amino acid residue to be substituted is a conservative amino acid substitution, for example, a polar residue is substituted with a polar residue, a hydrophilic residue with a hydrophilic residue, hydrophobic residue with a hydrophobic residue, a positively charged residue with a positively charged residue, or a negatively charged residue with a negatively charged residue. Moreover, the amino acid residue that can be modified is not highly or completely conserved across strains or species and/or is critical to maintain the biological activities of the protein.

Accordingly, included in the scope of the disclosure are nucleic acid molecules encoding a polypeptide of the invention that contains amino acid modifications that are not critical to its biological activity.

5.3 Fusion Proteins

The present disclosure further encompasses fusion proteins in which the polypeptides or fragments thereof, are recombinantly fused or chemically conjugated (e.g., covalent and non-covalent conjugations) to heterologous polypeptides (i.e., an unrelated polypeptide or portion thereof, preferably at least 10, at least 20, at least 30, at least 40, at least 50, at least 60, at least 70, at least 80, at least 90 or at least 100 amino acids of the polypeptide) to generate fusion proteins. The fusion can be direct, but may occur through linker sequences.

In one aspect, the fusion protein comprises a polypeptide which is fused to a heterologous signal sequence at its N-terminus. For example, the signal sequence naturally found in the polypeptide can be replaced by a signal sequence which is derived from a heterologous origin. Various signal sequences are commercially available.

In another embodiment, a polypeptide can be fused to tag sequences, e.g., a hexa-histidine peptide, among others, many of which are commercially available. As described in Gentz et al., 1989*, Proc. Natl. Acad. Sci. USA,* 86:821-824, for instance, hexa-histidine provides for convenient purification of the fusion protein. Other examples of peptide tags are the hemagglutinin "HA" tag, which corresponds to an epitope derived from the influenza hemagglutinin protein (Wilson et al., 1984*, Cell,* 37:767) and the "flag" tag (Knappik et al., 1994*, Biotechniques,* 17(4):754-761). These tags are especially useful for purification of recombinantly produced polypeptides.

Fusion proteins can be produced by standard recombinant DNA techniques or by protein synthetic techniques, e.g., by use of a DNA synthesizer. For example, a nucleic acid molecule encoding a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992).

The nucleotide sequence coding for a fusion protein can be inserted into an appropriate expression vector, i.e., a vector which contains the necessary elements for the transcription and translation of the inserted protein-coding sequence.

In a specific embodiment, the expression of a fusion protein is regulated by an inducible promoter.

5.4 Preparation of Transgenic Plants

Carbon flow is a key process in plant biology and high energy carbon molecules (e.g. glucose) were harvested by plant through photosynthesis. The carbon molecules were then converted into more complicated carbohydrate molecules such as starch, cellulose, etc. Cellulose is the major component of cell wall and starch is the major storage form of glucose in plant cells and plant seeds. Therefore, the efficiency and/or the equilibrium of the carbon flow process become a limiting factor for plant growth and crop yield.

The present disclosure is based upon the discovery that overexpression of a membrane-bound phosphatase can enhance the growth performance of plants by altering its carbon metabolism, as indicated by, for example, a faster growth rate, a higher sugar contents, and a higher seed yield.

In an embodiment, the present disclosure provides a transgenic plant containing a nucleic acid molecule that encodes and expresses a phosphatase having a C-terminal transmembrane-like domain. The transgenic plants disclosed herein have faster growth rate, and higher seed yield to comparable unengineered plants i.e. same species (strain). In a specific embodiment, such a phosphatase is from a plant species having a phosphatase activity and a C-terminal motif. In another embodiment, a transgenic plant disclosed herein comprises a nucleic acid molecule encoding phosphatase and expresses AtPAP2 (SEQ ID NO: 2) and/or other PAPs with a C-terminal motif including one or more of SEQ ID NOS: 4, 6, 8, 19, 21, 23, 25, 27, 29, 31, 33, 35, 37, 39, 41, 43, 45 and 47. In another embodiment, the phosphatase is expressed on cellular membrane, for example, the ER or the Golgi apparatus. Such a membrane expression of a phosphatase in plants can be achieved by fusing onto the C-terminus with a nucleotide sequence encoding a C-terminal motif peptide which can efficiently attach the phosphatase upon translation thereof from the cells of a given plant. Accordingly, in another embodiment, a transgenic plant comprises a nucleic acid molecule encoding phosphatase and expresses AtPAP2 (SEQ ID NO: 2) and/or other PAPs with a C-terminal motif including SEQ ID NOS: 4, 6, 8, 19, 21, 23, 25, 27, 29, 31, 33, 35, 37, 39, 41, 43, 45 and 47, except that all or a portion, particularly an N-terminal portion, of amino acid residues 1 to 80, preferably all or a portion of amino acid residues 1 to 30, of SEQ ID NO: 2 or all or a portion, particularly an N-terminal portion, of amino acid residues 1 to 80, preferably all or a portion of amino acid residues 1 to 30, of SEQ ID NOS: 4, 6, 8, 19, 21, 23, 25, 27, 29, 31, 33, 35, 37, 39, 41, 43, 45 or 47, are replaced by a heterologous plant signal peptide by genetic engineering. In such a transgenic plant, the phosphatases are directed to various organelles/compartments of the cells. In another embodiment, a transgenic plant comprises a nucleic acid molecule encoding phosphatase and expresses homologues, derivatives, and/or fragments thereof having at least one functional feature and/or structural feature of a phosphatase polypeptide. In all embodiments where all or a portion of the N-terminal portion of SEQ ID NOS: 4, 6, 8, 19, 21, 23, 25, 27, 29, 31, 33, 35, 37, 39, 41, 43, 45 and/or 47 are replaced, the embodiments include homologues to such sequences, as described above, having at least one functional feature and/or structural feature of a phosphatase polypeptide. In yet another embodiment, a transgenic plant comprises a nucleic acid molecule that hybridizes under stringent conditions, as defined herein, to a nucleic acid molecule having the sequence of SEQ ID NOS: 1, 3, 5, 7, 18, 20, 22, 24, 26, 28, 30, 32, 34, 36, 38, 40, 42, 44 or 46, or a complement thereof, and encodes a protein or polypeptide that exhibits at least one structural and/or functional feature of the disclosed phosphatase polypeptides. Specifically, the production of transgenic plant that overexpressed a membrane-bound phosphatase, which contributes to improving plant physiology, such as plant growth rate and characteristics, for example, in seed yield, is provided.

Accordingly, also provided are chimeric gene constructs for genetic modification of plants to increase their growth rate and improve the yield. The chimeric gene constructs comprise a sequence that encodes substantially solely for a phosphatase enzyme that carry a C-terminal transmembrane-like motif. Such a phosphatase enzyme can be derived from the purple acid phosphatase family. In a specific embodiment, the chimeric gene constructs comprise a nucleic acid having the sequence of SEQ ID NOS: 1, 3, 5, 7, 18, 20, 22, 24, 26, 28, 30, 32, 34, 36, 38, 40, 42, 44 or 46. In another embodiment, the chimeric gene constructs comprise a nucleic acid molecule that encodes a homologue or fragment thereof having at least one functional feature and/or structural feature of a phosphatase polypeptide. In another specific embodiment, the chimeric gene constructs comprise a sequence that hybridizes under stringent conditions, as defined herein, to a nucleic acid having the sequence of SEQ ID NOS: 1, 3, 5, 7, 18, 20, 22, 24, 26, 28, 30, 32, 34, 36, 38, 40, 42, 44 or 46, or a complement thereof, wherein the sequence encodes a protein or a polypeptide that exhibits at least one structural and/or functional feature of the phosphatase polypeptides. Furthermore, the phosphatases encoded by the nucleic acid molecules contained in the chimeric gene constructs can be any other phosphatases that have similar structural characteristics, such as having a C-terminal transmembrane-like motif, to those of the phosphatases described herein. Such phosphatase include, but not limited to, the following polypeptides: Purple acid phosphatases from *Zea mays* (Accession No: ACG47621); and *Oryza sativa* (Accession No: BAC15853.1).

The phosphatase-coding sequence is operatively linked to upstream and downstream regulatory components, preferably heterologous to the phosphatase sequence; for example CMV 35S promoter, which acts to cause expression of the gene (production of the enzyme) in plant cells (see Section 6.2). When a construct containing a gene for a phosphatase according to this disclosure, is introduced into plant cells by a conventional transformation method, such as microparticle bombardment, *Agrobacterium* infection, or microinjection, the gene is expressed in the cells under the control of the regulatory sequences. The expressed phosphatase successfully interacts with the biosynthetic machinery that is naturally present in the plant cells to alter the carbon metabolism. By altering the carbon metabolism, the method described herein also favors the growth rate of the plant, resulting in faster growth rate and higher yield. Thus, the time required for the maturation of the plant and the time required for flowering is shortened. Also provided are methods for increasing growth rate and yield of plants, comprising the step of inserting into such plant cells or the cells of such whole plants a chimeric gene construct.

In specific embodiments, *Arabidopsis* (see Section 6) was adopted as the model system. An overexpression construct the gene coding for phosphatase were introduced into *Arabidopsis*.

In an embodiment, the phosphatase from *Arabidopsis* is used. The results obtained with this disclosure indicate that the growth rate and the seed yield of transgenic *Arabidopsis* were enhanced by overexpressing this gene (see Section 6.5 and FIG. 8 and Table 3).

While any plant species can be modified using the expression cassette and methods described herein, preferably included without limitation are species from the following genera with representative species in parentheses:

Monocots: genera *Asparagus* (*asparagus*), *Bromus* (cheatgrass), *Hemerocallis* (daylily), *Hordeum* (barley), *Lolium* (ryegrass), *Oryza* (rice), *Panicum* (Switchgrass), *Pennisetum* (fountaingrass), *Saccharum* (Sugar cane), *Sorghum, Trigonella* (fenu grass), *Triticum* (wheat), *Zea* (corn); and Dicots: genera *Antirrhinum* (flower sp.), *Arabidopsis* (thaliana), *Arachis* (peanut), *Atropa* (deadly nightshade), *Brassica* (rapeseed), *Browallia, Capsicum* (pepper), *Carthamus* (safflower), *Cichorium* (chicory), *Citrus* (orange, lemon), *Chrysanthemum, Cucumis* (cucumber), *Datura* (thorn apple), *Daucus* (carrot), *Digitalis* (foxglove), *Fragaria* (strawberry), *Geranium* (flower sp.), *Glycine* (soybean), *Helianthus* (sunflower), *Hyscyamus, Ipomoea* (morning glory), *Latuca* (lettuce), *Linum* (linseed), *Lotus* (flower sp.), *Lycopersicon* (tomato), *Majorana, Malva* (cotton), *Manihot, Medicago* (alfalfa), *Nemesia, Nicotiana* (tobacco), *Onobrychis, Pelargonium* (citrosa), *Petunia* (flower sp.), *Ranunculus* (flower sp.), *Raphanus* (radishes), *Salpiglossis, Senecio* (flower sp.), *Sinapis* (albae semen), *Solanum* (potato), *Trifolium* (clovers), *Vigna* (mungbean, faba bean), *Vitis* (grape).

Genetic engineering of plants can be achieved in several ways. The most common method is *Agrobacterium*-mediated transformation. In this method, *A. tumefaciens*, which in nature infects plants by inserting tumor causing genes into a plant's genome, is altered. Selected genes are engineered into the T-DNA of the bacterial Ti (tumor-inducing) plasmid of *A. tumefaciens* in laboratory conditions so that they become integrated into the plant chromosomes when the T-DNA is transferred to the plant by the bacteria's own internal transfer mechanisms. The only essential parts of the T-DNA are its two small (25 base pair) border repeats, at least one of which is needed for plant transformation. The bacterial genes encoding for plant hormones that promote tumor growth are excised from the T-DNA and replaced with a sequence of DNA that typically contains: a selectable marker (e.g. an antibiotic-resistance gene; usually kanamycin resistance), a restriction site—a site with a specific sequence of nucleotides where a restriction enzyme will cut the DNA, and the desired genes to be incorporated into the plant (B. Tinland, 1996. The integration of T-DNA into plant genomes. Trends in Plant Science 1, 178-184; D. Grierson (ed.) 1991. Plant Genetic Engineering. Blackie, Glasgow). *Agrobacterium* can be added to plant protoplasts (plant cells with cell walls removed) in culture, that are then allowed to regenerate cell walls at which point non-transformed plants are killed with antibiotics for which the transformed plants have been given resistance genes. Plantlets are then regenerated from the surviving transformed cells using standard plant tissue culture techniques. In an alternative technique, sterile disks or fragments of vegetative portions of plants are place in liquid culture medium with *Agrobacterium*, then hormones are used to induce rooting thereby regenerate plantlets which are grown on selection media. A third technique for delivering genes is possible for some plants such as *Arabidopsis* where the *Agrobacterium* or even "naked" DNA can be infused through the seed coat to cause transformation (Clough S J and Bent A F, 1998. Floral dip: a simplified method for *Agrobacterium*-mediated transformation of *Arabidopsis thaliana*. Plant J 16:735-43).

The biolistic method for genetic engineering of plants was developed more recently and is becoming more widely employed. In this method, very small particles (microprojectiles) of tungsten or gold coated with biologically active DNA are propelled at high-velocities into plant cells using an electrostatic pulse, air pressure, or gunpowder percussion. As the particles pass through the cell, the DNA dissolves and can then integrate into the genome of that cell and its progeny. It has been demonstrated this method can produce stable transformants (Christou, P., et al., 1988. Stable transformation of soybean callus by DNA-coated gold particles, *Plant Physiology* 87:671-674). The method can be practiced on whole plants and is particularly effective on meristematic tissue. It is also capable of delivering DNA either to the nucleus or into mitochondria (Johnston, S. A., et al., 1988. Mitochondrial transformation in yeast by bombardment with microprojectiles (Science 240, 1538-41) and chloroplasts (Svab, Z., et al., 1990, Stable transformation of plastids in higher plants, *Proc Natl Acad. Sci. USA* 87, 8526-8530).

The electroporation method of plant genetic engineering has met with less success. In this technique, protoplasts in culture take up pure DNA when treated with certain membrane-active agents or with electroporation, a rapid pulse of high-voltage direct current. Once the DNA has entered the protoplast it can be integrated into the cells genome. Standard tissue culture techniques are then used to regenerate transgenic plants.

The microinjection method of plant genetic engineering is perhaps the most difficult. In this method, DNA is microinjected into target plant cells using very thin glass needles in a method similar to that used with animals. The technique is laborious, ineffective, and impractical for generating large numbers of transgenic plants.

The method chosen for genetically engineering plants is most often dependent on the targeted plant species and which methods have been proven effective therein.

5.5 Preparation of Antibodies

Antibodies which specifically recognize one of the described phosphatase polypeptides or fragments thereof can be used for detecting, screening, and isolating the polypeptide of the invention or fragments thereof, or similar sequences that might encode similar enzymes from the other organisms. For example, in one specific embodiment, an antibody which immunospecifically binds AtPAP2 or fragments thereof can be used for various in vitro detection assays, including enzyme-linked immunosorbent assays (ELISA), radioimmunoassays, Western blot, etc., for the detection of the polypeptide of the invention or fragments, derivatives, homologues, or variants thereof, or similar molecules having the similar enzymatic activities as the phosphatase polypeptides, in samples, for example, a biological material, including plant cells, plants, food, drinks, or any materials derived from plants.

Antibodies specific for the described phosphatase polypeptides can be generated by any suitable method known in the art. Polyclonal antibodies to an antigen-of-interest can be produced by various procedures well known in the art. For example, an antigen derived from the phosphatase polypeptide can be administered to various host animals including, but not limited to, rabbits, mice, rats, etc., to induce the production of antisera containing polyclonal antibodies specific for the antigen. Various adjuvants may be used to increase the immunological response, depending on the host species, and include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (*Bacille Calmette-Guerin*) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas*, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by known techniques. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the complete light chain, and the variable region, the CH1 region and the hinge region of the heavy chain.

The antibodies or fragments thereof can be also produced by any method known in the art for the synthesis of antibodies, in particular, by chemical synthesis or preferably, by recombinant expression techniques.

The nucleotide sequence encoding an antibody may be obtained from any information available to those skilled in the art (i.e., from Genbank, the literature, or by routine cloning). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., supra; and Ausubel et al., eds., 1998, *Current Protocols in Molecular Biology*, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies or any portion of antibodies which may enhance or reduce biological activities of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof has been obtained, the vector for the production of the antibody molecule may be produced by recombinant DNA technology using techniques well known in the art as discussed in the previous sections. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression. Thus-prepared expression vector can be then introduced into appropriate host cells for the expression of the antibody. Accordingly, embodiments include host cells containing a polynucleotide encoding an antibody specific for the disclosed phosphatase polypeptides or fragments thereof.

The host cell can be co-transfected with two expression vectors, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, *Nature,* 322:52; and Kohler, 1980, *Proc. Natl. Acad. Sci. USA,* 77:2197). The coding sequences for the heavy and light chains may comprise cDNA or genomic DNA.

In another embodiment, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fvs, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phages used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, include those disclosed in Brinkman et al., 1995, *J. Immunol. Methods* 182:41-50; Ames et al., 1995, *J. Immunol. Methods* 184:177-186; Kettleborough et al., 1994, *Eur. J. Immunol.,* 24:952-958; Persic et al., 1997, *Gene,* 187:9-18; Burton et al., 1994, *Advances in Immunology* 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above documents, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and $F(ab)_2$ fragments can also be employed using methods known in the art such as those disclosed in PCT publication WO 92/22324; Mullinax et al., 1992, *BioTechniques* 12(6):864-869; and Sawai et al., 1995, AJRI 34:26-34; and Better et al., *Science,* 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., 1991, *Methods in Enzymology* 203:46-88; Shu et al., 1993, PNAS 90:7995-7999; and Skerra et al., 1988, *Science* 240:1038-1040.

Once an antibody molecule has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies or fragments thereof may be fused to heterologous polypeptide sequences described herein or otherwise known in the art to facilitate purification.

Antibodies fused or conjugated to heterologous polypeptides may be used in in vitro immunoassays and in purification methods (e.g., affinity chromatography) well known in the art. See e.g., PCT publication Number WO 93/21232; EP 439,095; Naramura et al., 1994, *Immunol. Lett.* 39:91-99; U.S. Pat. No. 5,474,981; Gillies et al., 1992, PNAS 89:1428-1432; and Fell et al., 1991, *J. Immunol.* 146:2446-2452, which are incorporated herein by reference in their entireties.

Antibodies may also be attached to solid supports, which are particularly useful for immunoassays or purification of the described polypeptides or fragments, derivatives, homologues, or variants thereof, or similar molecules having the similar enzymatic activities as the polypeptide of the invention. Such solid supports include, but are not limited to, glass, cellulose, polyacrylamide, nylon, polystyrene, polyvinyl chloride or polypropylene.

5.6 Detection Assays

An exemplary method for detecting the presence or absence of an overexpressed phosphatase polypeptide or an inserted phosphatase-encoding nucleic acid in a biological sample involves obtaining a biological sample from various sources and contacting the sample with a compound or an agent capable of detecting a polypeptide or nucleic acid (e.g., mRNA, genomic DNA) such that the presence of a heterologous polypeptide or nucleic acid is detected in the sample. An exemplary agent for detecting mRNA or genomic DNA encoding an inserted phosphatase polypeptide is a labeled nucleic acid probe capable of hybridizing to mRNA or genomic DNA encoding any of the described phosphatase polypeptides. The nucleic acid probe can be, for example, a full-length cDNA, such as the nucleic acid of SEQ ID NOS: 1, 3, 5, 7, 18, 20, 22, 24, 26, 28, 30, 32, 34, 36, 38, 40, 42, 44 or 46, or a portion thereof, such as an oligonucleotide of at least one of at least about 15, at least about 20, at least about 25, at least about 30, at least about 50, at least about 100, at least about 250, at least about 500, or more nucleotides in length and sufficient to specifically hybridize under stringent conditions to a mRNA or genomic DNA encoding a polypeptide of the invention.

An exemplary agent for detecting an over-expressed phosphatase polypeptide is an antibody capable of binding to a phosphatase polypeptide product of an inserted phosphatase gene, preferably an antibody with a detectable label. Antibodies can be polyclonal, or more preferably, monoclonal. An intact antibody, or a fragment thereof (e.g., Fab or $F(ab')_2$) can be used. See also the detailed descriptions about antibodies in Section 5.5.

The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The detection method can be used to detect mRNA, protein, or genomic DNA in a sample in vitro as well as in vivo. For example, in vitro techniques for detection of mRNA include Northern hybridizations and in situ hybridizations. In vitro techniques for detection of a heterologous polypeptide include enzyme linked immunosorbent assays (ELISAs), Western blots, immunoprecipitations and immunofluorescence. In vitro techniques for detection of genomic DNA include Southern hybridizations. Furthermore, in vivo techniques for detection of a heterologous polypeptide include introducing into a subject organism a labeled antibody directed against the polypeptide. For example, the antibody can be labeled with a radioactive marker whose presence and location in the subject organism can be detected by standard imaging techniques, including autoradiography.

In a specific embodiment, the methods further involve obtaining a control sample from a control subject, contacting the control sample with a compound or agent capable of detecting an over-expressed polypeptide product or the mRNA transcription product or genomic DNA encoding an inserted phospatase gene, such that the presence of the polypeptide or mRNA or genomic DNA encoding the phosphatase polypeptide is detected in the sample, and comparing the presence of the phosphatase polypeptide or mRNA or genomic DNA encoding the polypeptide in the control sample with the presence of the polypeptide or mRNA or genomic DNA encoding endogenous phosphatase polypeptides in the test sample.

Embodiments also encompass kits for detecting the presence of a heterologous polypeptide or nucleic acid in a test sample.

The kit, for example, can comprise a labeled compound or agent capable of detecting the polypeptide or mRNA encoding the polypeptide in a test sample and means for determining the amount of the polypeptide or mRNA in the sample (e.g., an antibody which binds the polypeptide or an oligonucleotide probe which binds to DNA or mRNA encoding the polypeptide). Kits can also optionally include instructions for use.

For antibody-based kits, the kit can comprise, for example: (1) a first antibody (e.g., attached to a solid support) which binds to a phosphatase polypeptide; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding an inserted phosphatase polypeptide or (2) a pair of primers useful for amplifying a nucleic acid molecule encoding an inserted phosphatase polypeptide. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for use.

5.7 Commercial Application of Transgenic Plants

The transgenic plants generated can have many useful applications, including food, feed, biomass, biofuels (starch, cellulose, seed lipids) and wood pulp. The enhanced growth rate of the transgenic plants may provide additional carbon dioxide fixation per hectare of land per year and thus generate carbon credits.

6. EXAMPLES

The following examples illustrate the cloning of AtPAP2, its overexpression in transgenic *Arabidopsis*, and the characterization of the transgenic plants. These examples should not be construed as limiting. The following examples illustrate some embodiments. Unless otherwise indicated in the following examples and elsewhere in the specification and claims, all parts and percentages are by weight, all temperatures are in degrees Centigrade, and pressure is at or near atmospheric pressure.

6.1 Sequence Alignment and Phylogenetic Analysis

PAP2 locus and its genomic organization, including its intron/exon boundaries, were identified in the *Arabidopsis* Col-0 ecotype (http://www.arabidopsis.org). Sequence alignment and phylogenetic tree were conducted using MEGA4 (Kumar et al., 2004) and ClustalW program (http://www.ebi.ac.uk/Tools/clustalw2/index.html). Amino acid sequence comparisons were performed using CLC Sequence Viewer 5.1.1 (www.cicbio.com).

Twenty nine PAP-like sequences were identified from the *Arabidopsis* genome and a phylogenetic tree was produced by neighbor-joining algorithm (FIG. 1). The gene locus of AtPAP2 (At1g13900) composes of two exons and the coding region is 1971 bp in length (SEQ ID NO: 1), which is predicted to encode a polypeptide of ~73.7-KD. Among the twenty nine PAP-like protein sequences, only AtPAP2 and AtPAP9 carry a unique hydrophobic motif at their C-termini by TMHMM analysis (http://www.cbs.dtu.dk/services/TMHMM-2.0/) (FIG. 3). AtPAP2 was found to share 72% sequence identity in amino acid sequence with AtPAP9. Two sequences from *Zea mays* (Accession No: ACG47621) and *Oryza sativa* (Accession No: BAC15853.1) were found to share 58% and 57% a.a. identity with AtPAP2, respectively. Their sequences were aligned in FIG. 2.

AtPAP2-like sequences from other plant species that carry a hydrophobic motif at their C-termini were retrieved by tblastn program from Plant GDB database (http://www.plantgdb.org/) and NCBI database (http://blast.ncbi.nlm.nih.gov/Blast.cgi) using the amino acid sequence of AtPAP2 as the search sequence. cDNA and protein sequences that share high homology with that of AtPAP2 were identified in *Zea mays* (SEQ ID NOs: 7 and 8), *Brassica rapa* (SEQ ID NOs: 18 and 19), *Hordeum vulgare* (SEQ ID NOs: 20 and 21), *Medicago truncatula* (SEQ ID NOs: 22 and 23), *Physcomitrella patens* (SEQ ID NOs: 24 and 25), *Populus trichocarpa* (SEQ ID NOs: 26 and 27), *Saccharum officinarum* (SEQ ID NOs: 28 and 29), *Solanum tuberosum* (SEQ ID NOs: 30 and 31), *Vitis vinifera* (SEQ ID NOs: 32 and 33), *Oryza sativa* (SEQ ID NOs: 34 and 35), *Gossypium hirsutum* (SEQ ID NOs: 36 and 37) *Panicum virgatum* (SEQ ID NOs: 38 and 39), *Solanum lycopersicum* (SEQ ID NOs: 40 and 41), *Sorghum bicolor* (SEQ ID NOs: 42 and 43) and *Triticum aestivum* (SEQ ID NOs: 44 and 45).

The cDNA sequences of AtPAP-like sequences were amplified from a local *Glycine max* variety (SEQ ID NO: 5) and the *Brassica napus* cultivar Westar (SEQ ID NO: 46) by RT-PCR using primers designed from corresponding EST sequences, which were retrieved from the Plant GDB database (http://www.plantgdb.org/).

6.2 Screening of T-DNA Line and Production of Overexpression Lines and Complementation Lines in *Arabidopsis*

T-DNA insertion lines of PAP2 gene (*Arabidopsis* genomic locus name: Salk_013567), in the Col ecotype were obtained from *Arabidopsis* Biological Resources Center (Alonso et al., 2003). Homologous T-DNA lines were identified by genomic PCR screening from SIGnAl database (http://signal.salk.edu/cgi-bin/tdnaexpress) by using the primers (LBa1, 5'-TGGTTCACGTAGTGGGCCATCG-3', SEQ ID NO: 9) and PAP2 specific forward primer (P2LP, 5'-TTGAAGTTTAACATGCCTGGG-3, SEQ ID NO: 10) and reverse primer (P2RP, 5'-TCCAATGCTCGA TTGATTAGC-3', SEQ ID NO: 11). The PCR product was sequenced and the T-DNA insertion site was confirmed. To exclude the possibility that another T-DNA locus interferes with the PAP2 mutant site, homologous pap2 mutant lines were backcrossed to the wild-type to dilute the potential T-DNA sites. The produced heterozygous pap2 mutants were grown on the MS plates containing 50 mg/ml Kanamycin. The ratio of the resistant to sensitive plants was about 3:1. These results demonstrated a single insertion locus site of the T-DNA line (pap2-8) lines.

The inability of the T-DNA line to express full length AtPAP2 mRNA was confirmed by RT-PCR. Total RNA was extracted from 10-day-old seedlings grown on MS with 2% (w/v) sucrose using the ThIzol RNA isolation method (Invitrogen) with DNase I treatment. cDNAs were generated using Superscript III reverse transcriptase (Invitrogen, Carlsbad, Calif., USA) using an oligo dT primer. Two gene-specific primers, P2YF (5'-GGCCGTCGACATGATCGTTAATT TCTCTTTC-3'SEQ ID NO: 12) and P2NR (5'-CCGGACTAGTTCATGTCTCCTCGTTCTTGAC-3' SEQ ID NO: 13), were used to amplify a 1971 bp coding region of AtPAP2. For each sample, 1 μg of cDNA was amplified for 30 cycles, with an annealing temperature of 50° C. and using elongation factor (EF) primers, EF-1 (5'-GTTTCACATCAACATTGTGGTCA TTGG-3, SEQ ID NO: 14) and EF-2 (5'-GAGTACTTGGGGGTAGTGGCATCC-3, SEQ ID NO: 15) (Axelos et al., 1989) for control experiment.

The inability of the T-DNA line to express protein was confirmed by Western blotting analysis (FIG. 4). Antiserum specific to AtPAP2 was raised in rabbit as described in Section 6.3.

Figure 5:
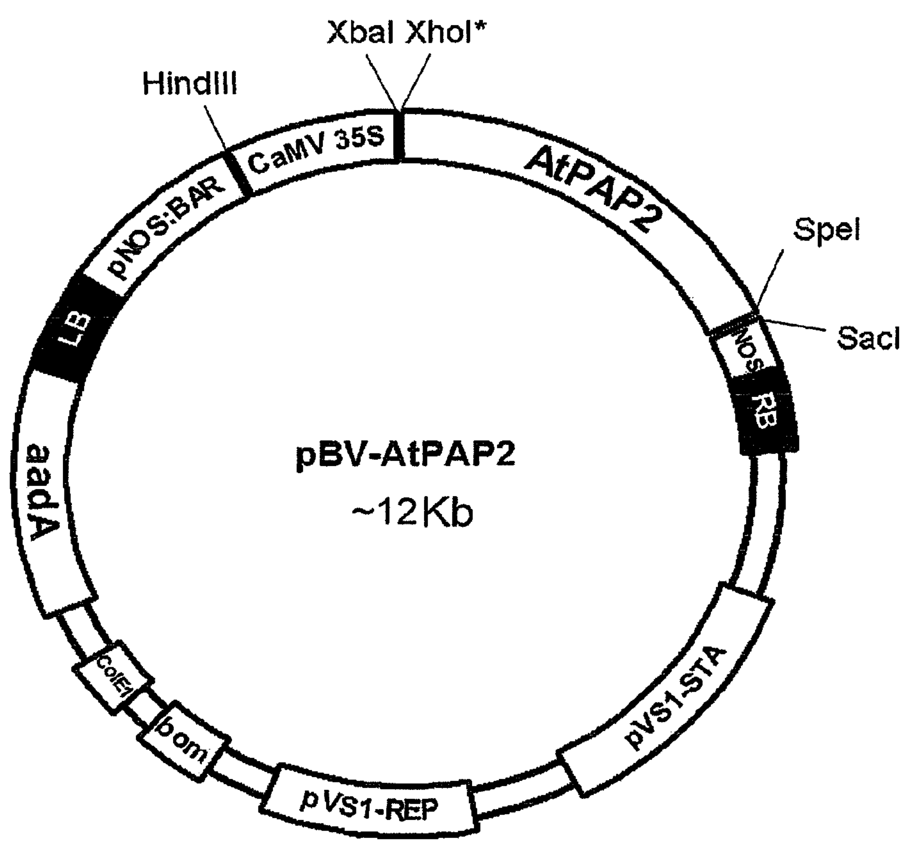
FIG. 5 is the schematic diagram of the expression vector pBV-AtPAP2. CaMV 35S:35S promoter of the cauliflower mosaic virus; NOS: polyadenylation signal of nopaline synthase gene; aadA: bacterial streptomycin/spectinomycin resistance gene encoding aminoglycoside-3"-adenyltransferase; pNOS:BAR: bialaphos resistance gene under the control of the nopaline synthase promoter; born: basis of mobility from pBR322; ColE1: replication origin from pBR322; pVS1-REP: replication origin from pVS1; pVS1-STA: STA region from pVS1 plasmid; LB: left border T-DNA repeat; RB: right border T-DNA repeat. (Hajdukiewicz et al., 1994).

To create transgenic AtPAP2 overexpressing lines or expressing this gene in the knockout mutants, the full length coding region of the AtPAP2 cDNA was amplified by PCR using primers P2YF (SEQ ID NO: 12) and P2NR (SEQ ID NO: 13). A SalI site and a SpeI site were engineered into P2YF and P2NR, respectively. The resulting product (1976 bp) was inserted into the XhoI/Spe I sites of a binary vector, immediately downstream to the cauliflower mosaic virus (CaMV) 35S promoter (FIG. 5).

The vector was introduced into *Agrobacterium tumefaciens* strain GV3101 and then transformed by the floral dip method (Clough and Bent, 1998), into wild-type Col-0 to generate PAP2-overexpressing lines or into homologous pap2 plants (T-DNA lines) to generate complementation lines. Through 2 generations of selection on MS agar plate with 50 mg/l Basta (Riedel-deHaen), homologous 35S:PAP2 transgenic lines were obtained. The resistant plants were transferred to soil to grow to maturity, and their transgenic status was further confirmed by PCR and immunoblot analyses. As shown in FIG. 6A, AtPAP2 protein was overexpressed in OE lines but was absence from the T-DNA line. The homozygous T3 seeds of the transgenic plants were used for further analysis.

To create transgenic AtPAP15 overexpression lines, the cDNA of AtPAP15 was also amplified by RT-PCR and then subcloned into a plant binary vector which bared a kanamycin-resistant gene and a cauliflower mosaic virus 35S promoter (CaMV). This expression construct named was then mobilized into *Agrobacterium tumefaciens* strain EHA105 by freeze-thaw transformation (Hofgen and Willmitzer, 1988) and transformed into *Arabidopsis*. Transgenic status was further confirmed by PCR and immunoblot analyses using an anti-AtPAP15 antiserum. As shown in FIG. 6B, AtPAP15 protein was overexpressed in OE lines. The homozygous T3 seeds of the transgenic plants were used for further analysis.

6.3 Production of PAP2 Polycolonal Antiserum and Western Blots Analysis

A fragment of AtPAP2 cDNA corresponding to the N terminal 120 amino acids (from 21 to 141) was amplified using forward primer P2AF (5'-GGTTGAGCTCGATTCTAAAGCGACCATTTC-3', SEQ ID NO: 16) and reverse primer P2AR (5'-TTTTGGTACCTCAGGATCCGAA AGTCAGC-3', SEQ ID NO: 17). The PCR product was cleaved by SacI and KpnI and cloned into the pRsetA vector (Invitrogen) so that the coding sequence of the first 120 a.a. of AtPAP2 was fused to a His-tag sequence. The resulting plasmid was transformed into *Escherichia coli* strain BL21 (DE3). The BL21 cells were induced at 30° C. by 0.1 mM isopropylthio-β-D-galactoside for 4 h and resuspended in 100 mM NaCl and 50 mM Tris-HCl, pH 7.5, 2 mM phenylmethylsulphonyl fluoride (PMSF). The lysates were sonicated 5 times for 30 s each. The overexpressed His-AtPAP2 fusion proteins in inclusion bodies were centrifuged at 5000×g for 15 min, and the pellets were solubilized in 150 mM NaCl, 8 M urea, and 20 mM Tris-HCl, pH 7.5. The fusion proteins were purified on a HisTrap FF (GE Healthcare) column and were used for standard immunization protocols in rabbits.

6.4 Expression Analysis of AtPAP2 mRNA and its Protein Levels

The mRNA expression level of AtPAP2 was analyzed by the Spot History program (http://affymetrix.arabidopsisinfo/narrays/spothistory.pl) that presented the expression levels of a given gene in thousands of microarray (Affymetrix ATH1 microarray) database. Spot history analysis indicated that the expression of AtPAP2 was constitutive but is relative low in most experimental circumstances (FIG. 7*a*). To determine AtPAP2 expression levels, different tissues of wild-type *A. thaliana* (Col-0) were collected.

The expression level of proteins were also studied by western blotting, using the anti-AtPAP2 antiserum generated from Section 6.3. Total plant soluble protein was extracted from wild-type *A. thaliana*, T-DNA line, AtPAP2-overexpress lines in grinding buffer (Tris-HCl 50 mM, pH7.4 containing 150 mM NaCl, 1 mM EDTA, 0.2 mM PMSF) on ice. Protein extracts were centrifuged at 16000×g and supernatants were collected for Bradford protein concentration determination assay. Equal amount of protein samples (50-90 μg/lane in different experiments) were loaded and separated in 12% (w/v) SDS-PAGE. The separated proteins were transferred to Hybond C-Extra membranes (Amersham Biosciences) (400 mA, 1 h). Membranes were blocked with 5% (w/v) non-fat milk in TTBS washing buffer (pH 7.6) for 2 hours and probed with specific anti-AtPAP2 antiserum for 3 hours or overnight at an 1:1000 dilution at 4° C. After rinsing the membrane with three changes of TTBS washing buffer (20 mM Tris-HCl, pH7.6, 136 mM NaCl, 0.1% Tween20) in half an hour, HRP-labeled secondary antibody, diluted 1:10,000 in TTBS washing buffer was added. After 2 hours, the membrane was washed thrice before the bands were visualized by Enhanced Chemiluminescence method (Amersham Biosciences). As shown in FIG. 7*b*, AtPAP2 protein was expressed in all tissues tested (Leaf, Flower, Stem, Root, Silique) at equal levels. The protein expression level of AtPAP2 during germination was very stable too (FIG. 7*c*) and was independent of phosphorus status (FIG. 7*d*).

6.5 Growth Phenotypes of WT, T-DNA Line and OE Lines

*Arabidopsis* seeds were soaked in water at 4° C. for 3 days. The seeds were surface sterilized and sown on Murashige and Skoog (MS) medium supplemented with 2% (w/v) sucrose for 10 days. Seedlings with 2 rosette leaves of the same size were transferred to soil under Long Day (16 h light at 22° C./8 h dark at 18° C.) or Short Day (8 h light at 22° C./16 h dark at 18° C.) conditions in a plant growth chamber. Flowering time was started to be measured by scoring the number of rosette leaves and cauline leaves when the primary inflorescence florescence reached 1 cm above the rosette leaves. Ten to 20 plants were scored for each line (Liu et al., 2008; Wu et al., 2008).

The inflorescences of OE lines of AtPAP2 emerged earlier (5-6 days for Long Day, 14-16 days for Short Day) than that of the WT and T-DNA lines (Table 1). Under Long Day conditioning, the number of rosette leaves of the OE lines were less (5-6 leaves) than the WT during the emergence of inflorescence (Table 1 and FIG. 8). At day 28 (Long Day), the OE lines of AtPAP2 had more cauline leaves and inflorescences than the WT and T-DNA lines, but had less rosette leaves (Table 2.). This phenotype observation was repeated at least four times and the results of one of the experiments were shown here.

TABLE 1

AtPAP2 OE lines flowered at an earlier developmental stage.

| | Long Day (16 h/8 h) | | | | Short Day (8 h/16 h) | | | |
|---|---|---|---|---|---|---|---|---|
| Lines | AEI | SD | NRL | SD | AEI | SD | NRL | SD |
| Col-0 | 26.9 | 1.2 | 13.0 | 0.8 | 41.0 | 4.7 | 18.0 | 3.0 |
| T-DNA | 25.7 | 0.7 | 11.6 | 1.1 | 40.7 | 4.9 | 15.0 | 3.0 |
| OE7 | 20.0* | 1.1 | 6.4* | 0.5 | 25.6* | 1.3 | 5.3* | 0.5 |
| OE21 | 20.8* | 0.6 | 6.5* | 0.7 | 26.0* | 1.1 | 5.4* | 0.5 |

AEI: Average date of emergence of inflorescence
NRL: No. of rosette leaves at the first appearance of inflorescence
*Statistically ($p < 0.001$) different from the wild-type ($n = 15$).

TABLE 2

Phenotypes of AtPAP2 OE lines at Day 28 (Long Day).

| Lines | No. of Rosette Leaf | SD | No. of Cauline Leaf | SD | No. of Inflorescence | SD |
|---|---|---|---|---|---|---|
| Col-0 | 14.5 | 1.2 | 1.6 | 0.5 | 1.0 | 0.0 |
| T-DNA | 16.7 | 1.7 | 1.9 | 0.6 | 1.0 | 0.0 |
| OE7 | 9.9* | 1.0 | 6.0* | 1.2 | 3.6* | 0.7 |
| OE21 | 10.2* | 1.8 | 7.2* | 1.6 | 3.7* | 1.1 |

*Statistically ($p < 0.001$) different from the wild-type ($n = 15$).

At maturity (Long Day), the number of siliques and the total weight of seeds harvested from each line were recorded. Two separate experimental trials are shown in Tables 3A and 3B. Our results showed that overexpression of AtPAP2 resulted in increase number of siliques per plant and the seed yield per plant. Compared to that of the wild-type, the seed yield of the two overexpression lines shown in Table 3A increased 38-40%. Compared to that of the wild-type, the seed yield of the two overexpression lines shown in Table 3B increased 54-58%.

TABLE 3A

OE lines produced more siliques and seeds (Trial 1).

| Lines | No. of siliques/plant | SD | Weight of seeds (g)/plant | SD | N |
|---|---|---|---|---|---|
| Col-0 | 327.4 | 53.3 | 0.188 | 0.047 | 5 |
| T-DNA | 236.6* | 60.2 | 0.121* | 0.040 | 7 |
| OE7 | 453.2** | 62.1 | 0.264** | 0.039 | 5 |
| OE21 | 498.2# | 52.5 | 0.260** | 0.049 | 7 |

Statistically ($p < 0.02$*, $p < 0.01$**, $p < 0.001$#) different from the wild-type.

TABLE 3B

OE lines produced more siliques and seeds (Trial 2).

| Lines | No. of siliques/plant | SD | Weight of seeds (g)/plant | SD | N |
|---|---|---|---|---|---|
| Col-0 | 396.4 | 89.5 | 0.225 | 0.058 | 13 |
| T-DNA | 386.3 | 70.4 | 0.240 | 0.049 | 12 |
| OE7 | 610.9* | 76.6 | 0.351* | 0.050 | 7 |
| OE21 | 624.9* | 94.7 | 0.355* | 0.066 | 11 |

Statistically ($p < 0.0001$*) different from the wild-type.

However, the OE lines of AtPAP15 grew normally and were not different from the wild-types. Therefore, the enhanced growth performance was due to the overexpression of AtPAP2, which bears a transmembrane-like motif at its C-terminus (FIGS. 2 and 3).

6.6 Growth Phenotypes of Truncated AtPAP2 Constructs

Figure 12:
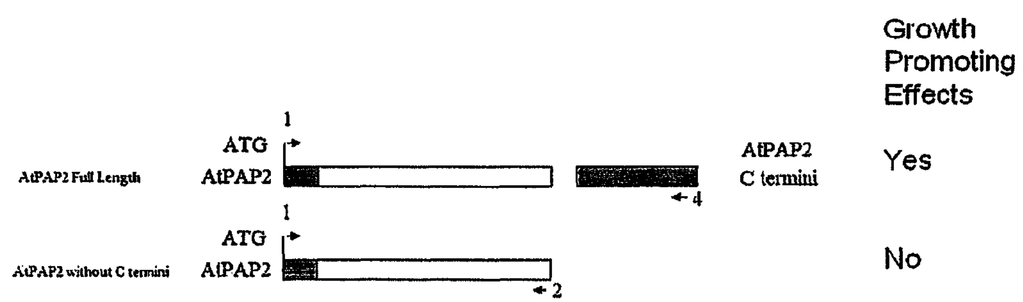
FIG. 12. shows a schematic representation of two vector constructs incorporating the AtPAP2 gene.
Figure 13:
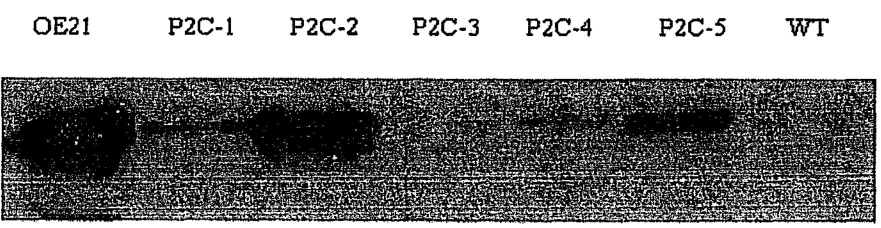
FIG. 13. shows Western blot analysis results for overexpression of AtPAP2 proteins missing the C-terminal motif.

An alternate vector construct employing the sequence for AtPAP2 was also constructed using analogous techniques to those described above. As shown in FIG. 12, a construct equivalent to the OE lines of AtPAP2 missing the C-terminal motif (residues 614-636 of SEQ ID NO: 2) was constructed (P2C lines). Transgenic plants were generated using substantially identical techniques to those described above. Western blot analysis was used to confirm the over-expression of the AtPAP2 fragment proteins in transformed plant lines. Performance of Western blot analysis was identical to that reported above. As show in FIG. 13, the P2C lines were strongly overexpressed. The growth phenotype of the P2C lines appeared to be indifferent from the wild-type, which is indicative of the importance of the C-terminal domain of AtPAP2 in developing an increased growth phenotype.

6.7 MS/MS Analysis of Sucrose and Glucose Levels in Leaf

Rosette leaves of plants of various developmental stages were harvested at the end of the light period of 21-day-old plants. Soluble sugars were extracted from *Arabidopsis* using chloroform/methanol method (Lunn et al., 2006; Antonio et al., 2007; Luo et al., 2007). 100 mg plant tissues were ground to a fine powder in liquid nitrogen and mixed and vortexed with 250 μl ice-cold chloroform:methanol (3:7, v/v). Soluble metabolites were then extracted at −20° C. overnight. 200 μl water was added to the mixture with repeated shaking. The extracts were centrifuged at 16000×g for 10 min and the supernatant was collected. The pellet was re-extracted by 200 μl water and the supernatant was collected by centrifugation as described above. The combined supernatant was evaporated to dryness using a SpeedVac and the pellet was re-dissolved in 200 μl water. Finally, debris was removed by centrifugation at 16000×g for 30 min.

20 μl filtered samples were analyzed by an API-3000 triple-quadrupole mass spectrometer (Applied Biosystems) via an electrospray ionization source. The parameters, optimized by 0-40 μg/ml glucose and sucrose standards, were as following: curtain gas (CUR) 25, nebulizer gas (GS1) 50, auxiliary gas (GS2) 30, ionspray voltage −4.5 k V, temperature 400° C., declustering potential (DP) −106 V, entrance potential (EP) −8.5 V, collision cell entrance potential (CEP) −46.7 V, collision energy (CE) 20 V. The peaks were identified by comparison with glucose and sucrose standards and the amount of sugars were quantified by standard curves of these sugars. The Analyst 1.3.1 software (Applied Biosystems) was used for data acquisition, peak integration, and calculation. The amount of sucrose and glucose at the end of day in the shoots of 21-day-old soil grown plants were shown in FIG. 9. It was found that the levels of both sugars were significantly higher than that in WT.

6.8 Recovery of Plants after Prolonged Darkness Treatment

Seeds of wild-type, T-DNA, OE7 and OE21 lines were germinated in MS (2% sucrose) medium for 10 days. Seedlings with 2 small visible rosette leaves (1 mm) of the same size were transferred to soil for another 12 days in normal growth conditions (LDs, 16 h/light (22° C.)/8 h darkness (18° C.)). The light source of the growth chamber was then switched off for 12 days. Then the plants were allowed to recover under the 16 h/light (22° C.)/8 h darkness (18° C.) cycle for 10 days. The plants that stayed green and that continued to emerge inflorescence were recorded in Table 4.

TABLE 4

Surviving rate and flowering ratio after prolonged darkness treatment.

| | Flowering after recovery | Recovery (leaf greening) |
|---|---|---|
| Wild-type | 8/12 | 11/12 |
| T-DNA | 5/12 | 8/12 |
| OE7 | 9/9 | 9/9 |
| OE21 | 12/12 | 12/12 |

Figure 10:
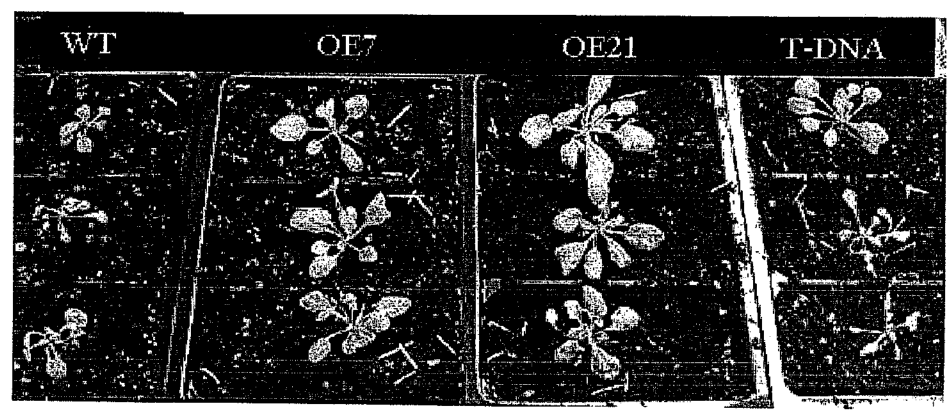
FIG. 10 shows the recovery of various lines after prolonged darkness treatment. Seeds were germinated in MS agar with 2% sucrose for 10 days. Seedlings with 2 small visible rosette leaves (~1 mm) were transferred to soil and grown for 12 days under 16 h/8 h light/dark cycles. The lights of the growth chamber were then switched off for 12 days and the plants were allowed to recover under 16 h/8 h light/dark cycles for 1 week. n=9-12 per line.

Extended darkness could induce carbohydrate starvation (Thompson et al., 2005). Our data showed that the OE lines exhibited 100% recovery rate under prolonged (12 days) darkness treatment, which was higher than that of the WT and the T-DNA line (FIG. 10). This could be attributed to a higher endogenous sugar levels (FIG. 9) in the OE lines.

6.9 Phenotypes of Plants Under NaCl and ABA Treatments 5-day-old seedlings grown on MS agar were transferred to MS agar with NaCl (50 mM, 100 mM, 150 mM), ABA (0.1 uM, 0.2 uM. 0.5 uM, 1 uM, 2 uM) or sorbitol (300 mM, 400 mM, 500 mM). Alternatively, seeds were directly germinated on the treatment media. Wild-type, T-DNA and OE lines did not show remarkable phenotypic differences under the above conditions.

6.10 Subcellular Fractionation

Rosette leaves of three-week-old wild-type (Col-0) *Arabidopsis* were harvested and stored at −80° C. freezer until use. Tissue (4-5 g) were ground to fine powder in liquid nitrogen using a mortar with a pestle. The powder was transferred into 10 ml grinding buffer (0.3 M sucrose, 40 mM Tris-HCl (pH 7.8), 5 mM $MgCl_2$, 1 mM PMSF) and swelled on ice for 5 min. Homogenization was performed for two 30-second pulses at high-speed setting. The homogenate was filtered through two layers of Miracloth (Tetko, Elmsford, N.Y., USA). Subsequently, the homogenate was separated by centrifugation at 350 g for 10 min at 4° C. The pellet (crude nuclear) was further layered onto 1 ml of 2.3 M sucrose, 50 mM Tris-HCl (pH 8.8), 5 mM $MgCl_2$ in an Eppendorf tube for centrifugation at 15,000 g 10 min at 4° C., to obtain the nuclear fraction in the derived pellet. Supernatants from the first low-speed centrifugation (350 g) were centrifuged at 12,000×g for 20 min at 4° C. The pellet contained large particles including mitochondria, chloroplasts and peroxisomes. The supernatant was further centrifuged at 100,000×g for 1 h at 4° C. to yield the soluble cytosol fraction in the resulting supernatant. The pellet representing the membrane fraction was resuspended in 0.1 ml grinding buffer. Protein concentration in the extract was determined following the method of Bradford (Bradford, 1976) using the Bio-Rad Protein Assay Kit I.

To isolate cell wall, leaf tissues were homogenized in grinding buffer (62.5 mM Tris-HCl, pH 7.5, 5 mM MT, 1% (v/v) bovine serum albumin, 2 mM phenylmethylsulfonyl fluoride, 2 μg/ml leupeptin, 2 μg/ml E-64, 2 μg/ml pepstatin A) using a Polytron (full speed, 3×10 s). The homogenate was centrifuged at 1,000×g for 3 min. The pellet was washed with ice-cold grinding buffer (without 1% BSA) 10 times. Finally the (cell wall) pellet was washed by resuspending in 500 mM $CaCl_2$, 20 mM NaCl, 62.5 mM Tris-HCl, pH 7.5, and spinning at 10,000×g for 15 min (He et al., 1996).

The subcellular fractions were run in a SDS-PAGE gel and were probed with anti-AtPAP2 antiserum. AtPAP2 was detected in membrane and soluble protein fractions but not in nucleus, mitochondria nor chloroplasts (FIG. 11).

In summary, *Arabidopsis* plants transformed with the AtPAP2 gene have the following phenotypes when they were compared with the wild-type: (1) Faster growth rate (Tables 1 and 2); (2) Higher sucrose content (FIG. 9); (3) Higher glucose content (FIG. 9); and (4) Higher crop yield (Table 3).

Those skilled in the art will recognize, or be able to ascertain many equivalents to the specific embodiments described herein using no more than routine experimentation. Such equivalents are intended to be encompassed by the following claims.

With respect to any figure or numerical range for a given characteristic, a figure or a parameter from one range may be combined with another figure or a parameter from a different range for the same characteristic to generate a numerical range.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present patent application.

While the embodiments have been explained in relation to certain embodiments, it is to be understood that various modifications thereof will become apparent to those skilled in the art upon reading the specification. Therefore, it is to be understood that the embodiments disclosed herein are intended to cover such modifications as fall within the scope of the appended claims. Features of two or more of any of the above embodiments can be combined to form additional embodiments.

Other than in the operating examples, or where otherwise indicated, all numbers, values and/or expressions referring to quantities of ingredients, reaction conditions, etc., used in the specification and claims are to be understood as modified in all instances by the term "about."

6.11 Assays of enzymes involved in sucrose metabolism

Sucrose phosphate synthesis (SPS), sucrose synthesis (SuSy), cytosolic invertase and cell wall invertase activities in the shoot of 20-day-old plants were determined. Samples were collected 8 h after the light and dark period (Long Day). SPS activity was measured under both optimal (Vmax) and limiting (V limit) assay conditions (Park et al., 2008). SuSy, cytosolic invertase and insoluble cell wall invertase activities were also determined (Doehlert, 1987). The assays were repeated three times and the SPS (Vmax and V limit) activities of both independent lines were significantly higher than that of the wild-type and T-DNA lines in all three repeated experiments. The data of a representative experiment is shown in table 5. In contrast to SPS, SuSy, cytosolic invertase and cell wall invertase activities were not different among the lines.

TABLE 5

| Enzyme assays | | | | |
|---|---|---|---|---|
| Plant line | WT | T-DNA | OE7 | OE21 |
| Sucrose phosphate synthase (μM sucrose/μg enzyme extracts/hour) | | | | |
| Vmax (Day) | 108.8 ± 18.1 | 116.1 ± 11.9 | 157.9 ± 21.7** | 159.5 ± 19.0** |
| Vlimit (Day) | 63.6 ± 6.4 | 69.5 ± 2.5 | 90.8 ± 18.5** | 79.8 ± 13.7* |
| Vmax (Night) | 118.3 ± 11.4 | 104.9 ± 14.4 | 150.9 ± 19.4** | 136.5 ± 15.1* |
| Vlimit (Night) | 74.9 ± 6.3 | 56.7 ± 3.3 | 93.4 ± 3.6** | 97.3 ± 10.9** |
| Sucrose synthase (μM glucose/μg enzyme extracts/hour) | | | | |
| Day | 249.2 ± 4.6 | 247.0 ± 24.0 | 248.6 ± 4.5 | 255.2 ± 5.4 |
| Night | 249.4 ± 7.2 | 252.7 ± 8.8 | 250.8 ± 8.7 | 258.8 ± 5.5 |
| Cytosolic invertase (μM glucose/μg enzyme extracts/hour) | | | | |
| Day (Acid) | 14.3 ± 2.3 | 12.1 ± 5.4 | 18.3 ± 9.1 | 18.0 ± 0.8 |
| Night (Acid) | 14.0 ± 6.8 | 26.1 ± 10.9 | 17.6 ± 4.3 | 13.8 ± 0.8 |
| Day (Alkaline) | 169.7 ± 9.8 | 161.2 ± 32.3 | 160.9 ± 27.9 | 178.8 ± 16.9 |
| Night (Alkaline) | 130.0 ± 8.2 | 105.1 ± 12.6 | 136.1 ± 13.6 | 136.6 ± 1.4 |
| Cell wall invertase (μM sucrose/μg enzyme extracts/hour) | | | | |
| Day (Acid) | 22.3 ± 3.9 | 18.0 ± 4.9 | 23.5 ± 6.3 | 24.0 ± 6.6 |
| Night (Acid) | 21.6 ± 10.1 | 17.0 ± 4.3 | 28.3 ± 4.2 | 22.3 ± 3.3 |
| Day (Alkaline) | 121.7 ± 2.8 | 127.1 ± 2.2 | 101.8 ± 6.4 | 105.5 ± 2.0 |
| Night (Alkaline) | 138.9 ± 6.3 | 151.5 ± 8.7 | 123.4 ± 5.6 | 135.4 ± 14.7 |

(**P < 0.01; *P < 0.05)

ARTICLES

Alonso, J. M., Stepanova, A. N., Leisse, T. J., Kim, C. J., Chen, H., Shinn, P., Stevenson, D. K., Zimmerman, J., Barajas, P., Cheuk, R., Gadrinab, C., Heller, C., Jeske, A., Koesema, E., Meyers, C. C., Parker, H., Prednis, L., Ansari, Y., Choy, N., Deen, H., Geralt, M., Hazari, N., Hom, E., Karnes, M., Mulholland, C., Ndubaku, R., Schmidt, I., Guzman, P., Aguilar-Henonin, L., Schmid, M., Weigel, D., Carter, D. E., Marchand, T., Risseeuw, E., Brogden, D., Zeko, A., Crosby, W. L., Berry, C. C. and Ecker, J. R. (2003) Genome-wide insertional mutagenesis of *Arabidopsis thaliana. Science,* 301, 653-657.

Antonio, C., Larson, T., Gilday, A., Graham, L, Bergstrom, E. and Thomas-Oates, J. (2007) Quantification of sugars and sugar phosphates in *Arabidopsis thaliana* tissues using porous graphitic carbon liquid chromatography-electrospray ionization mass spectrometry. *J Chromatogr* 1172, 170-178.

Axelos, M., Bardet, C., Liboz, T., Le Van That, A., Curie, C. and Lescure, B. (1989) The gene family encoding the *Arabidopsis thaliana* translation elongation factor EF-1 alpha: molecular cloning, characterization and expression. *Mol Gen Genet,* 219, 106-112.

Bozzo, G. G., Raghothama, K. G. and Plaxton, W. C. (2002) Purification and characterization of two secreted purple acid phosphatase isozymes from phosphate-starved tomato (*Lycopersicon esculentum*) cell cultures. *Eur. J Biochem,* 269, 6278-6286.

Bozzo, G. G., Raghothama, K. G. and Plaxton, W. C. (2004) Structural and kinetic properties of a novel purple acid phosphatase from phosphate-starved tomato (*Lycopersicon esculentum*) cell cultures. *Biochem J,* 377, 419-428.

Bradford, M. M. (1976) A rapid and sensitive method for the quantitation of microgram quantities of protein utilizing the principle of protein-dye binding. *Anal Biochem,* 72, 248-254.

Cashikar, A. G., Kumaresan, R. and Rao, N. M. (1997) Biochemical Characterization and Subcellular Localization of the Red Kidney Bean Purple Acid Phosphatase. *Plant Physiol,* 114, 907-915.

Clough, S. J. and Bent, A. F. (1998) Floral dip: a simplified method for *Agrobacterium*-mediated transformation of *Arabidopsis thaliana. Plant J,* 16, 735-743.

Coello, P. (2002/11) Purification and characterization of secreted acid phosphatase in phosphorus-deficient *Arabidopsis thaliana. Physiologia Plantarum,* 116, 293-298.

del Pozo, J. C., Allona, I., Rubio, V., Leyva, A., de la, P. A., Aragoncillo, C. and Paz-Ares, J. (1999) A type 5 acid phosphatase gene from *Arabidopsis thaliana* is induced by phosphate starvation and by some other types of phosphate mobilising/oxidative stress conditions. *Plant J.,* 19, 579-589.

Doehlert, D. C. (1987) Ketose Reductase Activity in Developing Maize Endosperm. *Plant Physiol,* 84, 830-834.

He, Z. H., Fujiki, M. and Kohorn, B. D. (1996) A cell wall-associated, receptor-like protein kinase. *J Biol Chem,* 271, 19789-19793.

Hegeman, C. E. and Grabau, E. A. (2001) A novel phytase with sequence similarity to purple acid phosphatases is expressed in cotyledons of germinating soybean seedlings. *Plant Physiol.,* 126, 1598-1608.

Hofgen, R. and Willmitzer, L. (1988) Storage of competent cells for *Agrobacterium* transformation. *Nucleic Acids Res,* 16, 9877.

Kaida (2003) Isolation and characterization of four cell wall purple acid phosphatase genes from tobacco cells. *Biochim. biophys acta,* 1625, 134-140.

Kim, S, and Gynheung, A. (1996) Isolation and characterization of a pollen-specific cDNA clone from Easter lily. *J. Plant Biol.,* 39, 197-202.

Klabunde, T., Strater, N., Frohlich, R., Witzel, H. and Krebs, B. (1996) Mechanism of Fe(III)—Zn(II) purple acid phosphatase based on crystal structures. *J. mol. biol.,* 259, 737-748.

Klabunde, T. and Krebs, B. (1997) The dimetal center in purple acid phosphatases. *Metal Sites in Proteins and Models,* 89, 177-198.

Kumar, S., Tamura, K. and Nei, M. (2004) MEGA3: Integrated software for Molecular Evolutionary Genetics Analysis and sequence alignment. *Brief Bioinform,* 5, 150-163.

Li, D., Zhu, H., Liu, K., Liu, X., Leggewie, G., Udvardi, M. and Wang, D. (2002) Purple acid phosphatases of *Arabidopsis thaliana*. Comparative analysis and differential regulation by phosphate deprivation. *J. Biol. Chem.,* 277, 27772-27781.

Li, D. and Wang, D. (2003) cDNA cloning and in vitro expression of three putatave purple acid phosphatase genes from *Arabidopsis. Journal of nature science Hunan Normal University,* 26, 78-82.

Liao, H., Wong, F. L., Phang, T. H., Cheung, M. Y., Li, W. Y., Shao, G., Yan, X. and Lam, H. M. (2003) GmPAP3, a novel purple acid phosphatase-like gene in soybean induced by NaCl stress but not phosphorus deficiency. *Gene,* 318, 103-111.

Liu, L. J., Zhang, Y. C., Li, Q. H., Sang, Y., Mao, J., Lian, H. L., Wang, L. and Yang, H. Q. (2008) COP1-mediated ubiquitination of CONSTANS is implicated in cryptochrome regulation of flowering in *Arabidopsis. Plant Cell,* 20, 292-306.

Lung, S. C., Leung, A., Kuang, R., Wang, Y., Leung, P. and Lim, B. L. (2008) Phytase activity in tobacco (*Nicotiana tabacum*) root exudates is exhibited by a purple acid phosphatase. *Phytochemistry,* 69, 365-373.

Lunn, J. E., Feil, R., Hendriks, J. H., Gibon, Y., Morcuende, R., Osuna, D., Scheible, W. R., Carillo, P., Hajirezaei, M. R. and Stitt, M. (2006) Sugar-induced increases in trehalose 6-phosphate are correlated with redox activation of ADPglucose pyrophosphorylase and higher rates of starch synthesis in *Arabidopsis thaliana. Biochem J,* 397, 139-148.

Luo, B., Groenke, K., Takors, R., Wandrey, C. and Oldiges, M. (2007) Simultaneous determination of multiple intracellular metabolites in glycolysis, pentose phosphate pathway and tricarboxylic acid cycle by liquid chromatography-mass spectrometry. *J Chromatogr A,* 1147, 153-164.

Park, J. Y., Canam, T., Kang, K. Y., Ellis, D. D. and Mansfield, S. D. (2008) Over-expression of an *arabidopsis* family A sucrose phosphate synthase (SPS) gene alters plant growth and fibre development. *Transgenic Res,* 17, 181-192.

Patel, K., Lockless, S., Thomas, B. and McKnight, T. D. (1998) Secreted purple acid phosphatase from *Arabidopsis thaliana. American Society of Plant Physiogists,* 373-374.

Schenk, G., Ge, Y., Carrington, L. E., Wynne, C. J., Searle, I. R., Carroll, B. J., Hamilton, S, and de-Jersey, J. (1999) Binuclear metal centers in plant purple acid phosphatases: Fe—Mn in sweet potato and Fe—Zn in soybean. *Arch. Biochem Biophys,* 370, 183-189.

Schenk, G., Korsinczky, M. L., Hume, D. A., Hamilton, S, and DeJersey, J. (2000) Purple acid phosphatases from bacteria: similarities to mammalian and plant enzymes. *Gene,* 255, 419-424.

Shimaoka, T., Ohnishi, M., Sazuka, T., Mitsuhashi, N., Hara-Nishimura I, Shimazaki, K., Maeshima, M., Yokota, A., Tomizawa, K. and Mimura, T. (2004) solation of intact vacuoles and proteomic analysis of tonoplast from suspension-cultured cells of *Arabidopsis thaliana. Plant Cell Physiol,* 45, 672-683.

Thompson, A. R., Doelling, J. H., Suttangkakul, A. and Vierstra, R. D. (2005) Autophagic nutrient recycling in *Arabidopsis* directed by the ATG8 and ATG12 conjugation pathways. *Plant Physiol,* 138, 2097-2110.

Veljanovski, V., Vanderbeld, B., Knowles, V. L., Snedden, W. A. and Plaxton, W. C. (2006) Biochemical and molecular characterization of AtPAP26, a vacuolar purple acid phosphatase up-regulated in phosphate-deprived *Arabidopsis* suspension cells and seedlings. *Plant Physiol,* 142, 1282-1293.

Wu, J. F., Wang, Y. and Wu, S. H. (2008) Two New Clock Proteins, LWD1 and LWD2, Regulate *Arabidopsis* Photoperiodic Flowering. *Plant Physiol,* 148, 948-959.

Wu, P., Ma, L., Hou, X., Wang, M., Wu, Y., Liu, F. and Deng, X. W. (2003) Phosphate starvation triggers distinct alterations of genome expression in *Arabidopsis* roots and leaves. *Plant Physiol,* 132, 1260-1271.

Xiao, K., Harrison, M. J. and Wang, Z. Y. (2005) Transgenic expression of a novel *M. truncatula* phytase gene results in improved acquisition of organic phosphorus by *Arabidopsis. Planta,* 222, 27-36.

Xiao, K., Katagi, H., Harrison, M. and Wang, Z. Y. (2006) Improved phosphorus acquisition and biomass production in *Arabidopsis* by transgenic expression of a purple acid phosphatase gene from *M. truncatula. Plant Science,* 170, 191-202.

Zhang, W., Gruszewski, H. A., Chevone, B. I. and Nessler, C. L. (2008) An *Arabidopsis* purple Acid phosphatase with phytase activity increases foliar ascorbate. *Plant Physiol,* 146, 431-440.

Zhu, H. F., Qian, W. Q., Lu, X. Z., Li, D. P., Liu, X., Liu, K. F. and Wang, D. W. (2005) Expression patterns of purple acid phosphatase genes in *Arabidopsis* organs and functional analysis of AtPAP23 predominantly transcribed in flower. *Plant Molecular Biology,* 59, 581-594.

What is claimed is:

1. A method to make a transgenic plant comprising: introducing a phosphatase gene into a plant, the phosphatase gene encoding a polypeptide comprising SEQ ID NO: 2 or a polypeptide having at least 90% sequence identity to SEQ ID NO: 2; SEQ ID NO: 2, wherein introducing the phosphatase gene into the plant increases growth rate, sugar content, crop yield, or the combination thereof, relative to wild-type plants.

2. The method of claim 1, wherein the phosphatase gene is a purple acid phosphatase gene comprising a nucleotide sequence encoding a polypeptide comprising the amino acid sequence of SEQ ID NO: 2.

3. The method of claim 1, wherein the phosphatase gene is a purple acid phosphatase gene comprising the nucleotide sequence of SEQ ID NO:1 or a nucleotide sequence having at least 90% sequence identity to SEQ ID NO:1.

4. The method of claim 2, wherein said nucleotide sequence comprises SEQ ID NO:1.

5. The method of claim 1, wherein introducing the phosphatase gene up-regulates the enzymatic activity of sucrose phosphate synthase in the transgenic plant relative to the wild-type plant.

6. The method of claim 1, wherein introducing the phosphatase gene up-regulates the sucrose and/or glucose level in the transgenic plant relative to the wild-type plant.

7. The method of claim 1, wherein introducing the phosphatase gene increases the growth rate of the transgenic plant relative to the wild-type plants.

8. The method of claim 1, wherein introducing the phosphatase gene results in a higher crop yield of the transgenic plant relative to the wild-type plants.

9. The method of claim 1, wherein the plant is a species selected from one of the group consisting of the following genera: *Asparagus, Bromus, Hemerocalli, Hordeum, Loliu, Panicum, Pennisetum, Saccharum, Sorghum, Trigonell, Triticum, Zea, Antirrhinum, Arabidopsis, Arachis, Atropa, Brassica, Browallia, Capsicum, Carthamus, Cichorium, Citrus, Chrysanthemum, Cucumis, Datura, Daucus, Digitalis, Fragaria, Geranium, Glycine, Helianthus, Hyscyamus, Ipomoea, Latuca, Linum, Lotus, Solanum lycopersicon, Majorana, Malva, Gossypium, Manihot, Medicago, Nemesia, Nicotiana, Onobrychis, Pelargonium, Petunia, Ranunculus, Raphanus, Salpiglossis, Senecio, Sinapis, Solanum, Trifolium, Vigna*, and *Vitis*.

10. The method of claim 1, wherein the plant is a species selected from the family *Brassica*.

* * * * *